United States Patent [19]
Crow et al.

[11] Patent Number: 6,022,879
[45] Date of Patent: Feb. 8, 2000

[54] BATHOCUPROINE TREATMENT OF NEUROLOGIC DISEASE

[75] Inventors: John P. Crow; Joseph S. Beckman, both of Birmingham, Ala.

[73] Assignee: UAB Research Foundation, Birmingham, Ala.

[21] Appl. No.: 09/173,105

[22] Filed: Oct. 15, 1998

Related U.S. Application Data

[60] Provisional application No. 60/062,428, Oct. 15, 1997.
[51] Int. Cl.$^7$ .................................................. A61K 31/445
[52] U.S. Cl. ........................... 514/319; 514/320; 514/321
[58] Field of Search ..................................... 514/319, 320, 514/321

[56] References Cited

U.S. PATENT DOCUMENTS 5,834,457  11/1998  Bredesen et al. ........................ 514/188

OTHER PUBLICATIONS

Ghadge et al., "Mutant superoxide dismutase–1–linked familial amyotrophic lateral sclerosis:molecular mechanisms of neuronal death and protection", J. Neurosci. (1997), 17(22), pp. 8756–8766 (abstract).

*Primary Examiner*—Kevin E. Weddington
*Attorney, Agent, or Firm*—Benjamin Aaron Adler

[57] ABSTRACT

The present invention provides a method of treating amyotrophic lateral sclerosis and other neurologic diseases by administering bathocuproine or a related analog. Also provided are pharmaceutical compositions of bathocuproine.

11 Claims, 33 Drawing Sheets

BATHOCUPROINE TREATMENT OF NEUROLOGIC DISEASE

CROSS-REFERENCE TO RELATED APPLICATION

This non-provisional application claims benefit of priority of U.S. provisional application Ser. No. 60/062,428, filed Oct. 15, 1997, now abandoned.

FEDERAL FUNDING LEGEND

The present invention was created in part using federal funds under NIH grants NS33291, HL22334 and NS24338. Accordingly, the U.S. government has certain rights in this invention.

BACKGROUND OF THE INVENTION

1. Field of the Invention

The present invention relates generally to the fields of immunology and protein chemistry. More specifically, the present invention relates to a novel treatment of treatment of neurologic diseases such as amyotrophic lateral sclerosis using compounds such as bathocuproine or derivatives thereof.

2. Description of the Related Art

The discovery of mutations to Cu,Zn superoxide dismutase in a subset of familial ALS cases has raised hopes for understanding the selective vulnerability of motor neurons as well as the pathogenesis of the remaining 98% of ALS cases not related to superoxide dismutase mutations. Neurofilaments give axons their structural integrity and define axonal diameter (Hoffman et al., 1987, Brady, 1993). Neurofilaments are composed of three subunits identified as light (NF-L), medium (NF-M) and heavy (NF-H) which assemble in a 6:2:1 ratio to form long macromolecular filaments (Nixon and Lewis, 1986, Nixon and Shea, 1992). Consequently, NF-L is more abundant than the other two subunits in neurons. NF-L is capable of homologous assembly whereas NF-M and NF-H are not competent to assemble in the absence of NF-L (Cohlberg et al., 1995). Each neurofilament subunit consists of conserved head and rod domains and a more variable acidic tail domain. The rod domains are principally composed of alpha helixes, which wrap around each other to form a superhelix of parallel coiled coils (Lupas, 1996). Neurofilament dimers assemble into protofilaments in a head-to-tail arrangement. The head domain is also important for lateral interactions between neurofilaments (Heins et al., 1993). Two protofilaments wrap around each other to form protofibrils, which in turn combine with three other protofibrils to form the characteristic 10 nm diameter neurofilaments seen by electron microscopy. The assembly of neurofilaments involves many complex associations between subunits, each stabilized by hydrophobic interactions that often involve tyrosine (Heins et al., 1993).

Because axons from human motor neurons extend up to a meter in length and constitute >99% of cell volume, they contain more neurofilaments than other neurons except possibly dorsal root ganglia. The importance of neurofilaments to normal motor neuron viability is underscored by the development of motor neuron disease in transgenic mice expressing point mutations in NF-L or b y overexpressing either NF-L or NF-H (Cote et al., 1993, Xu et al., 1993, Lee et al., 1994). Moreover, axonal transport is disrupted in the NF-H transgenic mice (Collard et al., 1995). Disruption of neurofilament assembly can selectively injure motor neurons, perhaps by interfering with retrograde transport of trophic support from target tissues. Abnormal accumulation of neurofilaments in degenerating motor neurons is one of the pathological hallmarks of ALS, and neurofilaments may be significant targets for superoxide dismutase-catalyzed tyrosine nitration by peroxynitrite (Beckman, 1996 a & b).

Amyotrophic lateral sclerosis (ALS) is a fatal neurodegenerative disease characterized by the selective loss of motor neurons and accompanying loss of voluntary muscular function. ALS typically begins as weakness in one limb during middle adult life and progresses via contiguous groups of motor neurons to ultimately result in paralysis and death within 3–5 years (Williams et al. 1991). Ninety percent of ALS cases are sporadic with no identifiable genetic or environmental risk factors. A familial inheritance pattern has been observed in the remaining 10% of ALS cases and one-fifth of those result from dominant missense mutations to the antioxidant enzyme copper, zinc superoxide dismutase (Cu,Zn superoxide dismutase) (Rosen et al. 1993). Early histopathological changes in ALS include abnormal accumulations of neurofilaments and other cytoskeletal proteins in the cell soma as well as within proximal axonal swellings (Hirano 1991). The clinical course and histopathology of sporadic and familial forms of ALS are similar, providing hope that understanding superoxide dismutase-associated ALS will illuminate the pathogenesis of sporadic ALS.

Over 50 dominant, independently arising mutations at 26 different amino acid positions in the antioxidant enzyme Cu,Zn superoxide dismutase have been described in familial ALS patients (Rosen et al. 1994b; Deng et al. 1993b; Hirano 1991b). All but two of the mutations occur outside the active site and affect amino acid positions important for maintaining the stability of superoxide dismutase. The most common mutation involves an alanine to valine transition at position 4 and is associated with a particularly rapid progression of the disease (Rosen et al. 1994a). Mutant and wild-type enzymes are equally expressed in familial ALS patients and total superoxide dismutase activity may be decreased by as much as 60% in some patients (Bowling et al. 1993). Other superoxide dismutase mutants appear to have near normal catalytic activity (Borchelt et al. 1994). Afflicted individuals express superoxide dismutase mutants from birth in all tissues (Robberecht et al. 1994) even though the pathology in ALS is largely limited to motor neurons. Symptoms of ALS typically do not develop until after age 40, whereupon the disease is largely restricted to motor neurons. Heterozygous mutant superoxide dismutase carriers have a >85% chance of developing the disease (Cudkowicz et al. 1997).

Transgenic mice expressing human ALS-superoxide dismutase mutants suffer motor neuron degeneration, paralysis, and death even though they still express their endogenous wild-type superoxide dismutase (Wong et al. 1995; Dal Canto et al. 1995; Ripps et al. 1995; Gurney et al. 1994). Transgenic mice expressing wild-type human superoxide dismutase do not develop motor neuron disease. Conversely, in Cu,Zn superoxide dismutase-deficient knock-out mice, motor neurons develop normally, though they are more susceptible to cell death after axonal injury (Reaume et al. 1996). Thus, the loss of superoxide scavenging by superoxide dismutase per se cannot account for the selective loss of motor neurons in ALS, though it may play a contributing role. Geneticists ascribe the dominant action of the superoxide dismutase mutants to a gain-of-function. Rather than creating an entirely new toxic function, the gain-of-function may simply be an increased efficiency of an injurious reaction catalyzed by wild-type superoxide dismutase which may also contribute to sporadic ALS.

Superoxide dismutase-catalyzed nitration by peroxynitrite could be one gain-of-function contributing to the development of ALS (Beckman et al. 1993). Peroxynitrite, formed from the diffusion-limited reaction of superoxide with nitric oxide (Padmaja et al. 1993), is an alternate substrate for wild-type superoxide dismutase (Beckman et al. 1992; Ischiropoulos et al. 1992). The reaction of peroxynitrite with superoxide dismutase yields a potent nitrating species that adds a nitro group ($-NO_2$) to tyrosine residues in other proteins (Beckman et al. 1992; Ischiropoulos et al. 1992). Superoxide dismutase is not inactivated by peroxynitrite and can catalyze nitration indefinitely. In contrast, the formation of hydroxyl radical by the reaction of hydrogen peroxide with superoxide dismutase inactivates superoxide dismutase after only a few catalytic cycles (Wiedau-Pazos et al. 1996; Hodgson et al. 1975; Yim et al. 1996). Although hydrogen peroxide-inactivated superoxide dismutase does not scavenge superoxide or react further with hydrogen peroxide, it is still effective at catalyzing tyrosine nitration (Beckman et al. 1992).

Disruption of neurofilament assembly in transgenic mice lead to motor neuron degeneration (Mathieu et al. 1995; Collard et al. 1995; Cote et al. 1994; Xu et al. 1993). Neurofilaments are important in maintaining the structure and diameter of motor neuron axons. Because axons may constitute as much as 99% of total cell volume, neurofilaments are particularly abundant proteins in motor neurons. Abnormal aggregates of neurofilaments within the cell soma and proximal axons are early pathological events in the development of ALS which may contribute to cell death (Xu, Z. et al. 1993b).

The prior art is deficient in the lack of effective means of treating neurologic diseases such as amyotrophic lateral sclerosis. The present invention fulfills this longstanding need and desire in the art.

SUMMARY OF THE INVENTION

Superoxide dismutase catalyzes the nitration of specific tyrosine residues in proteins by peroxynitrite ($ONOO^-$), which may be the damaging gain-of-function resulting from mutations to superoxide dismutase associated with familial amyotrophic lateral sclerosis (ALS). Disassembled neurofilament-L was more susceptible to tyrosine nitration catalyzed by superoxide dismutase in vitro. Neurofilament-L was selectively nitrated compared to the majority of other proteins present in brain homogenates. Assembled neurofilament-L was more resistant to nitration, suggesting that the susceptible tyrosine residues were protected by intersubunit contacts in assembled neurofilaments. Electrospray mass spectrometry of trypsin-digested neurofilament-L showed that tyrosine 17 in the head region and tyrosines 138, 177, and 265 in alpha-helical coil regions of the rod domain of neurofilament-L were particularly susceptible to superoxide dismutase-catalyzed nitration. Nitrated neurofilament-L inhibited the assembly of unmodified neurofilament subunits, suggesting that the affected tyrosines are located in regions important for intersubunit contacts. Neurofilaments are major structural proteins expressed in motor neurons and known to be important for their survival in vivo. Superoxide dismutase-catalyzed nitration of neurofilament-L may have a significant role in the pathogenesis of ALS.

Mutations to Cu,Zn superoxide dismutase linked to familial ALS enhance an unknown toxic reaction that leads to the selective degeneration of motor neurons. However, the question of how more than 50 different missense mutations produce a common toxic phenotype remains perplexing. The zinc affinity of four ALS-associated superoxide dismutase mutants was decreased up to 30-fold compared to wild-type superoxide dismutase, but that both mutants and wild-type superoxide dismutase retained copper with similar affinity. Neurofilament-L bound multiple zinc atoms with sufficient affinity to potentially remove zinc from both wild-type and mutant superoxide dismutase while having a lower affinity for copper. The loss of zinc from wild-type superoxide dismutase approximately doubled its efficiency for catalyzing peroxynitrite-mediated tyrosine nitration, suggesting that one gained function by superoxide dismutase in ALS may be an indirect consequence of zinc loss. Nitration of protein-bound tyrosines is a permanent modification which can adversely affect protein function. Thus, the toxicity of ALS-associated superoxide dismutase mutants may be related to enhanced catalysis of protein nitration subsequent to zinc loss. By acting as a high capacity zinc sink, NF-L could foster the formation of zinc-deficient superoxide dismutase within motor neurons.

In one embodiment of the present invention, there is provided a method of removing copper from a form of superoxide dismutase in an individual in need of such treatment, comprising the step of administering to the individual a pharmacologically effective dose of bathocuproine or a derivative or analog thereof.

In another embodiment of the present invention, there is provided a pharmaceutical composition, comprising bathocuproine and a pharmaceutically acceptable carrier.

In yet another embodiment of the present invention, there is provided a method of treating an individual with ALS in an individual in need of such treatment, comprising the step of administering to the individual a pharmacologically effective dose of bathocuproine or a derivative or analog thereof.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 11 shows the disruption of neurofilament assembly by nitrated NF-L. Assembly was visualized by negative staining by electron microscopy (×60,000).

FIG. 23A: Reaction solutions contained 10 $\mu$M of SOD subunit in 0.1 M KPi, pH 7.4 at 37° C. Tetranitromethane (TNM) (0.1 mM) was added at time zero followed by 0.1 mM H$_2$O$_2$ at the time indicated. Catalase (800 units/ml) added to decompose remaining H$_2$O$_2$ and measure superoxide production related solely to SOD reoxidation. FIG. 23B: The dose-respone for superoxide production is seen with increases in either SOD subunit or H$_2$O$_2$ concentration. Reactions contained indicated amounts of SOD and H$_2$O$_2$ and 0.1 mM TNM in 0.1 M KPi, pH 7.4 at 37° C.

FIG. 24A) Reactions contained 20 $\mu$M PAPANONOate in 0.1 M KPi, pH 7.4 at 37° C. Once a steady-state level of NO had been reached, SOD (5 $\mu$M A4V or wild-type) was added followed ~20 sec later by H$_2$O$_2$. The immediate decrease in NO levels relfect superoxide-mediated consumption by superoxide generated by the reverse dismutase reaction. FIG. 24B:

Peroxynitrite production was measured via the oxidation of dichlorodihydrofluorescein (DCDHF, 0.1 mM) (ref 30) in 0.1 M KPi, pH 7.4 at 37° C. Reactions contained 10 $\mu$M of the indicated SOD; 20 $\mu$M H$_2$O$_2$ was added at the time indicated for the green and red traces. No H$_2$O$_2$ was added for the black trace which contained wild-type SOD only; DCDHF oxidation in this case was due to the formation of nitrogen dioxide from the slow reaction of NO with molecular oxygen.

Figure 25:
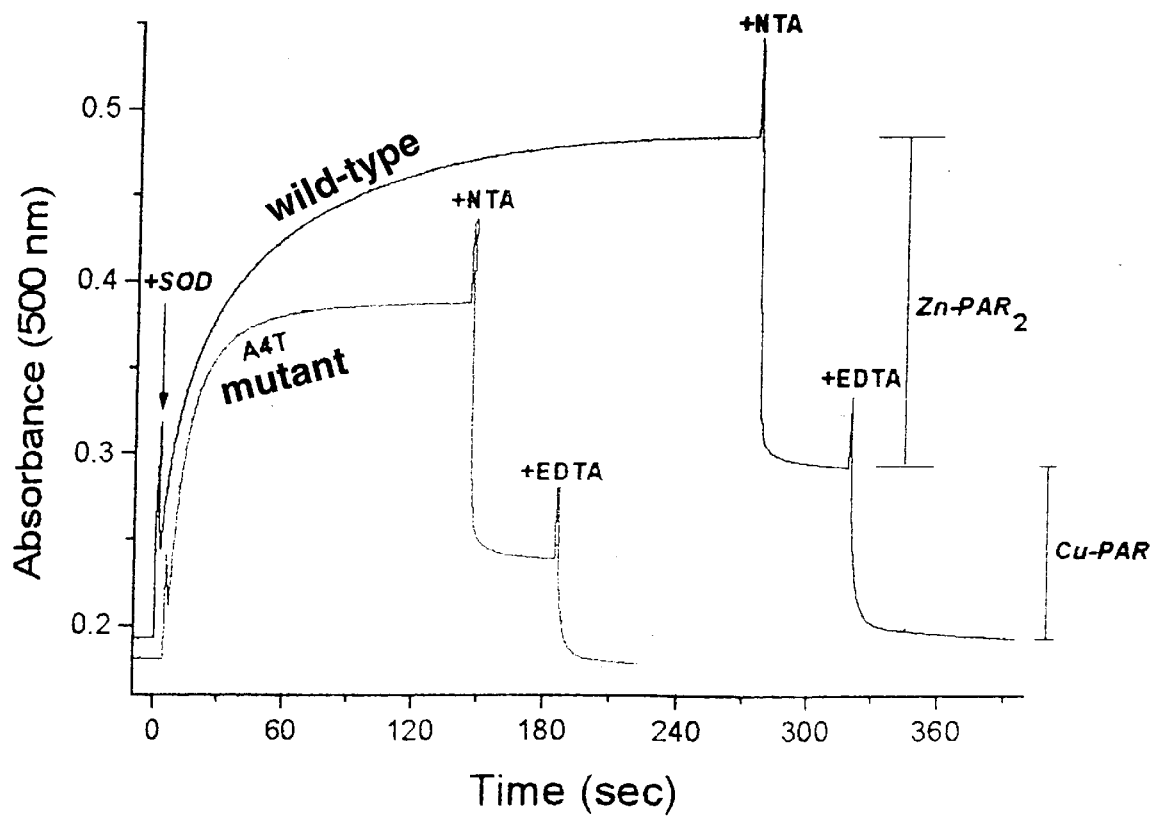

FIG. 25 shows the PAR Assay for Total Metal Content of SOD. Briefly, SOD is added to a borate buffered solution containing 6 M guanidine-HCl and 0.1 mM of the chromophoric chelator PAR. Both zinc and copper are released from SOD and bound up by PAR; nitrilotriacetic acid will remove zinc from Zn-PAR$_2$ but will not affect Cu-PAR whereas EDTA will remove Cu from Cu-PAR. Differential absorbance changes allow for sensitive quantitation of enzyme-bound zinc and copper.

Figure 26:
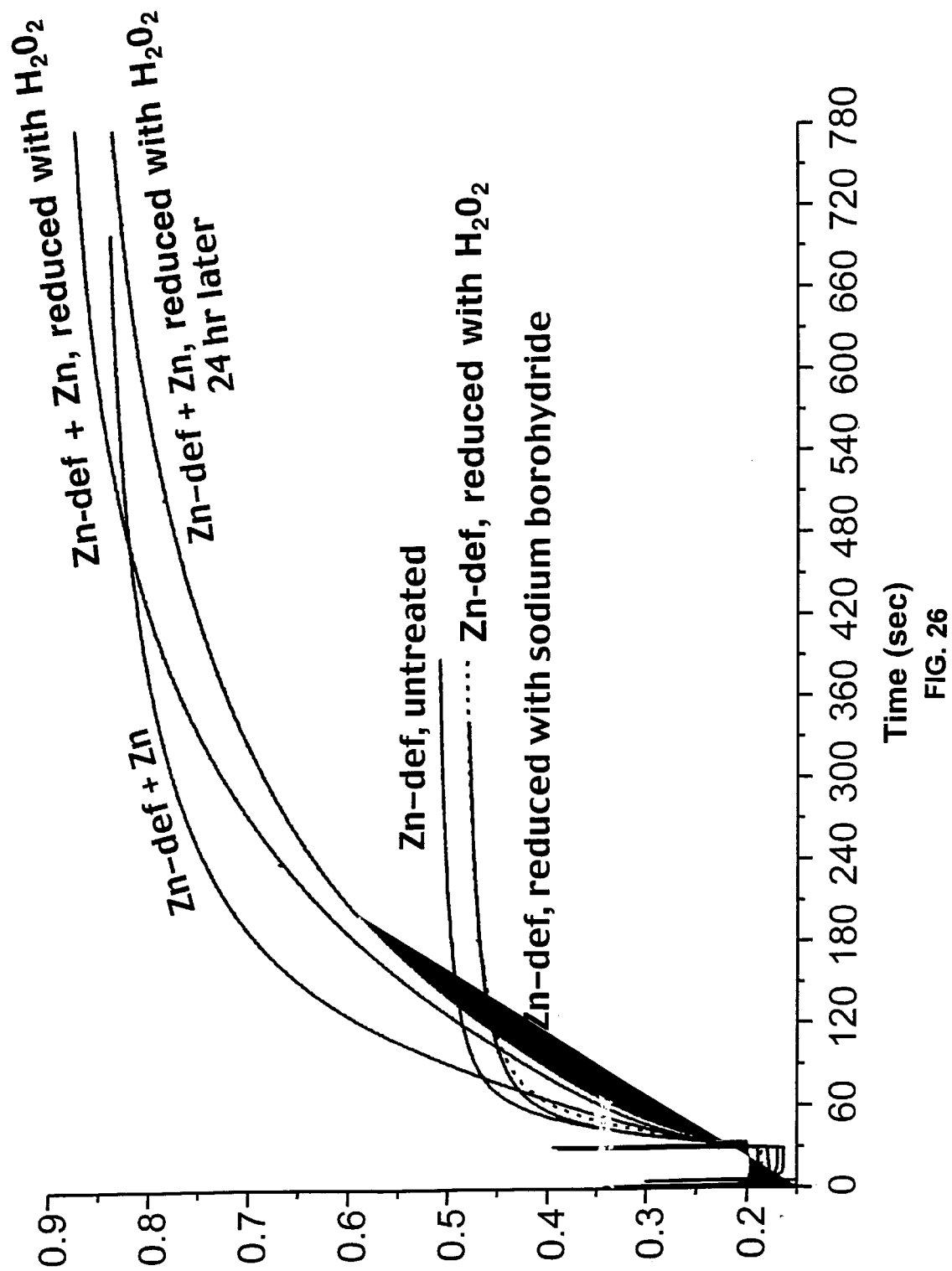

FIG. 26 shows the Effect of Zinc and Enzyme-Bound Copper Reduction on SOD Denaturation Rates. SODs (5 $\mu$M) were added to a borate buffered solution containing 5 M guanidine-HCl and 0.1 mM of the chromophoric chelator PAR. One molar equivalent of zinc was added to the "Zn-def+Zn" enzymes for 5 min prior to adding to the PAR solution. Pre-reduction was carried out by incubating the SODs in a small volume together with either one equivalent of H$_2$O$_2$ or four molar eqivalents of sodium borohydride for 5 min prior to adding to the PAR assay. H$_2$O$_2$-reduced SOD containing added zinc was incubated overnight at room temperature prior to subsequent PAR assay.

Figure 27:
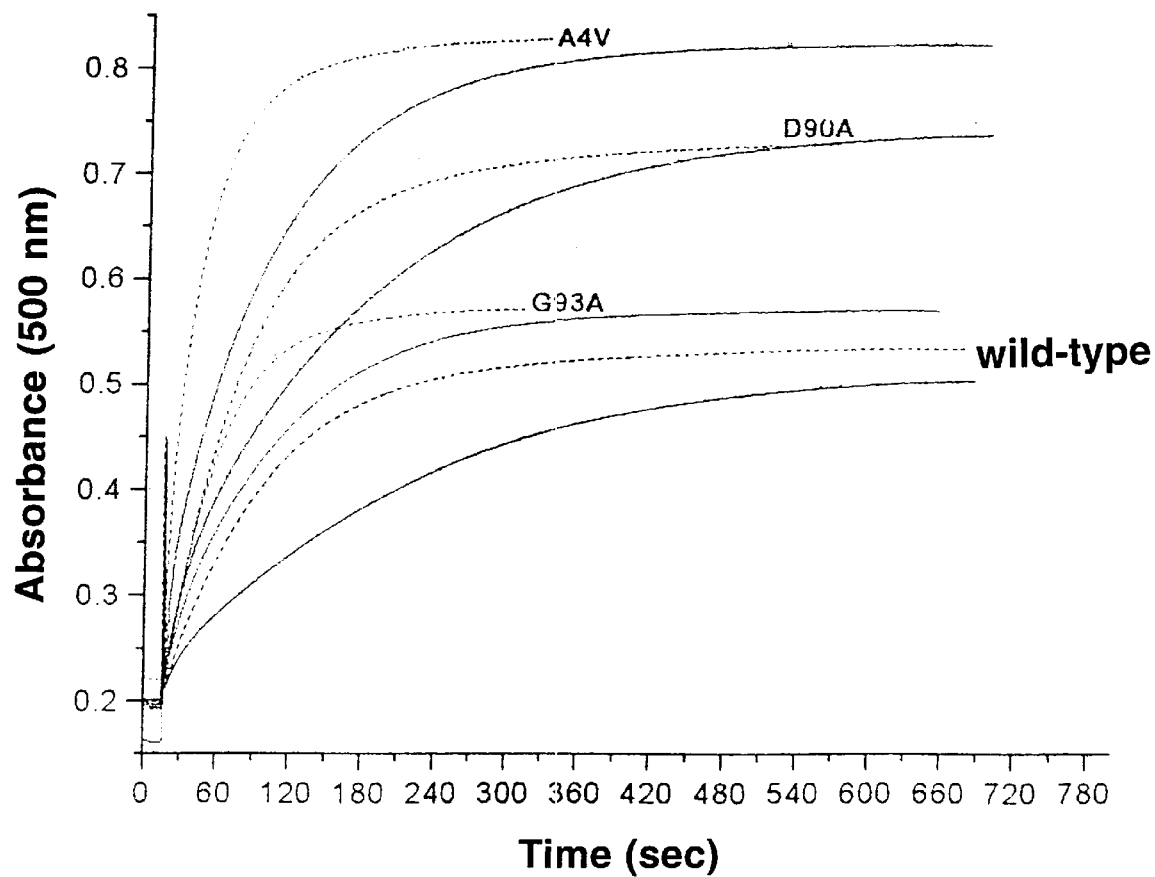

FIG. 27 shows the Effect of Eznyme-Bound Copper Reduction on SOD Denaturation Rates. Different amounts of untreated SODs (dashed lines) were added to the PAR assay (5 M guanidine-HCl) as described above. The same amounts of each SOD were pre-reduced with one molar equivalent of H$_2$O$_2$ in a small volume for 5 min and added to the PAR assay (solid lines). The slower rates of denaturation/metal release were the same if reduced enzymes were allowed to reoxidize overnight (not shown).

Figure 28:
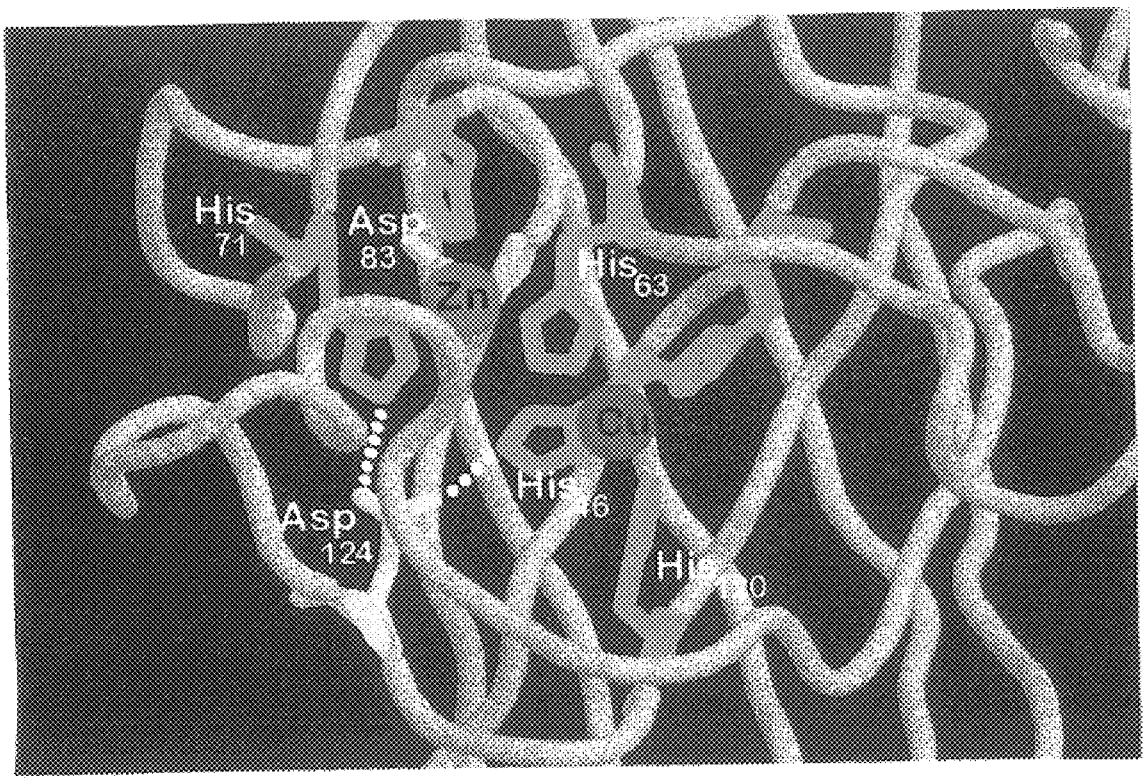

FIG. 28 shows the Crystal structure of human Cu,Zn SOD highlighting active site. Copper is bound by four histidine residues, zinc by three histidines and aspartate$_{83}$ (behind zinc in this veiw). Histidine$_{63}$ is shared by both copper and zinc when the copper is in the +2 state. Upon reduction, Cu$^{+1}$ breaks the shared His$_{63}$ bond thereby allowing His$_{63}$ to conform more closely to the perferred geometry of zinc; this may be basis for the increased resistence to denaturation upon reduction. Asp$_{124}$ hydrogen bonds to His$_{46}$ and His$_{71}$ and apparently helps stabilize the geometry for zinc binding. Mutation of Asp$_{124}$ to Asn$_{124}$ (D124N) results in a dramatically decreased affinity for zinc. Once more of the FALS mutants structures become known, it may well be that the different mutations decrease zinc binding affinity by altering the proximity of Asp$_{124}$ to His$_{43}$ and His$_{71}$.

Figure 29:
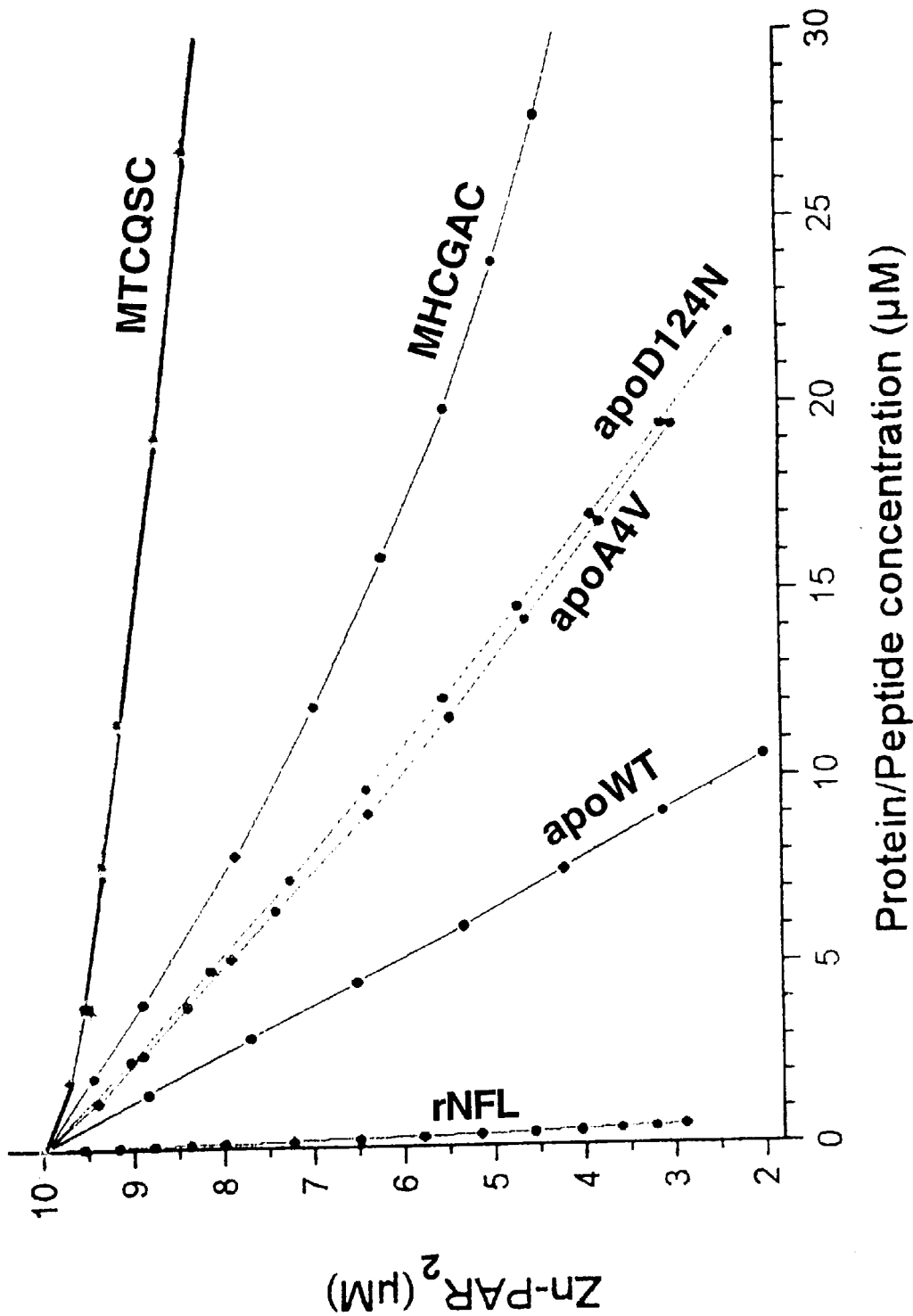

FIG. 29 shows the Zinc Binding by apoSODs, CCS Peptides, and NF-L. A solution of 100 μM PAR and 10 μM zinc (resulting in 10 μM Zn-PAR$_2$ complex) in 0.1 M KPi, pH 7.4 at 37° C. was titrated with apoSODs, CCS peptides, and rNF-L as indicated. The aborbance drop at each point is proportional to the loss of Zn-PAR$_2$ complex associated with zinc binding by the protein or peptide. The more protein subunit (or peptide) required to bind a given amount of zinc, the lower the affinity. Thus, the slope is an indication of relative affinity given the caveats mentioned in the footnote below[1]. The concentrations of CCS peptides were measured via their thiol content with Ellman's Reagent (DTNB).

[1]NOTE that slopes reflect relative affinity only when the binding stoichiometry is 1:1, i.e., if a protein bound two zinc atoms per mole then the slope would be twice as steep even though the affinity was unchanged. In the case of apoSODs and CCS peptides, the stoichiometry is 1:1 and thus comparisons are valid.

Figure 30:
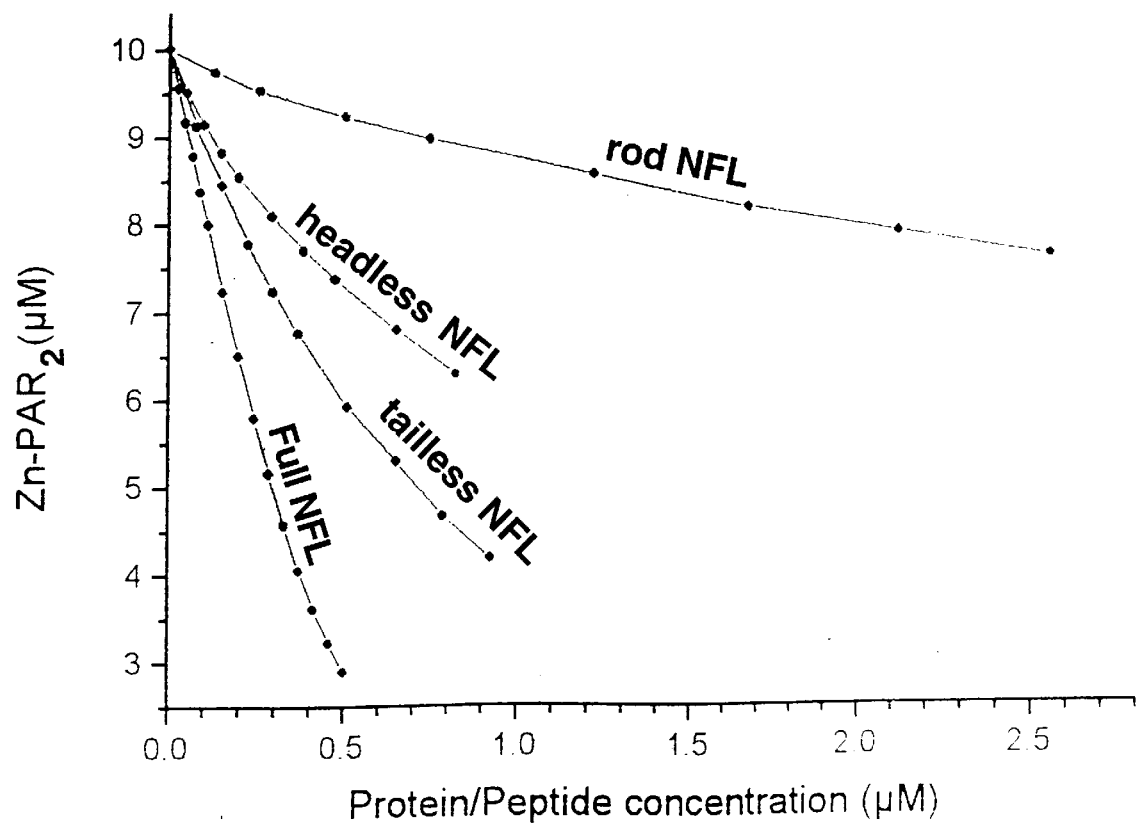

FIG. 30 shows Zinc Binding by Truncated NF-L Mutants. Titrations of a 10 μM Zn-PAR$_2$ solution were carried out. cDNA's for these NF-L mutants were a gift of Drs. Don Cleveland and Michael Lee. Preparation of full length rNF-L and mutants is described above.

Figure 31:
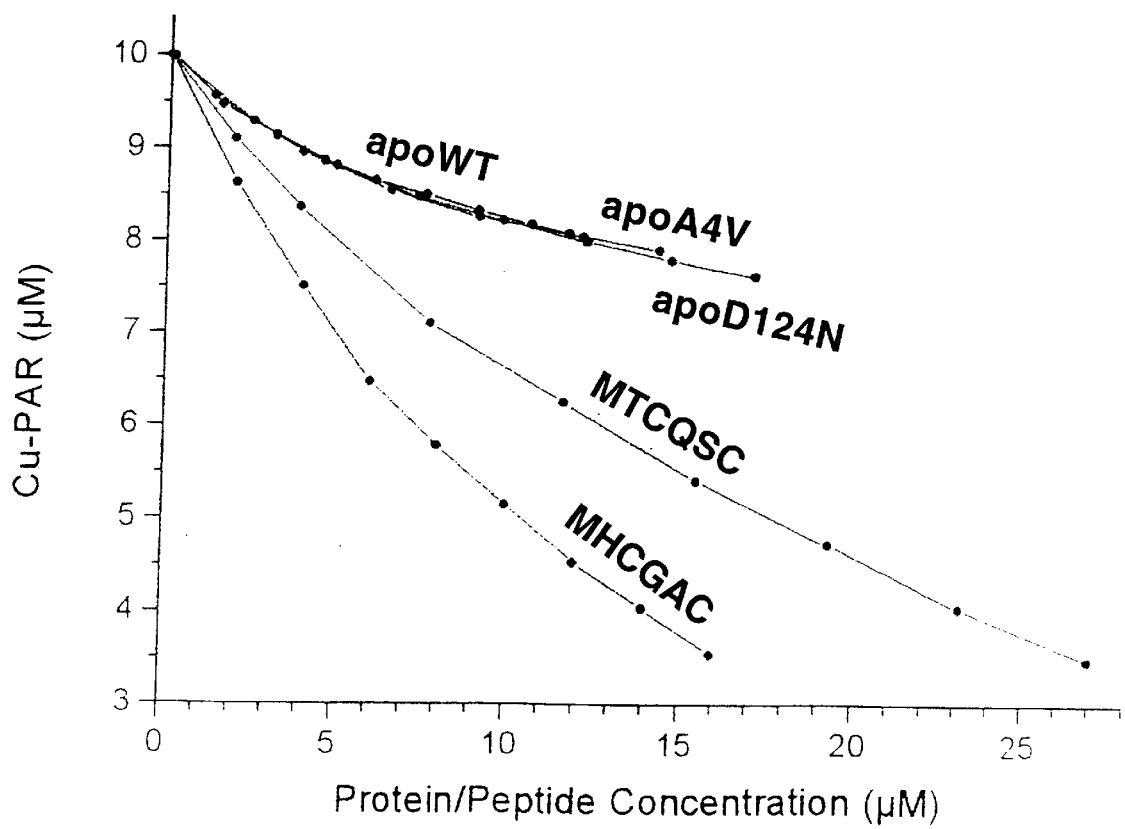

FIG. 31 shows Copper Binding by apoSODs and CCS Peptides. Titrations of a 10 μM Cu-PAR solution were carried out as described above except that 10 μM was used rather than zinc. ApoSODs were prepared as described and the concentrations of CCS peptides were determine via their thiol content using DTNB.

DETAILED DESCRIPTION OF THE INVENTION

The present invention is directed to a method of removing copper from a form of superoxide dismutase in an individual in need of such treatment, comprising the step of administering to the individual a pharmacologically effective dose of bathocuproine or a derivative or analog thereof.

In yet another embodiment of the present invention, there is provided a method of treating an individual with amyotrophic lateral sclerosis in an individual in need of such treatment, comprising the step of administering to the individual a pharmacologically effective dose of bathocuproine or a derivative or analog thereof.

It is specifically contemplated that pharmaceutical compositions may be prepared using the bathocuproine of the present invention. In such a case, the pharmaceutical composition comprises bathocuproine and a pharmaceutically acceptable carrier. A person having ordinary skill in this art would readily be able to determine, without undue experimentation, the appropriate dosages and routes of administration of the novel protein of the present invention.

The following examples are given for the purpose of illustrating various embodiments of the invention and are not meant to limit the present invention in any fashion.

EXAMPLE 1
Expression of Mouse NF-L in *E. coli*

A full length cDNA clone of mouse neurofilament-L in a PET3a vector (Novagen, Madison, Wis.) was expressed in *E. coli* as described (Heins et al., 1993, Crow et al., 1997). The bacterial expressed NF-L contained an N-terminal methionine not present in native NF-L, which was considered as residue zero to be consistent with the numbering of the eukaryotic sequence.

EXAMPLE 2
Nitration In vitro

Peroxynitrite was synthesized by a quenched flow reactor from acidified nitrite and hydrogen peroxide (Beckman et al., 1994a, Koppenol et al., 1995). Recombinant mouse NF-L was used at a concentration of 0.4 mg/ml in nitration experiments. Diethylenetriaminepentaacetic acid (DTPA, 0.1 mM) and the indicated concentrations of human superoxide dismutase were added to a total of 2 ml of the NF-L solution. Formation of nitrotyrosine was followed at 430 nm (e=4,400 M$^{-1}$·cm$^{-1}$) by sequential additions of peroxynitrite into a rapidly stirred cuvette in a spectrophotometer maintained at 37° C. Nitration of brain homogenates was determined by western blotting with nitrotyrosine antibodies. Rat brain was homogenized in five volumes of 50 mM potassium phosphate, pH 7.4, and bovine superoxide dismutase was added to 1 and 2 mg/ml. Peroxynitrite (1 mM) was then added with rapid mixing. Proteins were separated on SDS-PAGE using 12% gels and transferred to nitrocellulose. The membranes were incubated with monoclonal 1A6 anti-nitrotyrosine (1:500; Beckman et al., 1994b), washed, probed with biotinylated anti-mouse IgG, and developed using avidin-HRP plus diaminobenzidine (Ye et al., 1996).

EXAMPLE 3
In vitro Neurofilament Assembly

Triplet neurofilament proteins were prepared from bovine spinal cord (Chiu and Norton, 1982, Strong and Jakowec, 1994) and the Triton X100-insoluble pellet was solubilized in 6 M urea, 1 mM dithiothreitol (DTT), 10 mM Tris, pH 8.1, and centrifuged (10,000×g, 30 min). A 1.5 mg/ml solution was assembled by dialysis overnight at 37° C. against 50 mM MES, 160 mM NaCl, 1 mM DTT, pH 6.25, spotted onto copper-coated grids, negatively stained with 1% phosphotungstate, and photographed with a Hitachi H-7000 transmission electron microscope. An aliquot of soluble triplet neurofilament subunits containing 4 mg/ml in 50 mM potassium phosphate, 6 M urea, pH 7.4, was treated with peroxynitrite (1 mM). Nitrotyrosine content was determined spectrally to be 40 μM. Nitrated neurofilament subunits were mixed in a ratio of 1:4 with untreated soluble subunits to give a final nitrotyrosine content of ~0.9% of total tyrosine and allowed to dialyze overnight.

EXAMPLE 4
Mass Spectrometry of NF-L

Nitrated neurofilament-L (200 μg) was incubated in argon-bubbled 6 M guanidine-HCl, 50 mM Tris, 1 mM dithiothreitol, pH 8.6, for 2 hours at 37° C., treated with 10 mM iodoacetamide in the dark for 2 hours and then dialyzed exhaustively against 50 mM (NH$_4$)$_2$CO$_3$ at 4° C. (Greis et al., 1996). The reduced and alkylated protein was then digested with 5 μg trypsin dissolved in 0.1% acetic acid for 16 hours at 37° C. The protein was lyophilized, stored at −80° C. and resuspended in 50 μl of 0.1% trifluoroacetic acid immediately before use. Approximately 10 μg of digested protein were directly injected with a 7 μl/min flow rate of 0.1% trifluoracetic acid into a 0.3 mm i.d. C18 reversedphase capillary column. The mobile phase was generated by a Hewlett-Packard model 1050 HPLC initially at 0.5 ml/min. It was then split 1:70 with a LC Packings Accurat splitter to provide the low flow rate for the capillary column. The peptides were loaded with a 3 min isocratic wash and eluted with a linear 0–80% gradient of acetonitrile over 30 min. The column eluant was introduced into an electrospray ionization interface and the resulting positive ions entered the Perkin-Elmer Sciex API-III triple quadrupole mass spectrometer operating with a 70 volt orifice potential. Putative nitrated peaks were tentatively identified by an increase in mass of 45 units due to the nitro group. Each spectrum was searched for the expected mass/charge (m/z) of the singly, doubly and triply charged ions for each tyrosine-containing peptide. Nitration was confirmed by using the MS/MS mode in which peptide ions of interest were selected in the first quadrupole of the mass spectrometer and subjected to collision-induced fragmentation with argon in the second quadrupole (Mann and Wilm, 1995). The fragments were then separated in the third quadrupole of the mass spectrometer to confirm the sequence and site of nitration. The MS/MS experiments were conducted with the orifice potential raised to 85 volts.

EXAMPLE 5
Neurofilaments Nitration

Figure 1A:
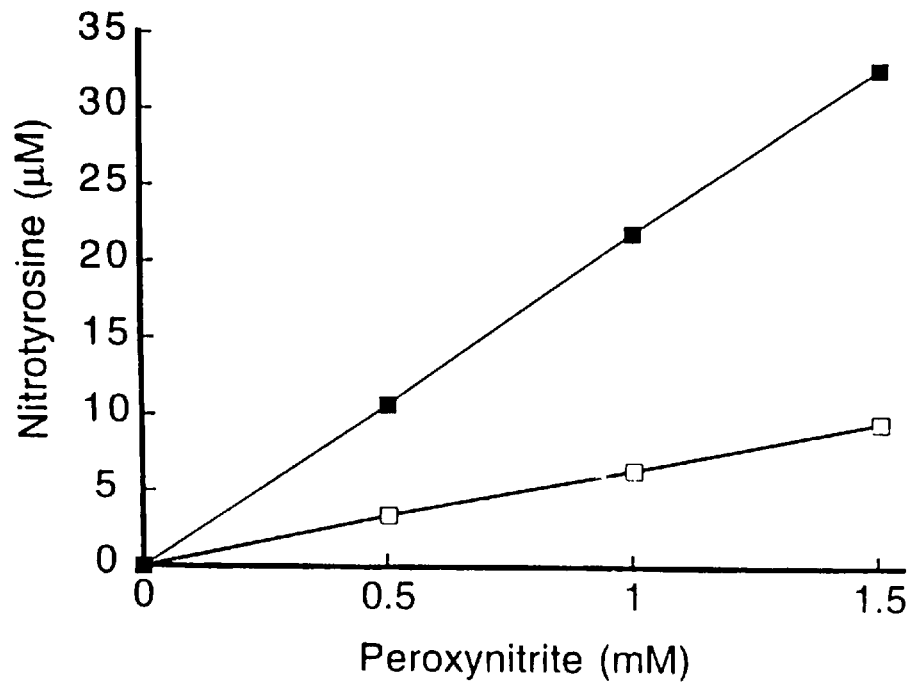
FIG. 1 shows the nitration of NF-L which was allowed to assemble in 50 mM potassium phosphate, 0.16M NaCl at pH 7.4 compared to disassembled NF-L. Peroxynitrite (0.5 mM final concentration) was sequentially three times to a rapidly stirred 3 ml cuvette containing 0.4 mg/ml NF-L, 50 mM potassium phosphate, pH 7.4 and 37° C. with or without human superoxide dismutase. This NF-L concentration corresponded to approximately 120 $\mu$M total tyrosine residues. Nitrotyrosine formation was monitored spectrally at 430 nm. Results are representative of experiments with three different NF-L preparations.
Figure 1B:
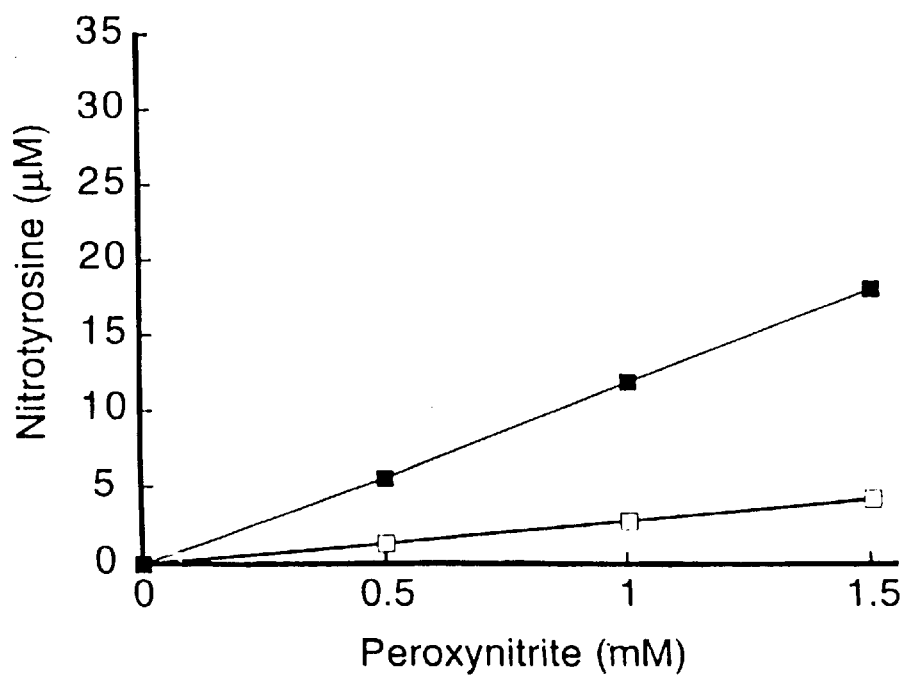
Figure 2:
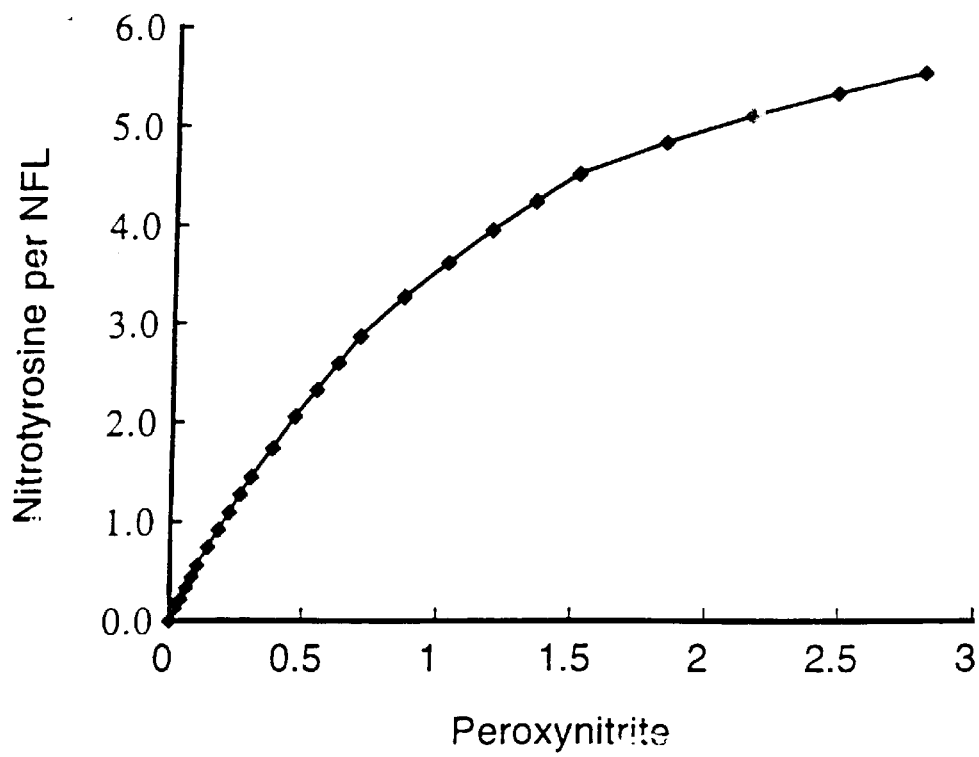
FIG. 2 shows that increasing concentrations of peroxynitrite resulted in the nitration of approximately six tyrosines in disassembled NF-L. The nitration was conducted in a rapidly stirred 3 ml cuvette containing 0.4 mg/ml NF-L, 50 mM potassium phosphate, pH 7.4 and 37° C. and monitored at 430 nm. The NF-L treated with peroxynitrite here was then used for the MS characterization of nitration sites.
Figure 3:
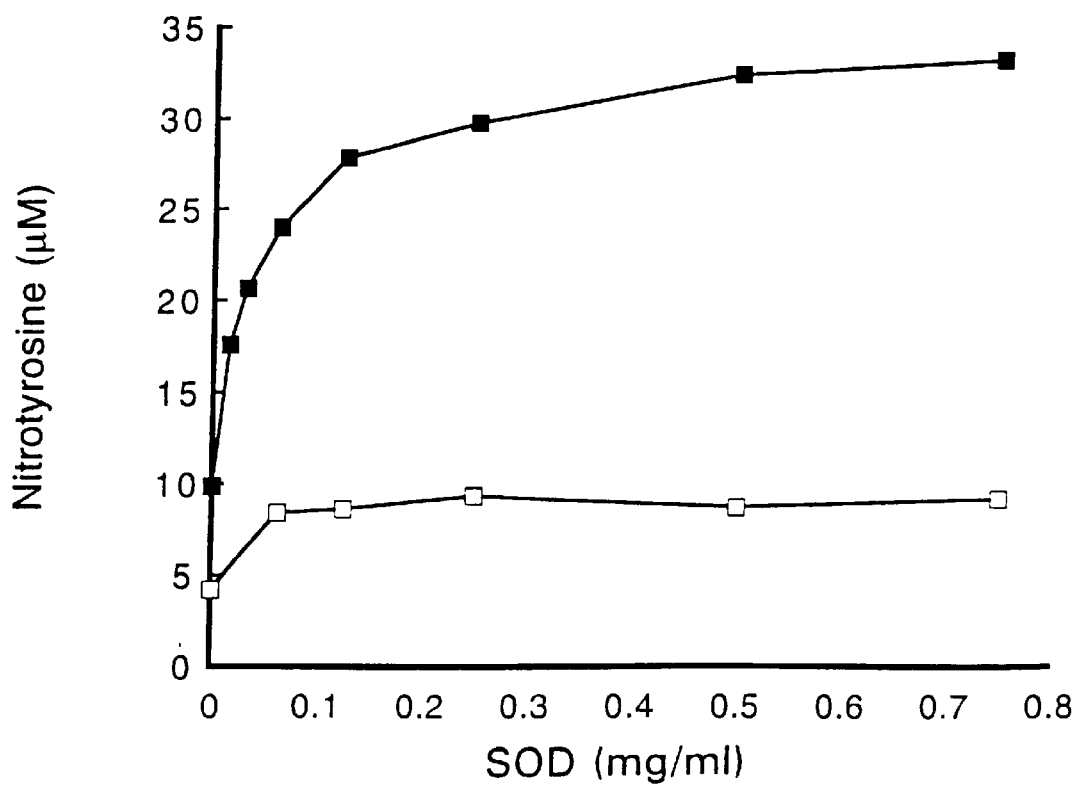
FIG. 3 shows that human Cu,Zn superoxide dismutase enhanced nitration of NF-L compared to BSA. Peroxynitrite (0.5 mM) was added to solutions of (filled square) NF-L or (unfilled square) BSA (0.4 mg/ml) in 0.75 M Tris, pH 8.0. Human Cu,Zn superoxide dismutase has no tyrosines and did not contribute to the increased absorbance observed at 430 nm.
Figure 4A:
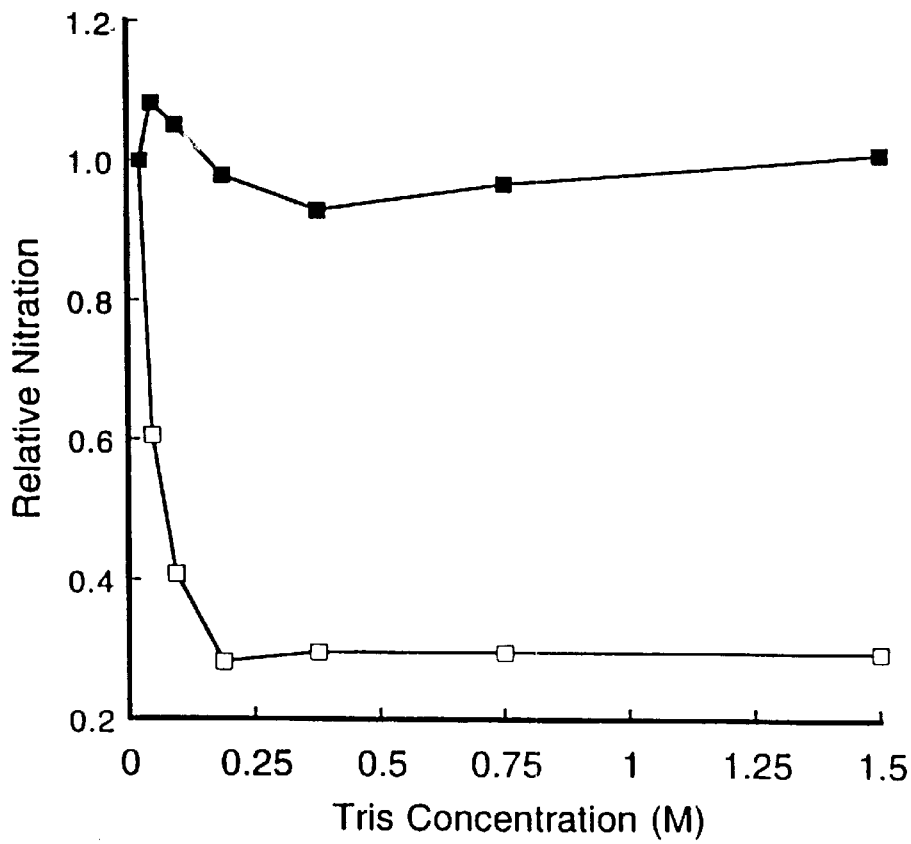
FIG. 4 shows the effect of increasing concentrations of Tris on superoxide dismutase-catalyzed versus non-catalyzed nitration of NF-L (FIG. A) and BSA (FIG. B). Closed symbols included 10 $\mu$M human superoxide dismutase and open symbols have no superoxide dismutase. Both NF-L and BSA were at 0.4 mg/ml in 50 mM potassium phosphate, pH 7.4 and 37° C. and monitored at 430 nm. Each was treated with 1 mM peroxynitrite.
Figure 4B:
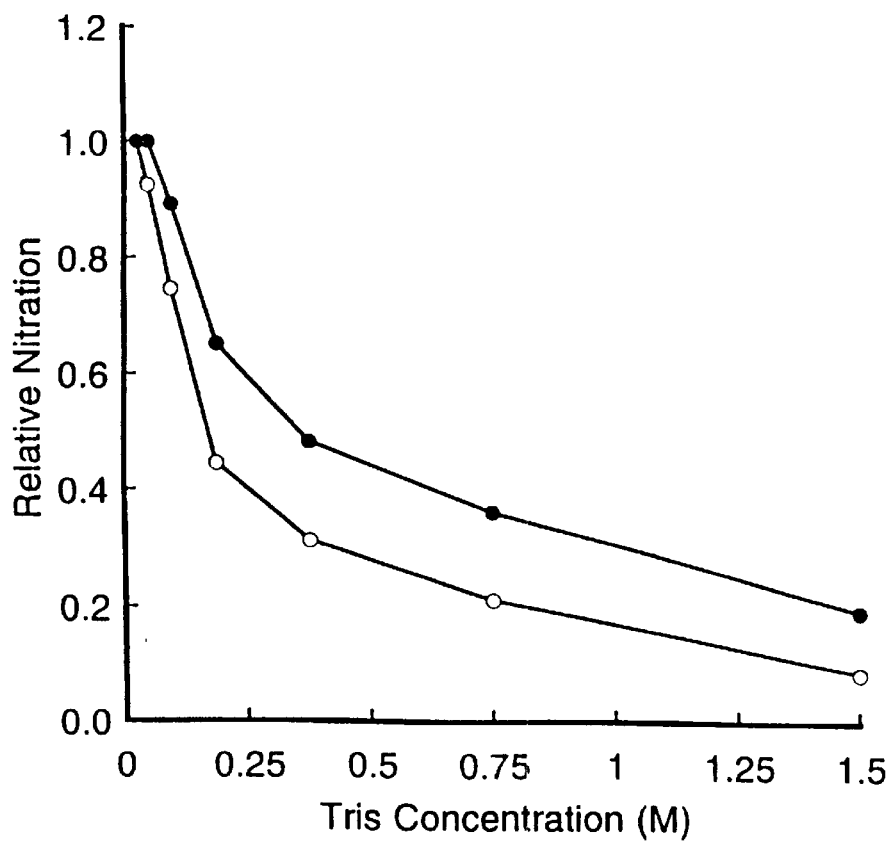

Superoxide dismutase enhanced the nitration of disassembled NF-L by peroxynitrite more efficiently than NF-L that had been assembled by dialysis (FIG. 1). A maximum of six tyrosines out of 20 total tyrosines in mouse NF-L were nitrated by peroxynitrite (FIG. 2). The nitration of NF-L reached a plateau at higher but still physiologically relevant concentrations of superoxide dismutase as has been demonstrated for phenolic nitration catalyzed by superoxide dismutase (FIG. 3) (Beckman et al., 1992). Bovine serum albumin (BSA) has a similar molecular mass and contains about the same number of tyrosine residues as NF-L and was used as an comparative target for superoxide dismutase-catalyzed nitration by peroxynitrite. Superoxide dismutase only slightly enhanced the nitration of BSA, even though both BSA and NF-L were about equally nitrated by peroxynitrite without superoxide dismutase (FIG. 3). Superoxide dismutase also did not significantly enhance nitration of other randomly selected proteins β-galactosidase, α-amylase, ovalbumin, carbonic anhydrase, alcohol dehydrogenase, catalase, and phosphorylase b by peroxynitrite. Molar concentrations of Tris at pH 8 are commonly used to resuspend NF-L pellets and during investigations on its effects on nitration, Tris greatly decreases the non-catalyzed nitration of BSA and NF-L by peroxynitrite, but had little effect on superoxide dismutase-catalyzed nitration of NF-L (FIG. 4). The amount of non-superoxide dismutase-catalyzed nitration of tyrosine is decreased by adding other organic molecules to provide alternative targets for peroxynitrite (Beckman et al., 1992, Ischiropoulos et al., 1992a, Ischiropoulos et al., 1992b) as exist in cells or tissue homogenates. The total number of tyrosines that can be nitrated in either Tris or potassium phosphate buffers was not increased significantly by the presence of superoxide dismutase. However, higher concentrations of peroxynitrite were required to acheive the same extent of nitration in the absense of superoxide dismutase.

Figure 5:
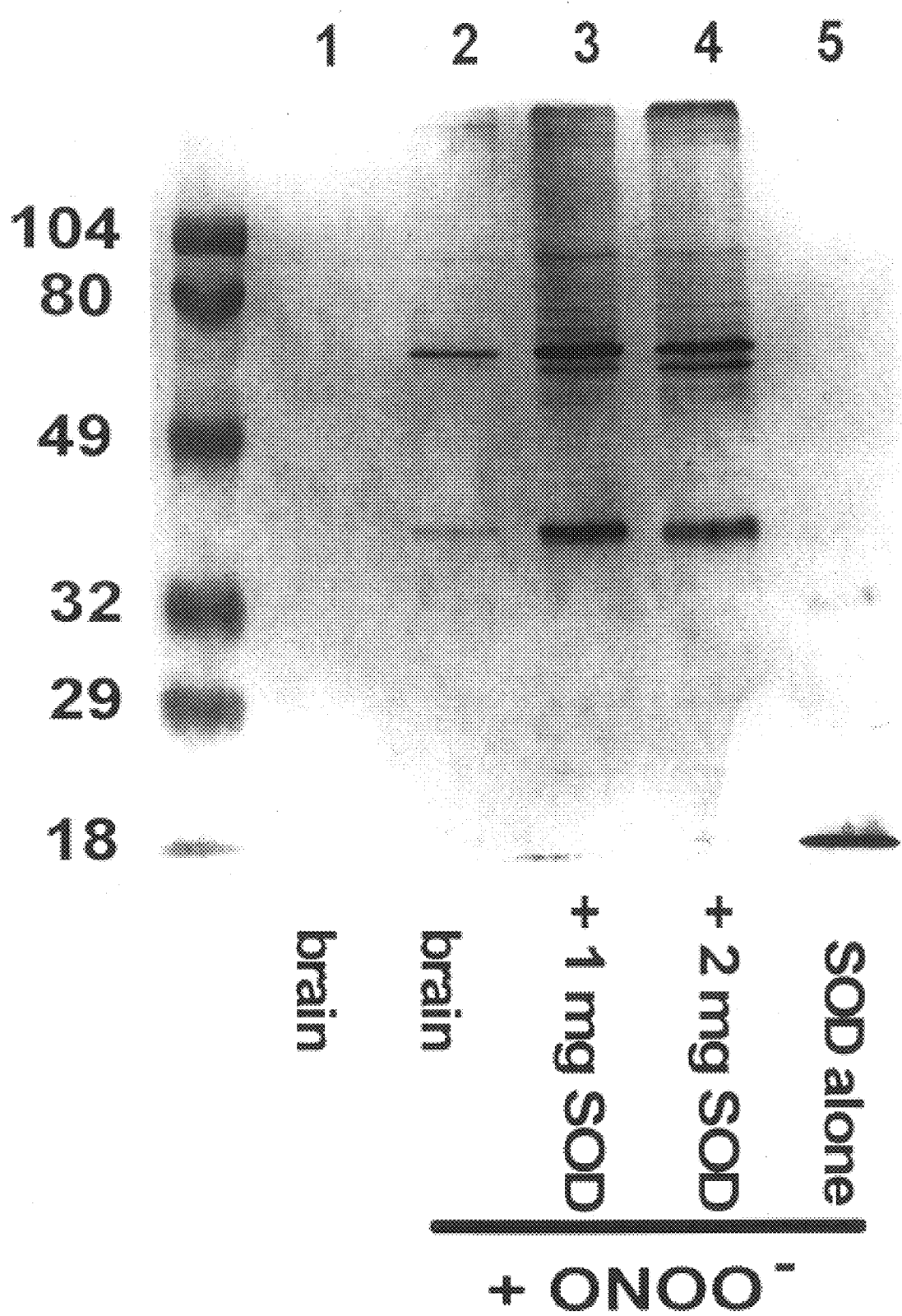
FIG. 5 shows the effect of superoxide dismutase on nitration of proteins of a rat brain homogenate treated with 1 mM peroxynitrite. The lane at the far left contained molecular weight markers; supernatant from brain homogenate was loaded onto lanes 1–4. Samples in lanes 2–5 were treated with 1 mM peroxynitrite in the absence (lane 2) or presence (lanes 3–5) of bovine superoxide dismutase. The 68 kD band was identified as NF-L and one of a few proteins showing enhanced nitration by superoxide dismutase. Lane 5 contained bovine superoxide dismutase which nitrated itself in the absence of other target proteins.

When peroxynitrite was added to a rat brain homogenates, superoxide dismutase selectively enhanced the nitration of NF-L over most other proteins (FIG. 5). The nitrated band at approximately 68 kD shown in FIG. 5 was both reactive and immunoprecipable with monoclonal NF-L antibody, showing that NF-L is preferentially nitrated by peroxynitrite plus superoxide dismutase in the presence of the multitude of alternative substrates for peroxynitrite present in cells.

EXAMPLE 6
Mass Spectral Characterization of Nitration

Figure 6A:
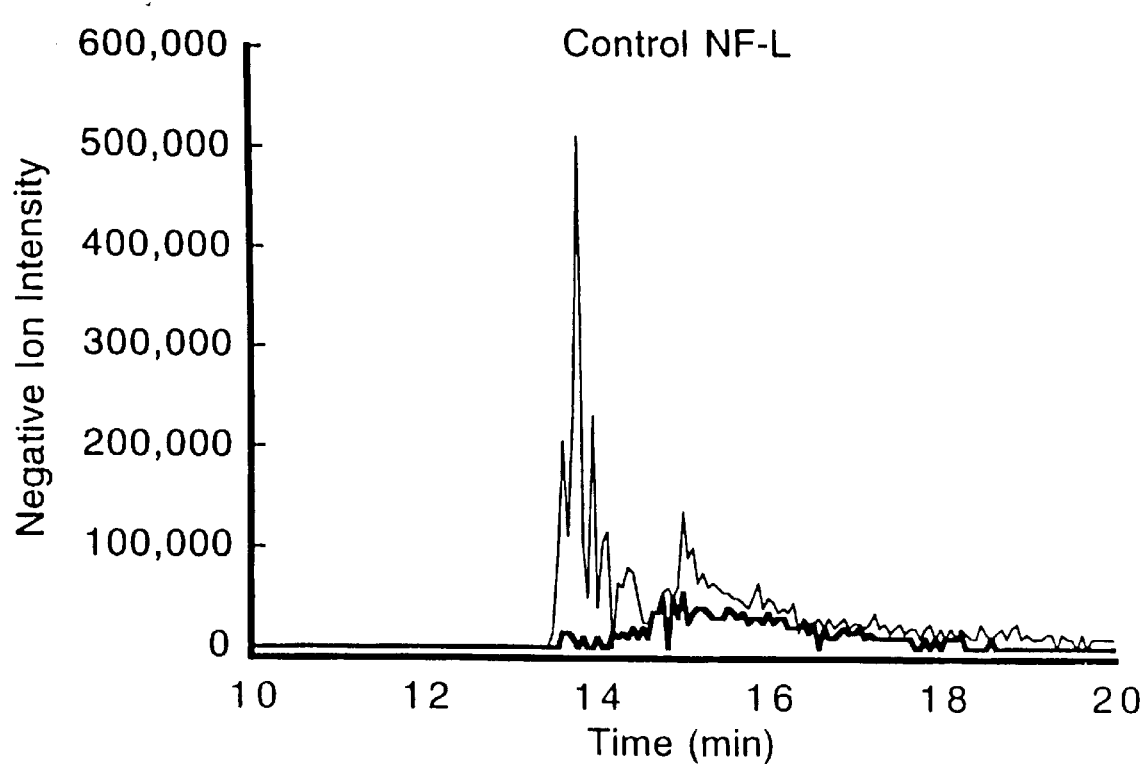
FIG. 6 shows the elution of the non-nitrated (a) versus nitrated (b) head domain peptide YQETPR from the HPLC as monitored by electrospray MS. The majority of this peptide as present as a singly charged ion with a mass of 764 (thin line), which was increased by 45 in the nitrated peptide (thick line). The small signals outside of the main peaks resulted from isotopic derivatives of other peptides with similar masses.
Figure 6B:
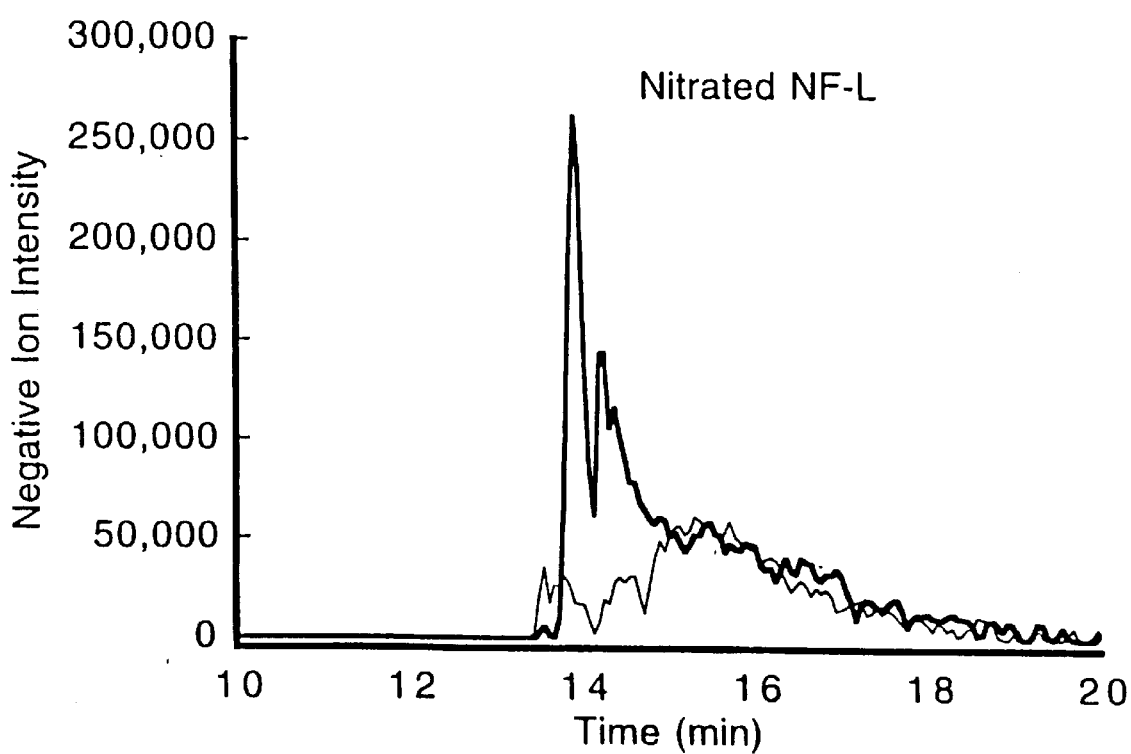
Figure 7A:
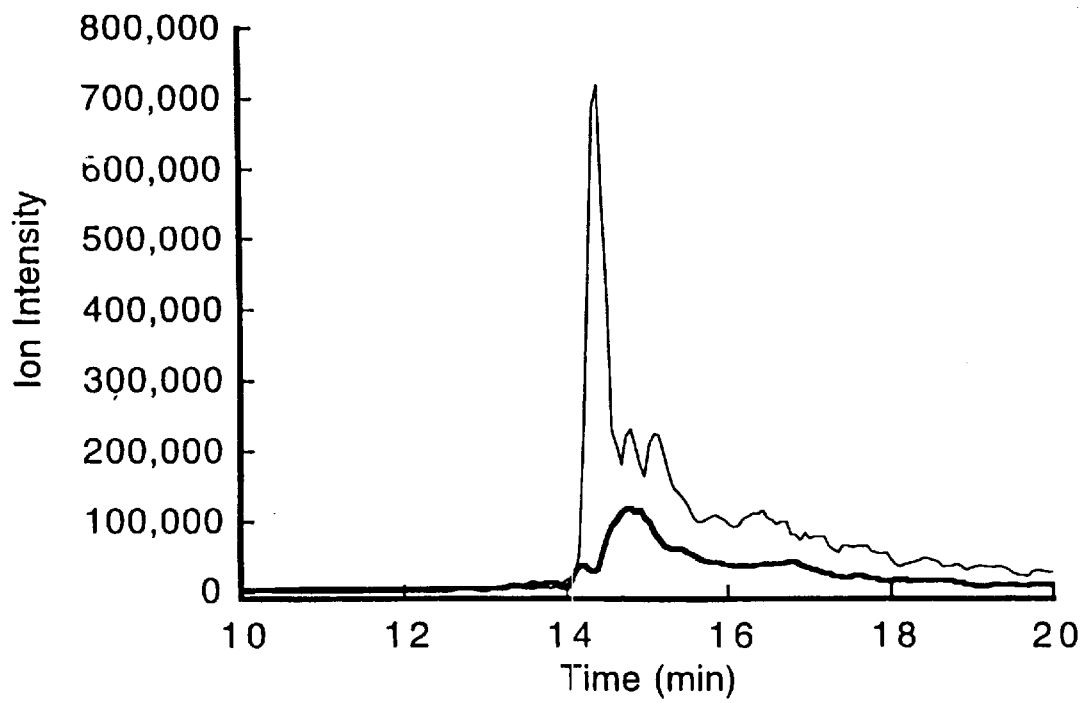
FIG. 7 shows the elution of the non-nitrated (a) versus nitrated (b) rod domain peptide ALYEQEIR from the HPLC as monitored by electrospray MS. The peptide was mostly present as the doubly charged ion. The thin lines correspond to m/z intensity of 511 expected for the non-nitrated peptide and the thicker lines to the m/z intensity of 534 expected for the nitrated peptide. The m/z increase was only 22 since the peptide was doubly charged.
Figure 7B:
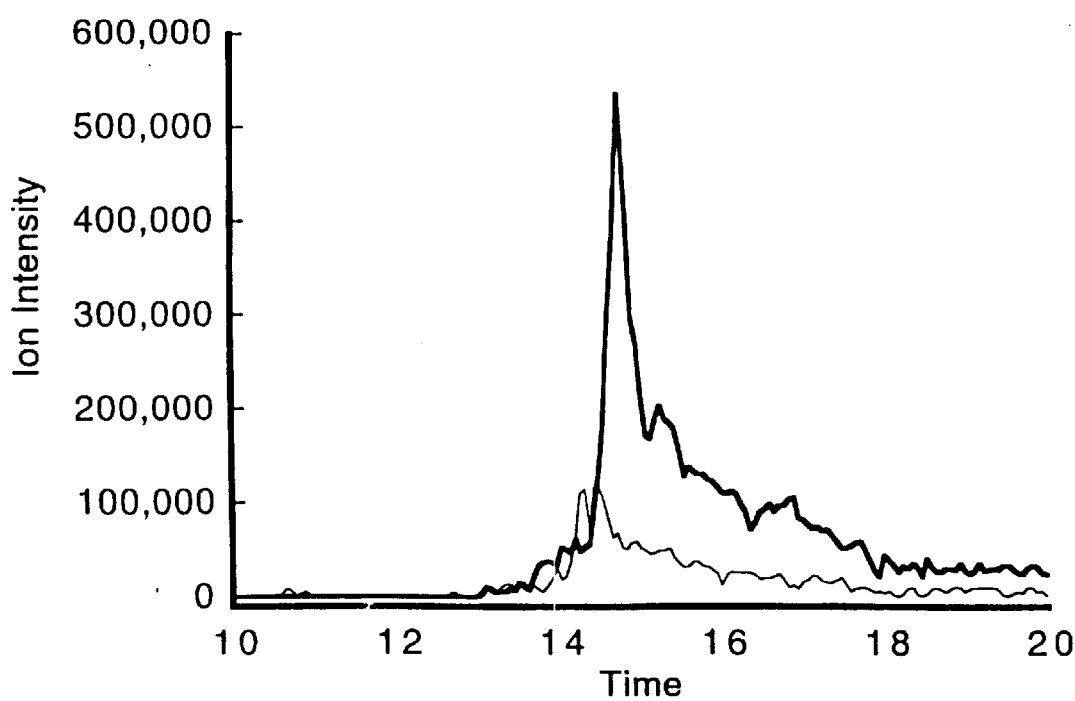
Figure 8A:
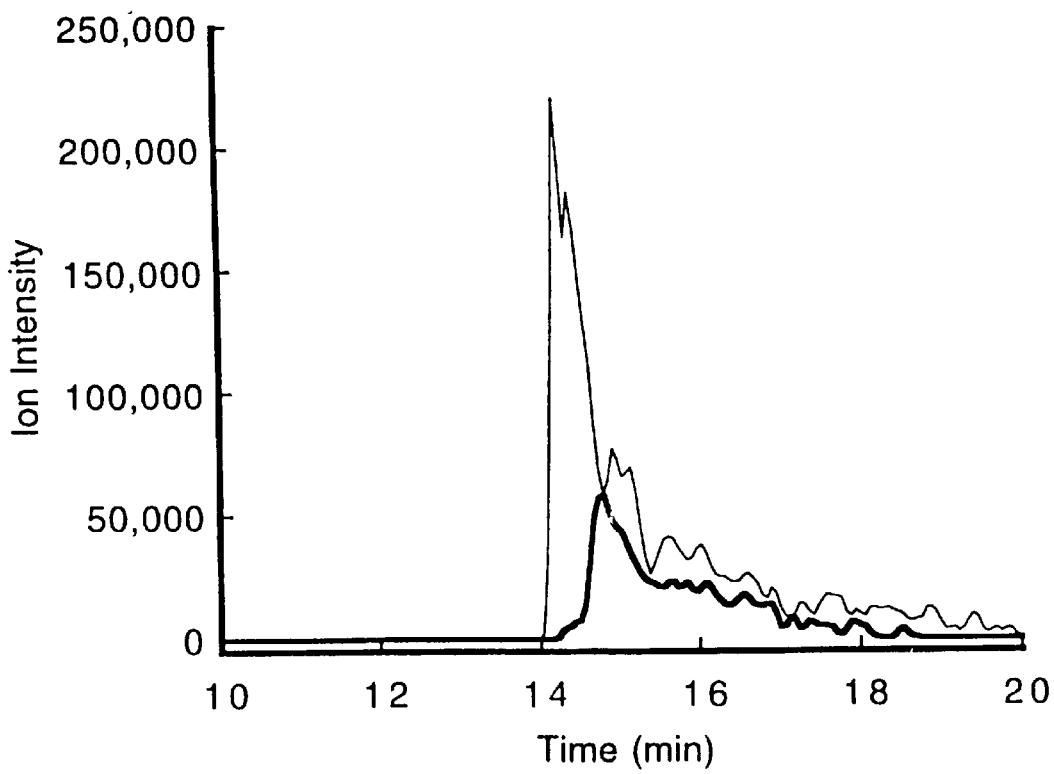
FIG. 8 shows the elution of the non-nitrated (a) versus nitrated (b) rod domain peptide YEEEVLSR from the HPLC as monitored by electrospray MS. The parent peptide was mostly present as the doubly charged ion. The thin lines correspond to m/z intensity of 513 expected for the non-nitrated peptide and the thicker lines to the m/z intensity of 535 expected for the nitrated peptide.
Figure 8B:
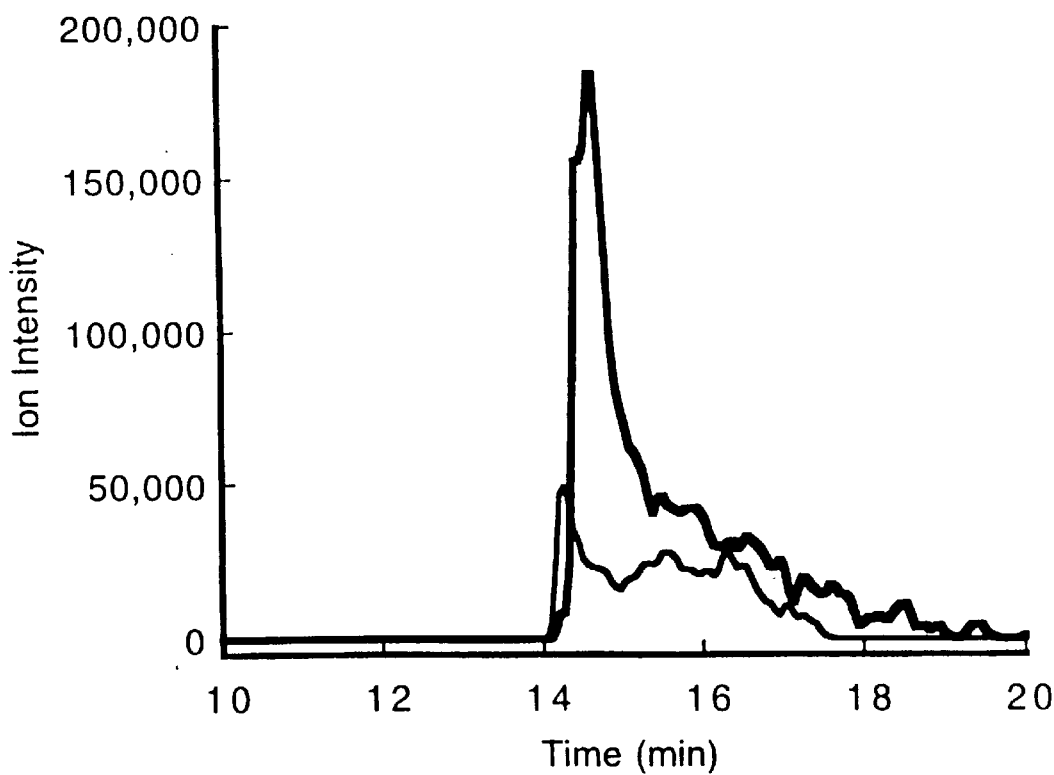
Figure 9A:
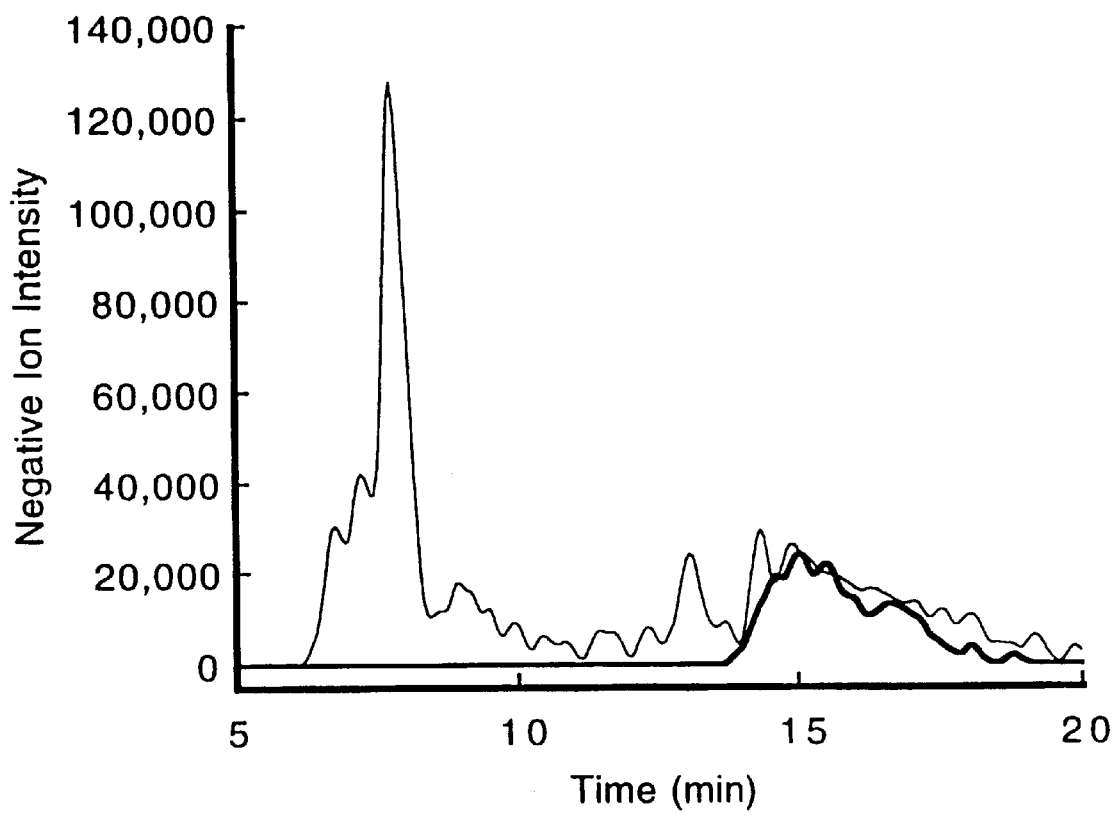
FIG. 9 shows the elution of the non-nitrated (a) versus nitrated (b) rod domain peptide AQYEK from the HPLC as monitored by electrospray MS. The non-nitrated peptide eluted from the HPLC column unusually early compared to other the bulk of trypsin-derived peptides. The parent peptide was mostly present as the singly charged ion. The thin lines correspond to m/z intensity of 638 expected for the non-nitrated peptide and the thicker lines to the m/z intensity of 683 expected for the nitrated peptide.
Figure 9B:
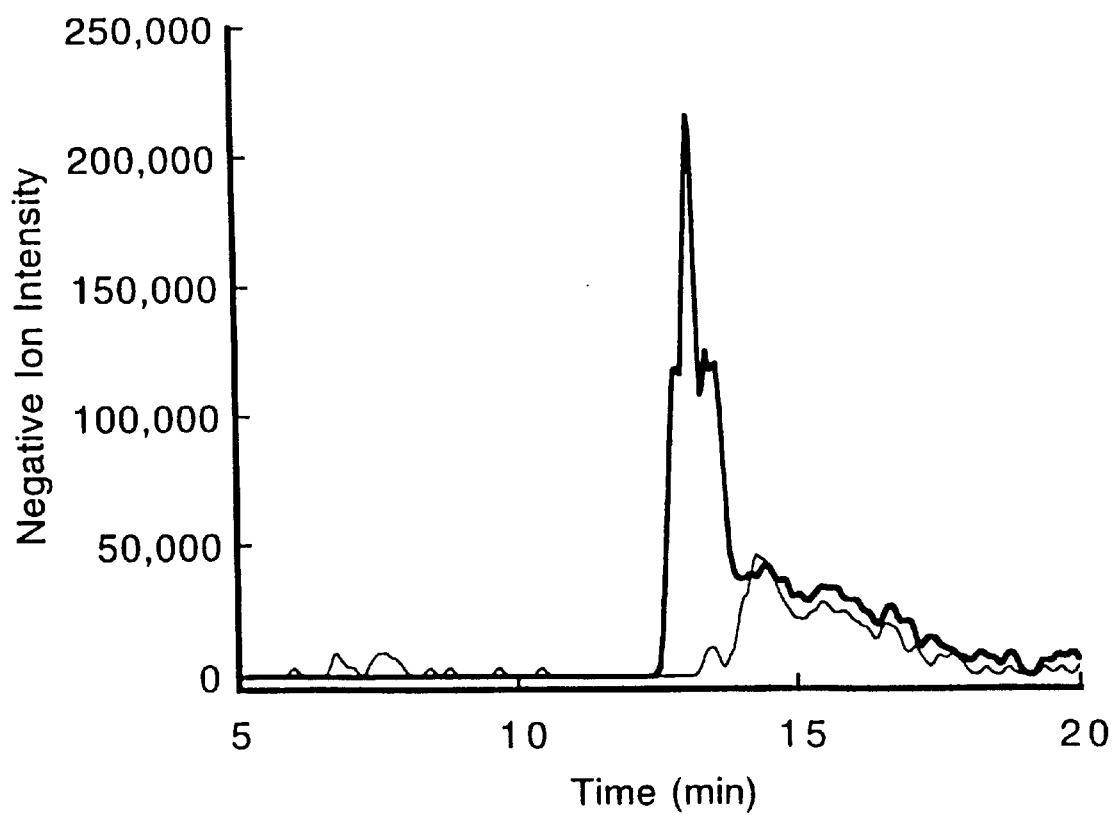

Neurofilament was treated with 3 mM peroxynitrite as described in FIG. 2 for mass spectral characterization. Electrospray mass spectrometry of trypsin-digested NF-L with approximately 6 nitrotyrosines modified per subunit revealed nitration on tyrosine 17 of the peptide YQETPR in the head region (FIG. 6) and on three tyrosine-containing peptides in the rod domain. These are tyrosine 138 in the peptide ALYEQEIR (FIG. 7), tyrosine 177 in the peptide YEEEVLSR (FIG. 8), and tyrosine 265 in the peptide AQ YEK (FIG. 9). The nitrated peptides characteristically eluted 10–40 seconds later than the non-nitrated parent peptide from the HPLC. However, the non-nitrated peptide AQYEK eluted unusually early from the HPLC column. These peptides were initially identified by searching for ions with a mass increase of 45 over the predicted masses for tyrosine-containing peptides. Two of the peptides had tyrosines on the N-terminus and were largely present as single rather than double-charged ions expected from trypsin-digested proteins. The aromatic hydroxyl group of tyrosine is known to hydrogen bond to the free amino group, which may account for the unexpectedly large fraction of the single-charged ions for these peaks. The equivalent nitrated peptide was also largely present as the singly-charged ion.

Figure 10A:
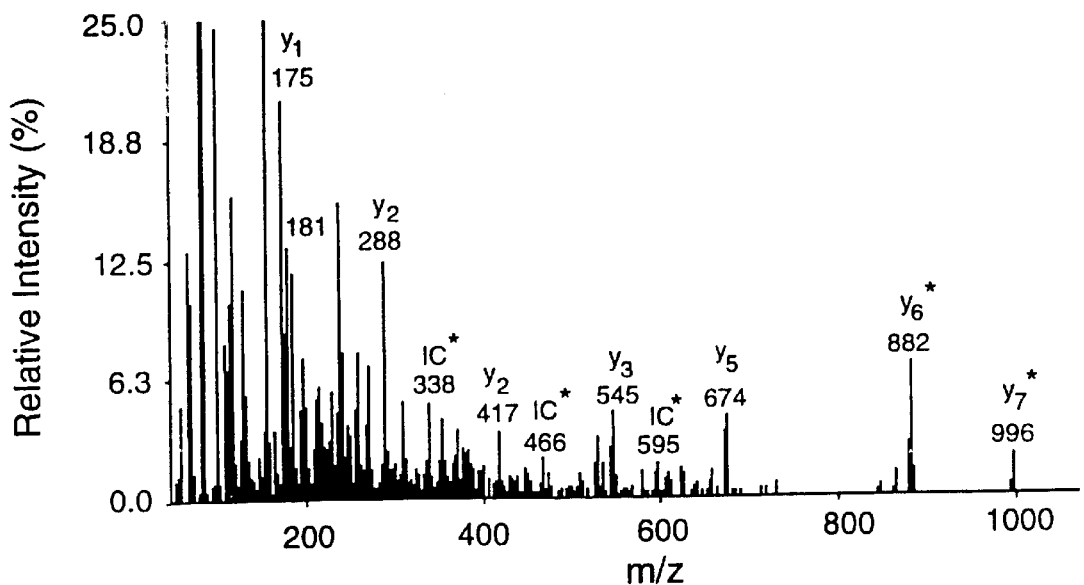
FIG. 10 shows a representative sample of the MS/MS spectrum resulting from the collision-induced fragmentation of nitrated peptide ALYEQEIR. The spectrum for nitrated peptide is shown in panel A and for the non-nitrated peptide is shown in panel B. Asterisks identify nitrotyrosine-containing fragments in panel A. Internal cleavage occurred at the N-terminal side of the tyrosine to form an immonium ion seen at 181 m/z in the nitrated spectrum A.
Figure 10B:
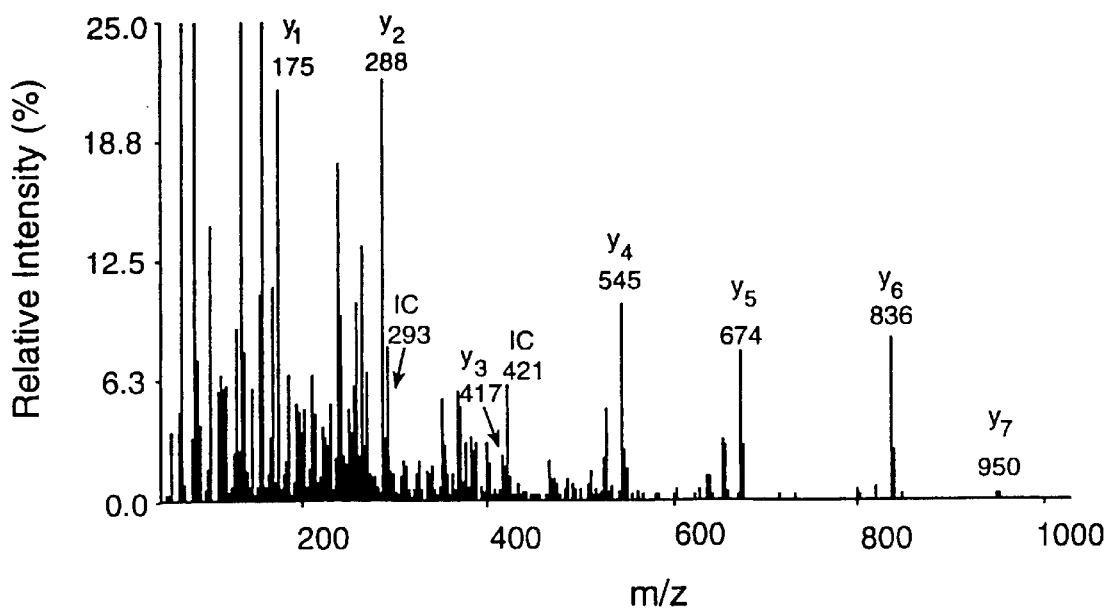

The presence of nitrotyrosine on each of these peptides was unambiguously identified by collision-induced fragmentation of individual peptides using tandem mass spectrometry (FIG. 10). Trypsin cleaves principally after the C-terminus of positively charged amino acids, allowing both the amino and carboxy terminal fragments of the peptides to be detected after random cleavages of the peptide bonds. From the masses of the fragments, the starting peptide sequence can generally be deduced. The presence of a nitro group increases the mass of tyrosine-containing fragments by 45. A small fraction of the tyrosine moiety also fragments to yield an immonium ion of 136 m/z. In nitrotyrosine-containing peptides, the 136 m/z peak was replaced by a new peak at 181 m/z, consistent with the addition of a nitro group of mass 45 to the tyrosine fraction (FIG. 10). The additional fragments further supported the assignment of the mass peptides.

Four positions of six tyrosines were identified as vulnerable to nitration. Several nitrotyrosine-containing trypsin fragments may have been too large to be detected by the mass spectrometer. Other proteases can be used to identify additional modified tyrosines. Although the unmodified parent peptides corresponding to tyrosines 5, 8, 12, 39, 41 in the head domain and tyrosines 265, 368, 372 or 389 in the rod region could be detected, no evidence of nitration on these peptides was found. In the rod domain, only one tyrosine in the linker 12 region could not be identified. To reduce interference from contaminating superoxide dismutase-derived peptides, superoxide dismutase was not added during the nitration of NF-L for these mass spectral experiments. In other experiments, all four nitrated peptides in NF-L exposed to superoxide dismutase plus NF-L were identified and no other nitrated peptides were identified.

EXAMPLE 7
Nitration Inhibits Neurofilament Assembly

Figure 11A:
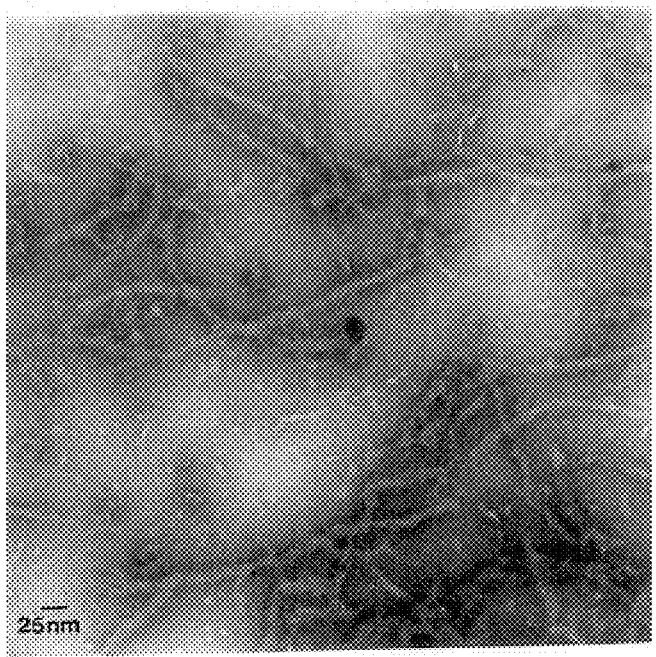
FIG. 11A shows that partially purified triplet neurofilament subunits from bovine spinal cord reassembled to form filamentous structures when dialyzed under standard assembly conditions.
Figure 11B:
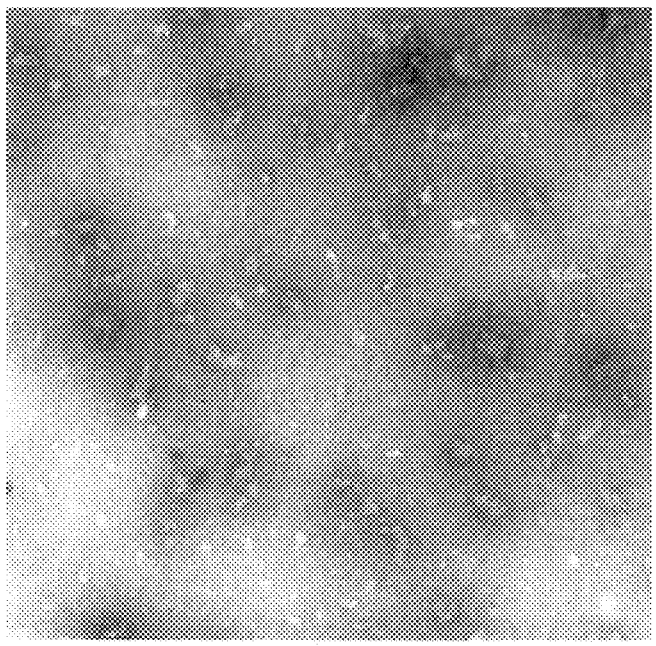
FIG. 11B shows that neurofilament subunits only formed small aggregrates when peroxynitrite-treated neurofilaments were mixed with untreated triplet neurofilaments and incubated under identical assembly conditions used in FIG. 11A.

Treatment of neurofilament preparations from bovine spinal cord with peroxynitrite inhibits filament formation from untreated subunits. Triplet neurofilament preparations containing NF-L, -M, and -H from bovine spinal cord formed filaments when incubated under standard assembly conditions (FIG. 11a), but only formed short aggregates following exposure of only a fraction of the total protein to peroxynitrite (FIG. 11b). Assembly of untreated neurofilament subunits was inhibited by addition of one part nitrated neurofilament to 3 parts of untreated subunits—conditions in which nitrotyrosine constituted <1% of total tyrosine. Partial inhibition of homologous NF-L assembly was seen with as little as 0.04% nitration of total tyrosine or less than 1 nitrotyrosine per 10 NF-L subunits. Decomposed peroxynitrite had no effect on assembly.

Neurofilament-L, a major structural protein important to the survival of motor neurons, is unusually sensitive to superoxide dismutase-catalyzed tyrosine nitration and is one of the predominant proteins to be nitrated in brain homogenates following exposure to peroxynitrite in the presence of superoxide dismutase (FIG. 5). Neurofilaments are susceptible to nitration in part because they are among the most abundant proteins in a cell and in part because they contain a large molar fraction of tyrosines. Tyrosines in structural proteins are involved in stabilizing hydrophobic contacts between subunits and become exposed to solvent when subunits are disassembled, making them more accessible to nitration by peroxynitrite plus superoxide dismutase. In addition, the mass spectral experiments suggest that the presence of a neighboring glutamate may also increase the susceptibility of specific tyrosines in neurofilaments to nitration. Consequently, neurofilaments may be major targets for superoxide dismutase-catalyzed nitration in motor neurons.

Peroxynitrite can nitrate tyrosines in purified proteins in simple solutions without superoxide dismutase present as a catalyst, but non-catalyzed nitration involves a highly reactive form of peroxynitrite which reacts with a wide range of biological molecules (Beckman et al., 1992, Koppenol et al., 1992). Consequently, the non-superoxide dismutase dependent nitration is greatly diminished in the presence of biological materials commonly found in a cell. Addition of physiological levels of glucose can decrease non-catalyzed nitration 2.5-fold, but have no effect upon superoxide dismutase-catalyzed nitration by peroxynitrite (Ischiropoulos et al., 1992a). Tris reduced the non-catalyzed nitration of NF-L but had little effect on superoxide dismutase-catalyzed nitration of NF-L (FIG. 4). The addition of low molecular weight alternative targets for peroxynitrite in effect mimics what happens in vivo, where all the biological molecules present in brain and spinal cord homogenates will compete for reaction with peroxynitrite. When peroxynitrite is added to brain or spinal cord homogenate, only a few proteins such as NF-L were susceptible to nitration and superoxide dismutase selectively enhanced the nitration of these proteins (FIG. 5).

The functional consequences of adding a nitro group to tyrosine can be substantial. The nitro group is bulky, potentially causing steric interference when one structural protein subunit attempts to assemble with a neighbor (Beckman and Koppenol, 1996). In addition, nitration reduces the $pK_a$ of the phenolic hydroxyl group to about 7.5, making the hydrophobic tyrosine partially negatively charged and more hydrophilic. Because tyrosines involved in subunit interactions in a structural protein make intimate contacts with residues on neighboring subunits, nitration of tyrosines would be expected to interfere with subunit association needed for assembly of a complete functional structure. The addition of nitrated neurofilament subunits to untreated neurofilaments can completely disrupt assembly (FIG. 11). One can reasonably expect that incorporation of only a few nitrated subunits into a growing filament can have major consequences on the overall assembly of neurofilaments (Beckman and Koppenol, 1996).

The four nitrated tyrosines identified by mass spectroscopy occur at positions known to be involved in making intersubunit contacts. The head region is involved in lateral contacts with other protofilaments (Heins et al., 1993). The nitrated tyrosine at position 17 is adjacent to two highly conserved arginines known to be important for the assembly of intermediate filaments in general (Fuchs and Weber, 1994). Microinjection of 50-fold molar excess of a synthetic peptide with this sequence has been shown to prevent the assembly of the intermediate filament, vimentin. The other three nitrated tyrosines were in the coiled coil of the rod domain. Two nitrated tyrosines in the NF-L rod are located in the coils 1B and 2A of the rod domain respectively. The coiled coil structure of the rod domain in NF-L is interrupted by three short linker regions and the third nitrated tyrosine in the peptide ALYEQEIR is at the C-terminus of the first linker region in NF-L. Coiled coils are stabilized by hydrophobic residues like tyrosine packing together between the two helixes of separate peptide chains. The sequences of coiled coils have a characteristic seven amino acid periodicity of abcdefg where the first and fourth residues are hydrophobic and the others are hydrophilic. The hydrophobic residues pack in a knob-into-hole arrangement where the holes are formed by the side-chains of the opposite chain.

Figure 12:
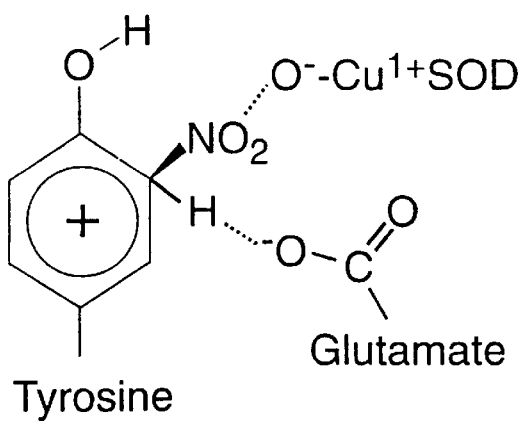
FIG. 12 shows one potential scheme for how glutamate could enhance nitration by stabilizing the carbonium ion intermediate formed when the complex of superoxide dismutase plus peroxynitrite nitrates NF-L.

The sequences in NF-L containing nitrotyrosine in the rod domain all have a C-terminal glutamate, which may contribute to their susceptibility to nitration. In coiled coils, the side chains tend to be angled towards the amino terminus (Lupas, 1996), which will bring the carboxyl group of the glutamate into close proximity of the tyrosine. The negative charge of the carboxyl group may help stabilize a carbonium ion intermediate formed when the peroxynitrite-superoxide dismutase complex attacks NF-L (FIG. 12). A glutamate adjacent to tyrosine has been identified as being susceptible to nitration in bovine superoxide dismutase (Ischiropoulos et al., 1992b, Smith et al., 1992). Nitration might also be enhanced by the glutamate reducing the $pK_a$ of the tyrosine or possibly by forming an nitronium-carboxylate intermediate which participates in nitration (Ischiropoulos et al., 1992b). Although aspartate is also an acidic amino acid like glutamate and could enhance nitration, aspartate may be less effective at enhancing tyrosine nitration because its shorter side chain substantially decreases its flexibility and access to tyrosine.

Neurofilaments are strongly implicated the pathogenesis of ALS. Axonal swellings and accumulations of phosphorylated neurofilament subunits in the perikarya of motor neurons are commonly observed among the earliest signs of injury in ALS (Carpenter, 1968, Itoh et al., 1992). Abnormal aggregates of neurofilaments are also observed in some strains of transgenic mice over-expressing superoxide dismutase mutations (Dal Canto and Gurney, 1995), but not in others. Abe et al. (1995) reported nitrotyrosine immunolocalized in regions of abnormal neurofilament accumulations in three sporadic ALS patients. Chou (1996a,b) have found nitrotyrosine, superoxide dismutase and neuronal nitric oxide synthase colocalized in conglomerates of neurofilaments in both upper and lower motor neurons of sporadic ALS patients.

EXAMPLE 8

Expression and Purification of Superoxide Dismutase Mutants

Molecular biology grades of potassium phosphate, sodium chloride, guanidine-HCl, and urea as well as atomic absorption standard solutions of zinc and copper were obtained from Fisher. Unless specified otherwise, reagents were obtained from Sigma. The ALS-superoxide dismutase mutations were created by a two cycle, polymerase chain reaction-based mutagenesis protocol described by Zhao et al (Zhao et al. 1993) using mutagenic primers to introduce the desired mutants. Primers for the 5' and 3' ends of the superoxide dismutase gene were chosen to introduce Nco1 and BamH1 restriction sites, which were then used for cloning into a pET-3d expression system (Novagen, Madison, Wis.). The mutagenesis was confirmed by complete sequencing of the superoxide dismutase inserts. The superoxide dismutase mutants were expressed in E. coli strain BL21$_{(DE3)}$plysS. Bacteria were grown in Luria broth supplemented with 1 mM IPTG beginning at an $OD_{600\ nm}$ reading of 0.6; $ZnCl_2$ (0.1 mM) and $CuCl_2$ (0.05 mM) were also added to the medium at this time. Induction was performed at 23° C. for 3 hr. Bacteria were harvested by centrifugation (4000×g for 10 min at 4° C.), resuspended in 20 mM Tris-HCl at pH 7.8, and frozen overnight. Following freeze/thaw lysis, solutions were sonicated, treated with 0.05% polyethyleneimide to remove DNA, and centrifuged at 18,000×g. Supernatants were loaded onto and eluted from a DEAE Sephacel column with a gradient of 0 to 200 mM NaCl in 20 mM Tris, pH 8.0. Based on protein content of column fractions having superoxide dismutase activity (as determined by the cytochrome c reduction method (McCord et al. 1969), a 10% molar excess of copper sulfate and zinc sulfate was added followed by incubation at 4° C. for 1 hour. Final purification was by HPLC-strong anion exchange chromatography eluted using a 0 to 0.25 M NaCl gradient in 10 mM Tris, pH 8.0. Superoxide dismutase activities of column fractions were determined and specific activity calculations were based on protein values determined with an enhanced BCA assay (Pierce) at 60° C. using human wild-type superoxide dismutase as a standard, which was previously standardized by amino acid analysis. Metal content was determined using the PAR assay in 6 M guanidine-HCl; non-specifically bound trace metals were quantified by PAR assay in the absence of denaturant. Pure superoxide dismutases (32 kD dimer) were concentrated to 25–50 mg/ml using ultrafiltration (10,000 MWCO), fast frozen, and stored at −80° C. until use.

EXAMPLE 9
Expression and Purification of Recombinant Mouse NFL

Mouse NF-L cDNA from Dr. Don Cleveland (University of California, San Diego), was subcloned into the pET-3d expression system (Novagen) and transfected into host E. coli (BL21$_{(DE3)}$plysS). Bacteria were grown in Luria broth supplemented with 1 mM IPTG beginning at an $OD_{600\ nm}$ reading of 0.8. Induction was at 37° C. for 4 hours. Bacteria were harvested by centrifugation (4000×g for 10 min at 4° C.), resuspended in lysis buffer (25% sucrose, 1 mM EDTA, and 50 mM Tris, pH 8.) and frozen overnight at −80° C. Solutions were thawed at 37° C., DNAse I was added along with 1 μM $MnCl_2$ and 10 μM $MgCl_2$ and incubated for 30 min at 23° C. The cell extract was washed with detergent I (200 mM NaCl, 1% deoxycholate, 1% NP-40, 2 mM EDTA, and 20 mM Tris, pH 7.5) and the mixture was swirled and placed on ice for 10 min. Following centrifugation at 7000×g for 15 min at 4° C., the precipitate was washed with 0.4% Triton X-100 containing 1 mM EDTA three times. The supernatant was decanted and the pellet was dissolved in 50 mM Tris, pH 7.8 containing 6 M urea, 2 mM DTT, 0.1 mM PMSF, and 1 mM EGTA and frozen at −80° C. until use.

EXAMPLE 10
Preparation of apo-metallothionein

Metals were removed from type II rabbit liver metallothionein (Sigma Chemical) by ultrafiltration (3,000 MWCO)×4 in 10 mM phosphate buffer, pH 2.0 at 4° C. Complete removal of metals was confirmed by periodic assessment of the metallothionein ultra-retentate via the PAR/guanidine-HCl assay described below. Metallothionein binds metals via its numerous cysteine residues which are prone to auto-oxidation in the apo-protein. Thus, solutions of apo-metallothionein were deoxygenated by gentle argon bubbling and frozen at −80° C. until use. Reduced sulfhydryl content of apo-metallothionein was determined before each use by reaction with 0.6 mM 5,5'-dithiobis-(2-nitrobenzoic acid) (DTNB or Ellman's reagent) in 0.1 M sodium borate containing 6 M guanidine-HCl, pH 7.8. The extinction coefficient was determined by standardization with reduced glutathione ($\epsilon_{420\ nm}$=13,200 $M^{-1}cm^{-1}$).

EXAMPLE 11
Preparation of apo-superoxide Dismutase Proteins and Selectively Metal-restored Forms Purified superoxide dismutase proteins were dialyzed against 50 mM sodium acetate buffer, pH 3.8 containing 5 mM EDTA at 4° C. for 24 hr to remove metals followed by extensive dialysis against 25 mM sodium acetate containing 50 mM NaCl to remove EDTA. The final dialysis step consisted of 10 mM acetate, pH 3.8 and the apo enzymes were maintained in this solution at 4° C. and used within a few hours. Copper-only superoxide dismutase was prepared by adding a 10% molar excess of copper sulfate to apo superoxide dismutase in acetate buffer at pH 3.8 followed by 1 hr incubation and then dialysis against 10 mM KPi, pH 7.4 containing 100 mM NaCl at 4° C. overnight; final dialysis was against 10 mM KPi, pH 7.4 at 4° C. Following dialysis, protein content was determined by the enhanced BCA assay (Pierce) and metal content was determined.

EXAMPLE 12
PAR Chelation Assay for Zinc and Copper Content

Figure 13:
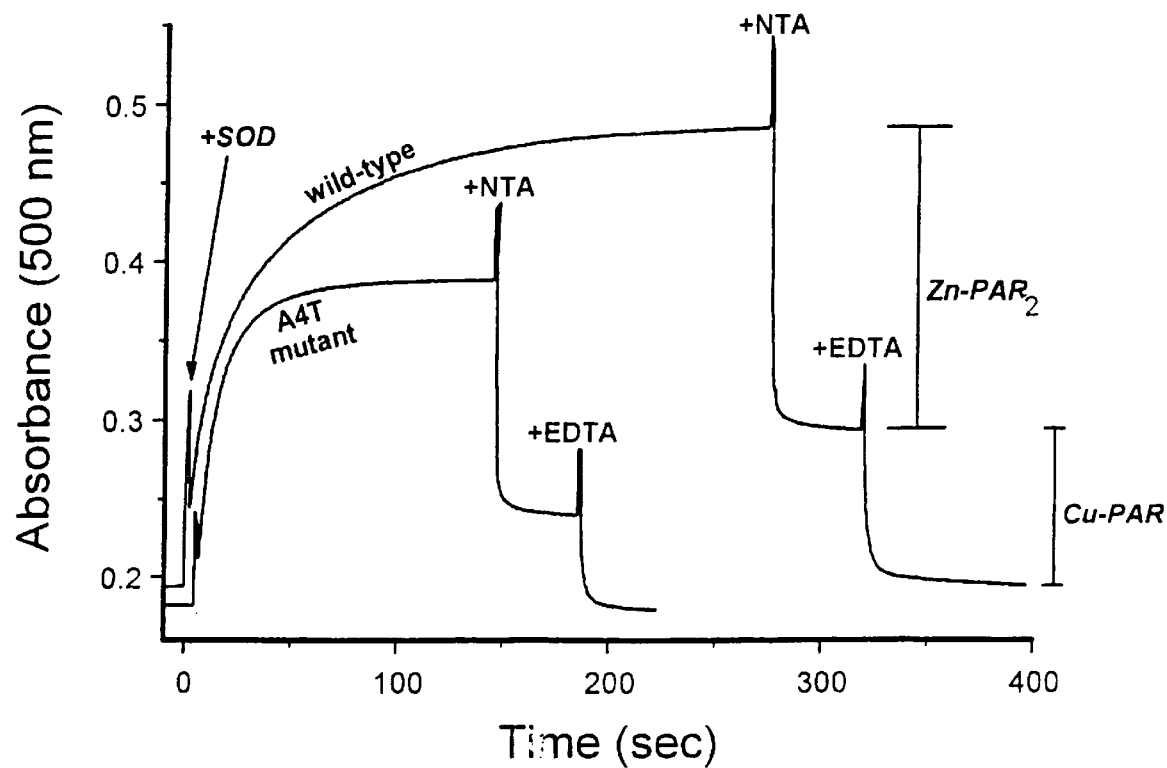
FIG. 13 shows the metal release from wild-type superoxide dismutase and mutant A4T. HPLC-purified wild-type (63 $\mu$g) or A4T mutant (49 $\mu$g) superoxide dismutase was added to a 1.4 ml reaction solution containing 6 M guanidine-HCl and 100 $\mu$M pyridylazoresorcinol (PAR) in 0.1 M sodium borate, pH 9.1. At the times indicated, nitrilotriacetic acid (NTA) was added (0.8 mM) to remove Zn from the Zn-PAR$_2$ complex followed by EDTA (0.8 mM) to remove Cu from the Cu-PAR complex. Rapid spikes in absorbance resulted from sample addition. The concentrations of Zn present in the superoxide dismutases was determined by the ($Abs_{500\ nm}$ following NTA addition and Cu was determined by the ($Abs_{500\ nm}$ following EDTA addition.

Superoxide dismutase metal content was determined by adding known amounts of protein (15–75 μg) to a stirred 3 ml cuvette at 37° C. containing 100 μM 4-pyridylazoresorcinol (PAR) and 6 M guanidine-HCl in 1.4 ml of 100 mM sodium borate, pH 9.1 (FIG. 13) giving a final pH of 7.8 as measured by a standard pH electrode. PAR has a low intrinsic absorbance at 500 nm which increases dramatically upon binding zinc or copper. Extinction coefficients for the Zn-$PAR_2$ and Cu-PAR complexes under these conditions were determined experimentally by titrating with atomic absorption standard solutions of zinc and copper; the $\Delta Abs_{500\ nm}$ extinction coefficients for the Zn-$PAR_2$ and Cu-PAR complexes was determined to be 69,200 $M^{-1}cm^{-1}$ and 36,300 $M^{-1}cm^{-1}$, respectively. Extinction coefficients were sensitive to small changes in pH and standard curves were prepared daily. When superoxide dismutase was added to the solution of PAR and guanidine-HCl in sodium borate, the absorbance at 500 nm increased as zinc and copper, released from denaturing superoxide dismutase, formed complexes with PAR (FIG. 13). When the total absorbance no longer increased (~1–4 min, depending on the particular protein), the absorbance related to the Zn-$PAR_2$ complex was then determined by addition of 0.8 mM nitrilotriacetic acid (NTA). NTA selectively chelates zinc from Zn-$PAR_2$ but cannot remove copper from the higher affinity Cu-PAR complex. When the decrease in absorbance following NTA ceased (~20–30 s), 0.8 mM EDTA was added to chelate copper from Cu-PAR. The change in absorbance following NTA addition corresponded to the total Zn-$PAR_2$ complex whereas the change following EDTA corresponded to the total Cu-PAR complex. Zinc and copper which was non-specifically bound or present as trace contaminants in buffers was quantified by assaying proteins in 100 mM KPi, pH 7.4 in the absence of guanidine-HCl. In the absence of guanidine-HCl, the concentration of $Zn-PAR_2$ was determined by the change in absorbance following NTA $\epsilon_{500\ nm}=56,700\ M^{-1}cm^{-1}$ and the concentration of Cu-PAR determined $\epsilon_{500\ nm}=37,000\ M^{-1}cm^{-1}$ following EDTA addition. Results obtained using this assay were verified by atomic absorption.

EXAMPLE 13
Determination of Binding Constants for $Zn-PAR_2$ and Cu-PAR

In order to determine affinity constants by competition assay, the stability constants for the metal complexes of the competing chelator must be known. In this case, reliable literature values for the $Zn-PAR_2$ and Cu-PAR complexes under conditions used here were not available whereas values for Zn-NTA and Cu-EDTA are well known. Thus, the affinity of PAR for zinc and copper was determined by competition with NTA and EDTA, respectively. Stoichiometry determinations revealed that PAR and zinc formed 2:1 complexes so long as PAR was in at least a 2.5-fold molar excess over zinc. PAR and copper formed a 1:1 complex. Affinity of the $Zn-PAR_2$ complex was determined by titrating PAR (100 and 500 $\mu M$) plus 10 $\mu M$ zinc with NTA, measuring the amount of $Zn-PAR_2$ complex spectrally ($\epsilon_{500\ nm}=56,700\ M^{-1}cm^{-1}$) at different NTA concentrations and calculating the amounts of Zn-NTA, free PAR, and free NTA. These values were then used to calculate $K_{d\ Zn-PAR2}$ using equations 1 and the dissociation constant for the Zn-NTA complex ($3.98\times10^{-11}\ M^{-1}$) (Dawson et al. 1989). Similarly, solutions of 100 and 500 $\mu M$ PAR plus 10 $\mu M$ copper was titrated with EDTA and values for Cu-PAR ($\epsilon_{500\ nm}=37,000\ M^{-1}cm^{-1}$), Cu-EDTA, free PAR, and free EDTA were entered into equation 2 together with the dissociation constant for the Cu-EDTA complex ($1.26\times10^{-16}\ M^{-1}$) (Dawson et al. 1989) to calculate $K_{d\ Cu-PAR}$.

$$K_{d\ Zn-PAR2}=[PAR][Zn-NTA]/[Zn-PAR_2][NTA_{free}]\times K_{d\ Zn-NTA} \quad \text{Eqn. 1}$$

and $$K_{d\ Cu-PAR}=[PAR][Cu-EDTA]/[Cu-PAR][EDTA_{free}]\times K_{d\ Cu-EGTA} \quad \text{Eqn. 2}$$

Under the specific conditions used here, dissociation constants for $Zn-PAR_2$ and Cu-PAR complexes were found to be $7.7\times10^{-11}\ M^{-1}$ and $2.6\times10^{-15}\ M^{-1}$, respectively.

EXAMPLE 14
Determination of Zinc and Copper Release Rates and Binding Affinities with Superoxide Dismutases Total metal content of the superoxide dismutase incubation solutions was determined both at time zero and again at the end of each incubation by PAR assay in guanidine-HCl as described above. Concentrations of $Zn-PAR_2$ and Cu-PAR were determined at the times indicated in FIG. 2, plotted as a function of time, and fitted to equation 3 which describes a single exponential change from an initial metal-PAR concentration ($A_o$) to a final or equilibrium metal-PAR concentration ($A_f$) at a rate of $k_1$. The half-life ($t_{1/2}$) for metal release shown in Table I was calculated as $\ln(2)k_1$.

$$A_o+A_f(1-e^{(-k1t)}) \quad \text{Eqn. 3}$$

Because all zinc and copper originates from the superoxide dismutases, equilibrium concentrations of metal-deficient superoxide dismutases (superoxide dismutase$_{Zn-}$, superoxide dismutase$_{Cu-}$) were equivalent to the equilibrium concentrations of $Zn-PAR_2$ and Cu-PAR obtained from equation 3 ($A_f$ values). Equilibrium concentrations of zinc-containing ([Zn-superoxide dismutase]) and copper-containing superoxide dismutase ([Cu-superoxide dismutase]) were determined by subtracting the equilibrium concentrations of $Zn-PAR_2$ and Cu-PAR from the total superoxide dismutase protein present. These values were entered into equations 4 and 5 to calculate affinity constants for zinc and copper binding to superoxide dismutases ($K_{d\ Zn-superoxide\ dismutase}$, $K_{d\ Cu-superoxide\ dismutase}$).

$$K_{d\ Zn-superoxide\ dismutase}=[\text{superoxide dismutase}_{Zn-}][Zn-PAR_2]/[Zn\text{-superoxide dismutase}][PAR]\times K_{d\ Zn-PAR2} \quad \text{Eqn. 4}$$

and $$K_{d\ Cu-superoxide\ dismutase}=[\text{superoxide dismutase}_{Cu-}][Cu-PAR]/[Cu\text{-superoxide dismutase}][PAR]\times K_{d\ Cu-PAR} \quad \text{Eqn. 5}$$

The concentration of free PAR ([PAR]) was determined by subtracting the measured amounts of $Zn-PAR_2$ and Cu-PAR from the total PAR added. The estimated dissociation constants for superoxide dismutase do not account for any cooperative interactions which may exist between the zinc and copper binding sites or between subunits in the enzyme dimer.

Calculations of metal-binding affinities were based on direct measurements of the relative amounts of metals present as the metal-PAR and metal-superoxide dismutase complexes following establishment of an equilibrium in 2 M urea. Two molar urea was used here because it reversibly accellerated metal loss from superoxide dismutase without denaturing the superoxide dismutase proteins—conditions essential for equilibrium-based determinations of affinity constants. An earlier attempt to establish a metal equilibrium between bovine Cu,Zn superoxide dismutase and 2-pyridinecarboxylate at pH 6.25 extended over 14 days and the ability of the apo protein to be reconstituted was not determined (Hirose et al. 1984). Initially, incubation of superoxide dismutases with PAR were carried out under native conditions for 72 hours. The ratio of zinc loss to copper loss from superoxide dismutase under these conditions was even higher than in 2 M urea. However, maximum amounts of metal released after 72 hours, as a percentage of total metals present, were too low to accurately calculate binding affinities. Thus, 2 M urea was used to expedite establishment of a metal-protein/metal-PAR equilibrium. Two molar urea represents only a mild stress for superoxide dismutase as wild-type enzyme retains full enzyme activity for days in 8 M urea (Forman et al. 1973b). All enzymes were found to be retain full dismutase activity and remain capable of rebinding metals after 72 hours in 2 M urea.

Figure 14A:
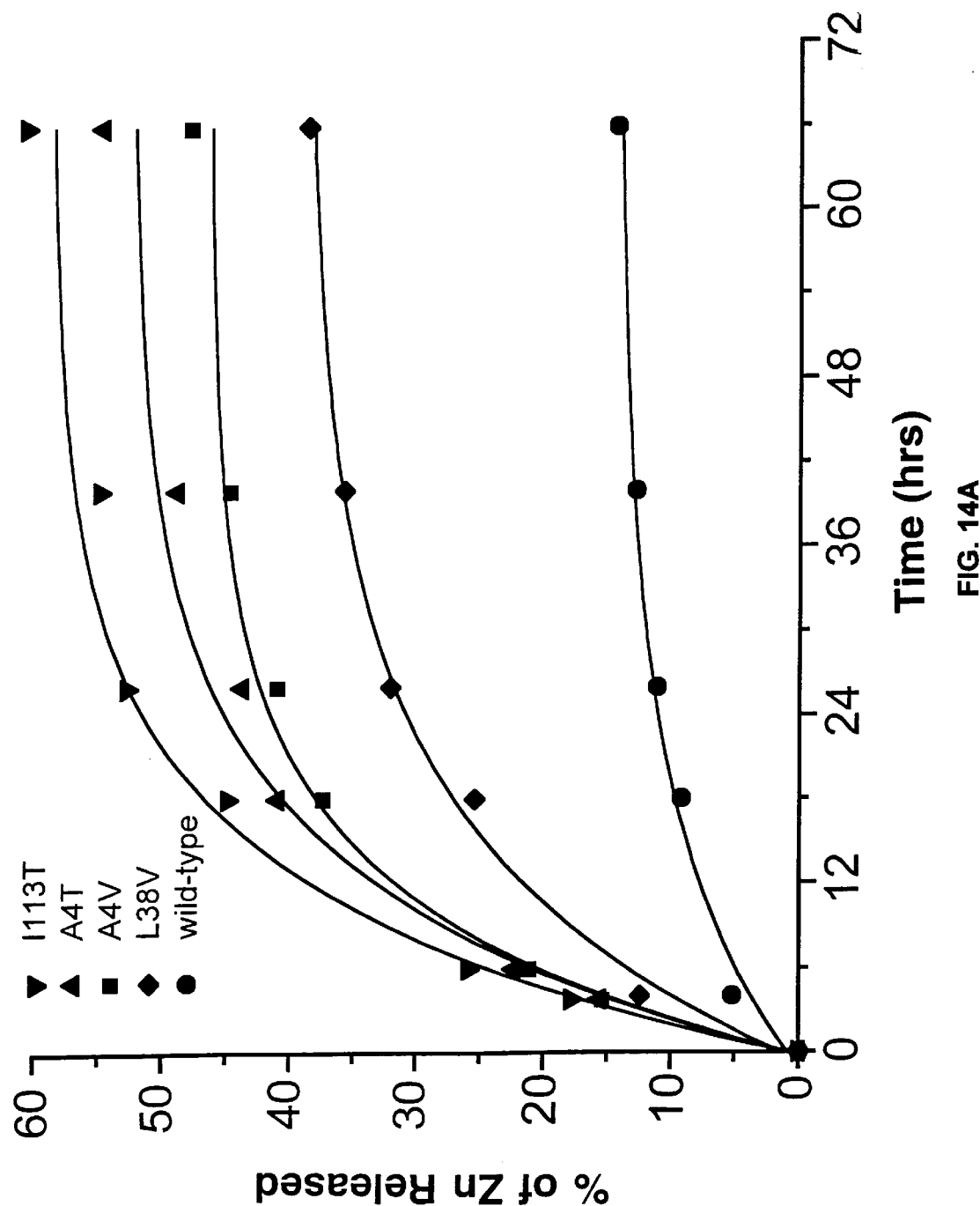
FIG. 14 shows the a) zinc and b) copper loss from mutants and wild-type superoxide dismutase. HPLC-purified superoxide dismutase mutants and wild-type were incubated with PAR under mild denaturing conditions to expedite establishment of an equilibrium between metal-PAR and metal-superoxide dismutase. Solutions (0.4 ml) containing 2 mg/ml superoxide dismutase, 1.9 mM PAR, and 2 M urea, in 100 mM potassium phosphate, pH 7.4, were incubated at 37° C. for 66 hours. The total amount of copper and zinc present as the Zn-PAR$_2$ and Cu-PAR complexes (i.e., released from superoxide dismutases) was followed by measuring the absorbance at 500 nm following addition of 38 $\mu$l aliquots of the incubation solutions to stirred cuvettes containing 1.4 ml 100 mM potassium phosphate, pH 7.4 at 37° C. NTA (0.8 mM) was first added to remove zinc from the Zn-PAR$_2$ complex, and the zinc concentration was calculated by the decrease in absorbance at 500 nm using ($Abs_{500\ nm}$ extinction coefficients given below. The copper content was then determined by the ($Abs_{500\ nm}$ following addition of EDTA (0.8 mM). After 66 hours, excess zinc and copper were added to each superoxide dismutase solution. Superoxide dismutases were dialyzed to remove PAR-metal complexes, incubated with excess metals, dialyzed, and analyzed for total protein-bound metals by PAR assays in 6 M guanidine-HCl; enzymes were found to be fully capable of rebinding metals.
Figure 14B:
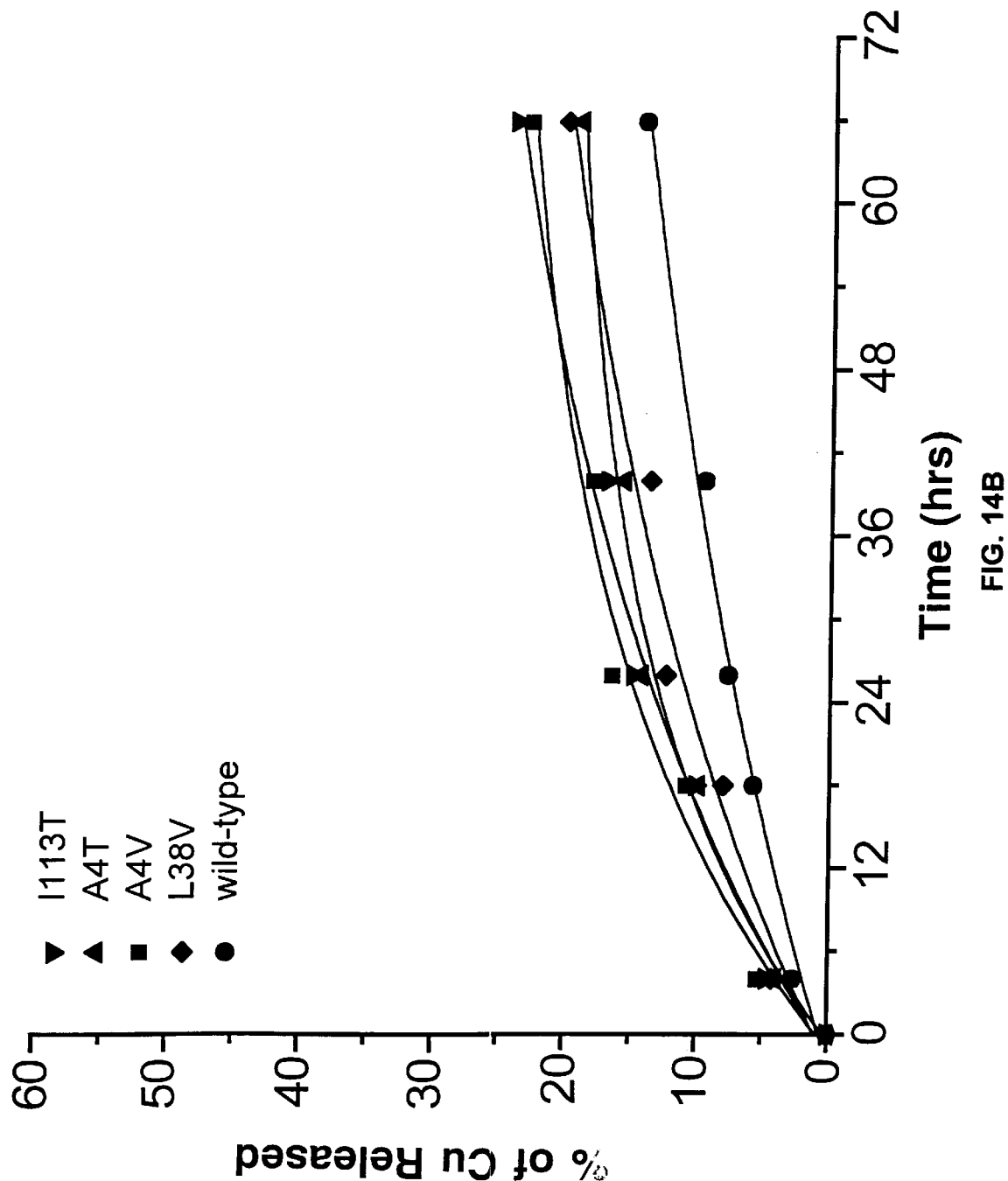

ALS-associated superoxide dismutase mutants lost zinc to a greater extent than wild-type when incubated for 66 hours (FIG. 2a), indicating that they have a lower affinity for zinc (Table I). The half-life for zinc loss ranged from 10.3 to 13.5 hours and was approximately the same for wild-type and superoxide dismutase mutants. The extent of copper loss over the same time period was considerably lower than for zinc and similar for both mutants and wild-type (FIG. 14b). The half-life for copper loss ranged from 19 to 46 hours, consistent with formation of a relatively stable zinc-deficient form followed by a gradual loss of copper.

Based on the metal partitioning between the chelator 4-pyridylazoresorcinol (PAR) and superoxide dismutase, affinity constants for zinc and copper binding to superoxide dismutase were calculated (Table I). The mutants bound zinc with affinities which ranged from 18-fold lower for mutant A4T to 30-fold lower for A4V, a mutant associated with particularly rapid disease progression (Rosen et al. 1994a). Copper binding affinities varied by a maximum of only 2.6-fold for L38V and were essentially unchanged for A4V and A4T compared to wild-type. The $K_d$ for wild-type superoxide dismutase binding copper was $6.0 \times 10^{-18}$ $M^{-1}$ and $4.2 \times 10^{-14}$ $M^{-1}$ for wild-type binding zinc. The copper $K_d$ for A4V was $9.9 \times 10^{-18}$ $M^{-1}$ and $1.3 \times 10^{-12}$ $M^{-1}$ for zinc. Thus, copper binding affinity is approximately 7,000 times higher than for zinc with wild-type enzyme and 130,000 times greater for A4V.

Figure 15A:
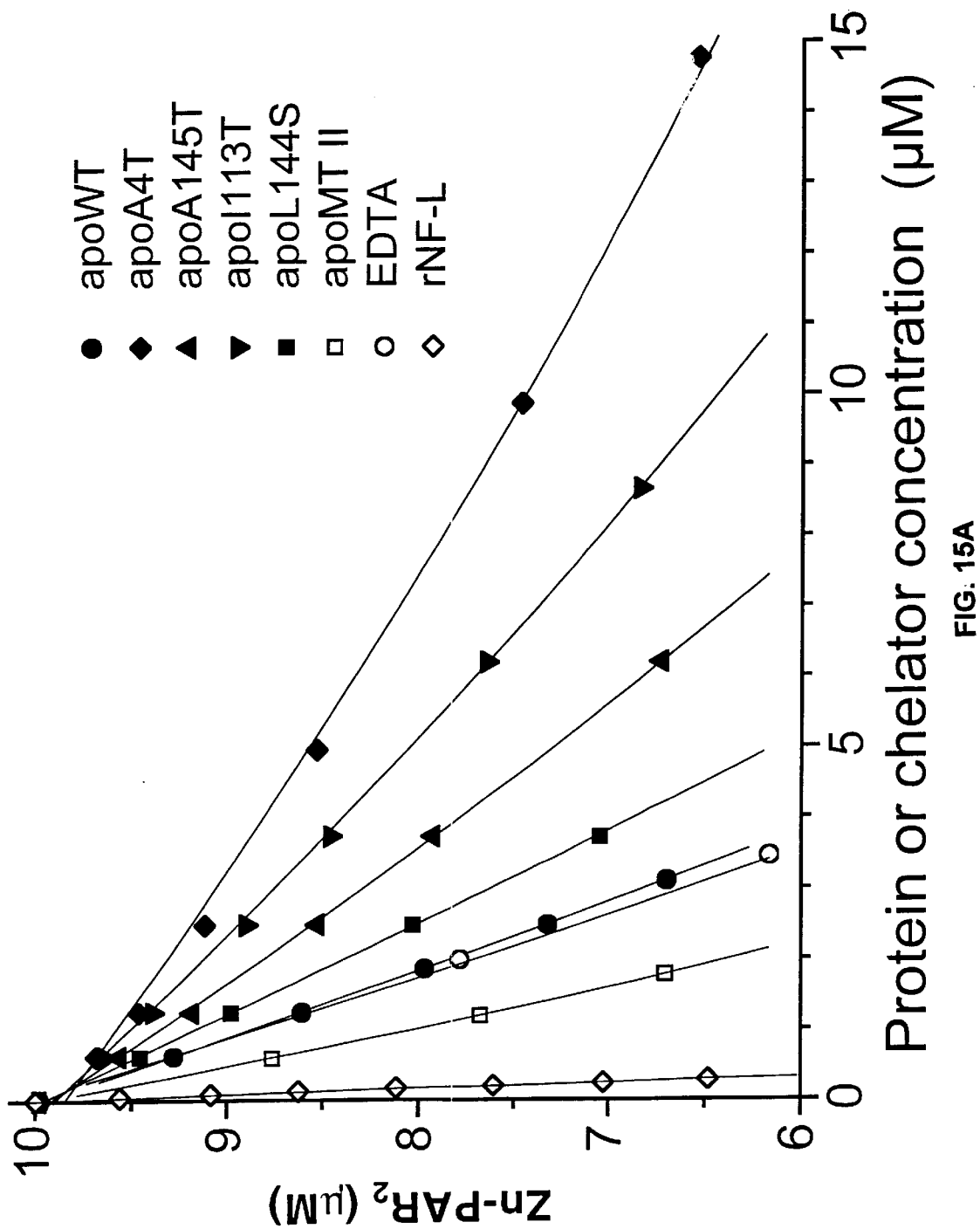
FIG. 15 shows the a) relative zinc binding affinities for superoxide dismutases and zinc binding stoichiometries for NF-L and apo metallothionein II, and b) relative copper binding by apo metallothionein II and NF-L. a) Apo proteins were prepared and added to stirred cuvettes at 37° C. containing 100 $\mu$M PAR and 10 $\mu$M zinc in 100 mM KPi, pH 7.4. The decrease in absorbance associated with loss of Zn-PAR$_2$ (($_{500\ nm}$=56,700 M$^{-1}$cm$^{-1}$) equals the amount of zinc bound by the added protein. Thus, zinc binding stoichiometries were determined by the ratios of apo proteins added to the amounts of zinc removed from Zn-PAR$_2$. The slope of the curve generated by sequential addition of protein is an index of relative binding affinity; the steeper the slope, the greater the ability to compete with PAR for zinc, and the greater the affinity. EDTA has a K$_d$ for zinc equal to 3.3×10$^{-14}$ M$^{-1}$ (Dawson et al. 1989) and was included for comparison to apo proteins. b) Apo metallothionein II and NF-L were added to a solution containing 100 $\mu$M PAR and 10 $\mu$M copper in 100 mM KPi, pH 7.4.
Figure 15B:
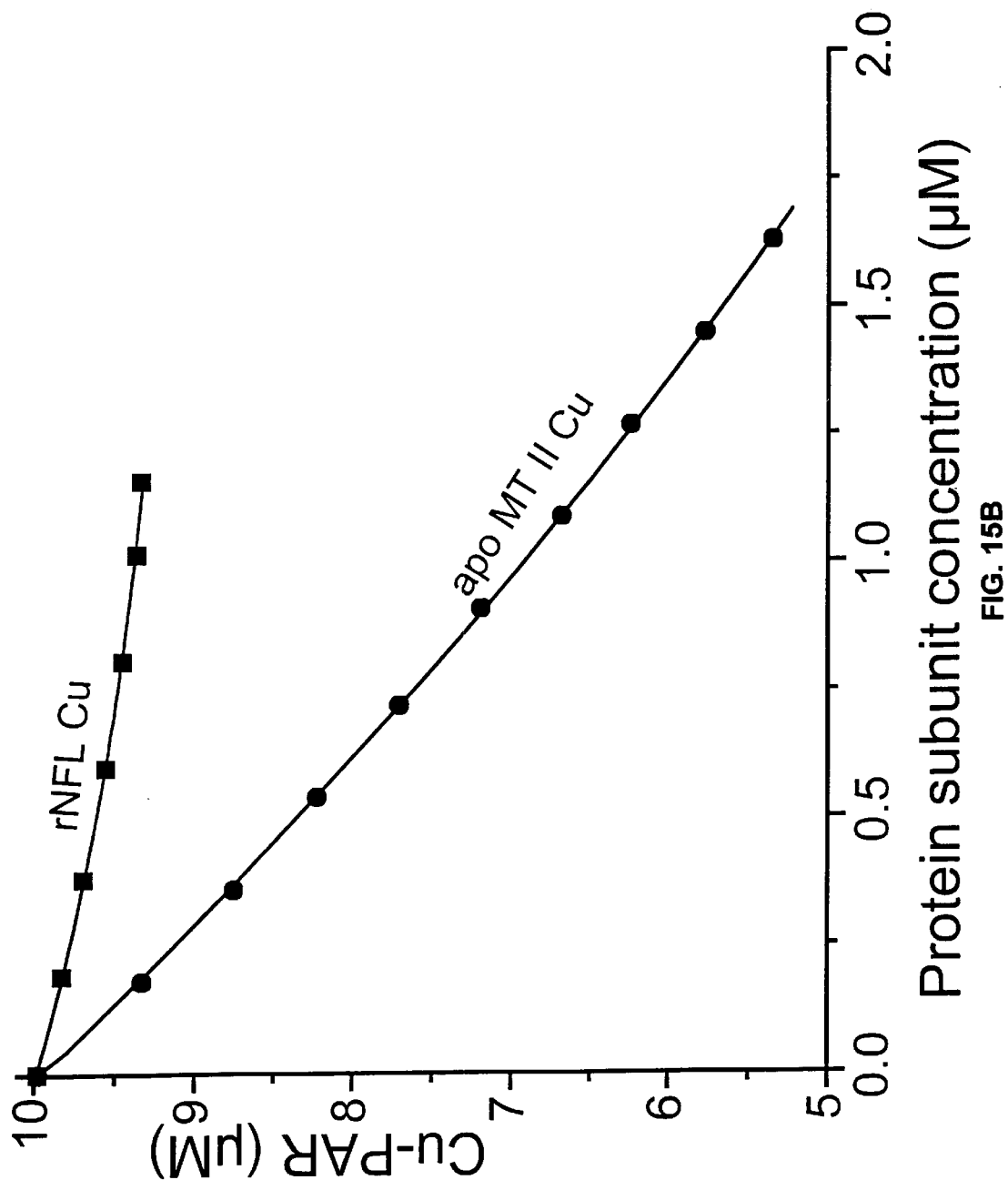

Lower zinc binding affinity is also evidenced by the decreased ability of freshly prepared apo superoxide dismutase mutants to compete with PAR for zinc (FIG. 15a). More apo mutant enzyme was required to remove zinc from the Zn-PAR$_2$ complex as compared to apo wild-type, indicating lower zinc binding affinity for the apo mutant enzymes. Apo wild-type superoxide dismutase was found to have an affinity for zinc similar to that of EDTA ($3.2 \times 10^{-14}$ $M^{-1}$) (Dawson et al. 1989). Neurofilament proteins are present in high abundance along with superoxide dismutase in motor neurons and are known to bind metals (Shen et al. 1994; Pierson et al. 1988), as is metallothionein (Shaw et al. 1991). Therefore, the relative abilities of NF-L and apo metallothionein II to compete for zinc present as Zn-PAR$_2$ were compared. Recombinant NF-L and apo metallothionein, like wild-type superoxide dismutase, stoichiometrically removed zinc from Zn-PAR$_2$, indicating that their binding affinities for zinc were at least 1000-fold greater than PAR and considerably higher than all ALS superoxide dismutase mutants. Furthermore, NF-L bound 12 zinc atoms per mole compared to two zinc atoms for apo metallothionein and one for wild-type superoxide dismutase (FIG. 15a). Similar titrations of Cu-PAR complexes revealed that NF-L competed poorly with PAR for copper while apo metallothionein II stoichiometrically bound three copper atoms per mole (FIG. 15b).

Figure 16:
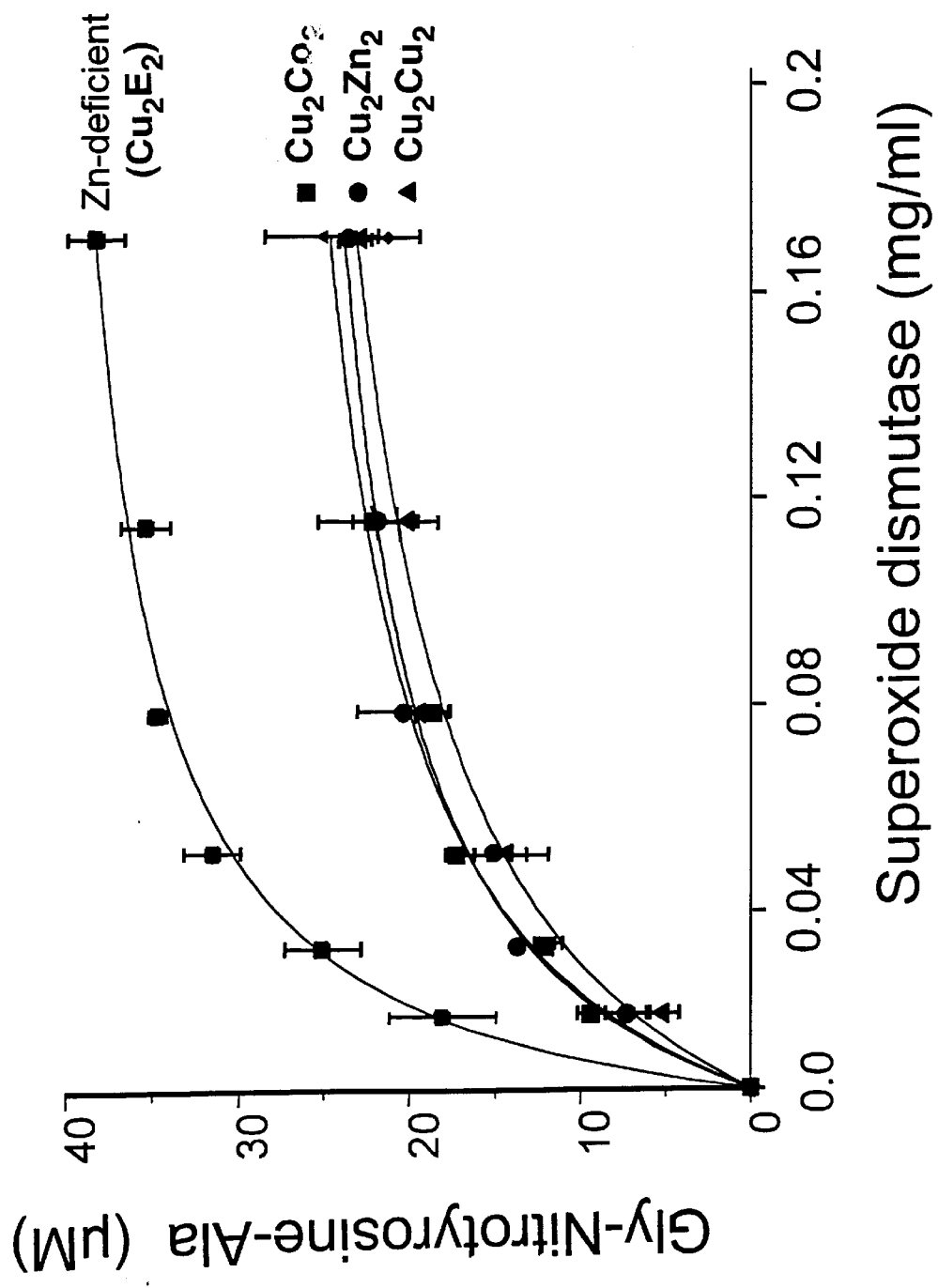
FIG. 16 shows the nitration catalysis by zinc-deficient and metal-restored superoxide dismutase. The various copper and zinc-restored or metal-substituted superoxide dismutases were prepared from apoproteins as described (Valentine, J. S. et al. 1981). Reactions were initiated by adding 1 mM peroxynitrite to solutions containing 2 mM gly-tyr-ala, 100 mM NaCl, 100 mM glucose, 0.1 mM DTPA, and metal-restored superoxide dismutase forms in 50 mM potassium phosphate, pH 7.4. Nitrotyrosine was measured spectrally at 430 nm after alkalinization ($\epsilon$=4,300 M$^{-1}$cm$^{-1}$ [Crow et al. 1996b; Sokolovsky et al. 1967b]); n=4.
Figure 17:
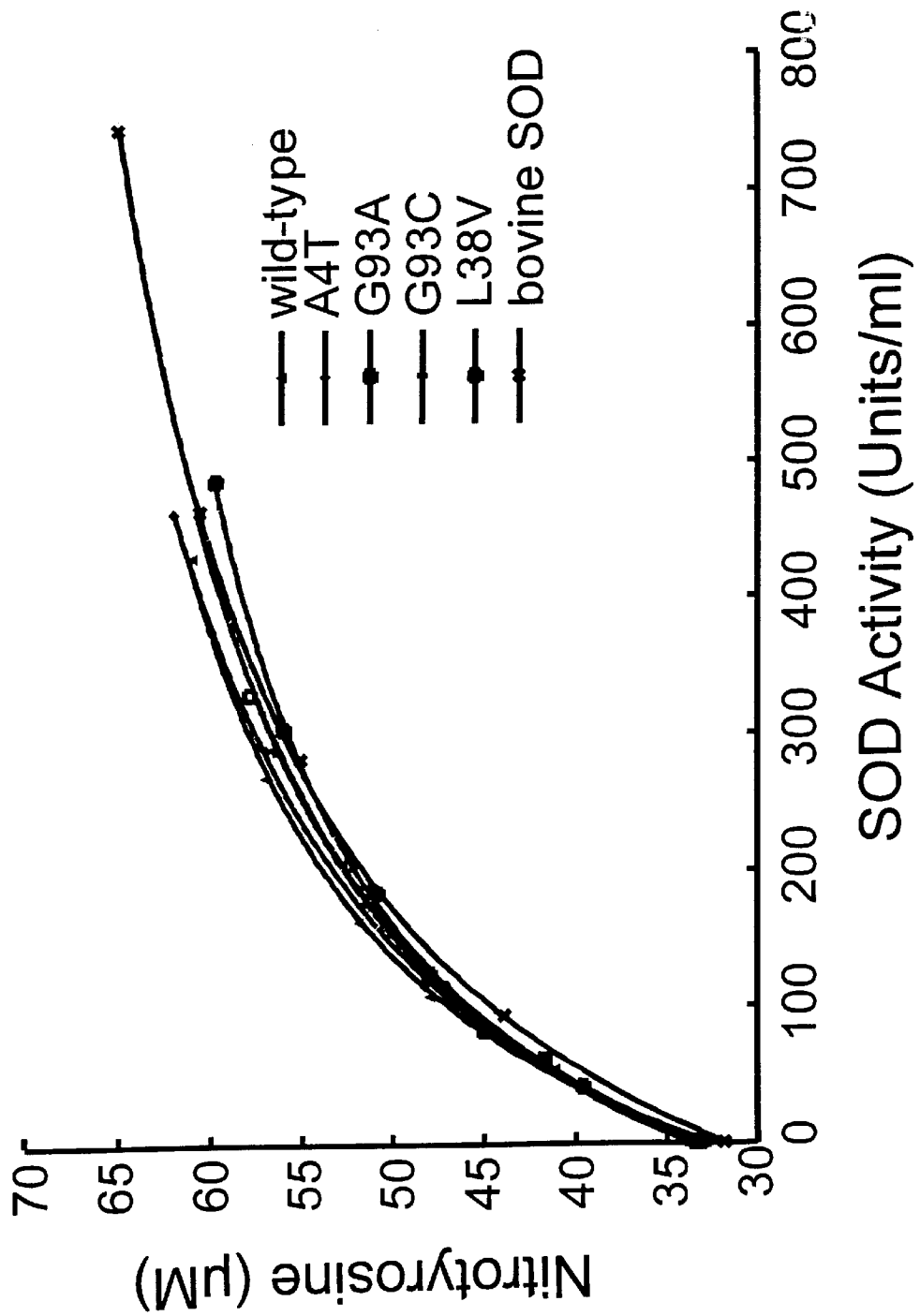
FIG. 17 shows the superoxide dismutation and nitration catalysis by metal-restored superoxide dismutase mutants and wild-type. HPLC-purified enzymes were treated with excess zinc and copper and rechromatographed to remove non-specifically bound metals. Metal content was determined by PAR assay in 6 M guanidine-HCl. Superoxide dismutase activities were determined by their ability to inhibition of cytochrome c reduction in the presence of xanthine oxidase and xanthine (McCord et al. 1969). Nitration activities were determined as described.

The consequence of zinc loss on nitration catalysis by superoxide dismutase is shown in FIG. 16. Relative to zinc- and copper-containing superoxide dismutase (Cu$_2$Zn$_2$), zinc-deficient superoxide dismutase (Cu$_2$E$_2$) dose-dependently increased the nitrotyrosine yield following peroxynitrite addition to a tyrosine-containing tripeptide (FIG. 16). Nitration yield was enhanced 1.6-fold at saturating superoxide dismutase and 2.5-fold at lower concentrations of superoxide dismutase which are more likely to reflect the fraction of superoxide dismutase which might exist in the zinc-deficient state in vivo. Incorporation of either zinc, copper, or cobalt to the zinc binding site of superoxide dismutase decreased the catalytic efficiency for nitration to that of native, copper- and zinc-containing (Cu$_2$Zn$_2$) superoxide dismutase. Additions of metal to native copper- and zinc-containing enzyme had no effect on nitration catalysis, indicating that the effects on nitration were due to protein-bound metals. Enhancement of nitration yield by zinc-deficient wild-type enzyme was the same as that seen with the zinc-deficient mutant I113T, suggesting that the effect was a function of zinc status rather than the mutations per se. When fully saturated with metals, specific dismutase and nitration activities of four superoxide dismutase mutants were virtually identical to wild-type human superoxide dismutase (FIG. 17), providing additional evidence that these ALS-associated mutations, in and of themselves, do not alter the intrinsic activity of the enzyme.

Tyrosine nitration catalyzed by wild-type superoxide dismutase is among the fastest reactions known for peroxynitrite (Beckman et al. 1992) and could contribute to the pathogenesis of both sporadic and familial ALS. Zinc loss from superoxide dismutase mutant proteins due to their decreased zinc affinity will enhance tyrosine nitration in familial ALS by two complimentary effects. Zinc-deficient superoxide dismutase is approximately twice as efficient as wild-type superoxide dismutase as a catalyst of tyrosine nitration by peroxynitrite. Nitration is further amplified in vivo because zinc-deficient superoxide dismutase has about half the superoxide scavenging activity of wild-type (Pantoliano et al. 1982; Forman et al. 1973), leading to an increase in the steady-state concentration of superoxide and, by reaction with nitric oxide, increased peroxynitrite formation (Scheme 1). Although an accumulation of zinc-deficient superoxide dismutase in familial ALS patients will increase the probability of tyrosine nitration at a given flux of peroxynitrite, the same extent of nitration can occur in motor neurons with wild-type superoxide dismutase in sporadic ALS patients when exposed to a proportionally higher or more prolonged generation of nitric oxide. In sporadic ALS patients, nitrotyrosine immunoreactivity has been localized over neurofilamentous inclusions in both upper and lower motor neurons (Chou et al. 1996; Abe et al. 1995). Nitrotyrosine has also been shown to increase in both G93A and G37R superoxide dismutase transgenic mice. These results establish that tyrosine nitration occurs in degenerating motor neurons. Further, nitrated neurofilament subunits inhibit native subunit assembly in vitro. Together, these results suggest that nitration is a plausible mechanism for superoxide dismutase-mediated injury in both sporadic and familial ALS.

Decreased affinity of superoxide dismutase for zinc, proposed by Lyons et al (1996), Crow et al. 1996c; Sampson et al. 1996; Beckman 1996), offers a simple explanation for how more than 50 different mutations can have a common toxic phenotype. Zinc has an important structural role in superoxide dismutase, helping to hold together two loops that form the narrow active site around the copper (Tainer et al. 1983). Zinc is coordinated to the copper though the bridging histidine 63 and may help stabilize the Cu$^{+1}$ enzyme intermediate during the catalytic cycle of superoxide dismutase. Wild-type superoxide dismutase excludes a large fraction of peroxynitrite from reacting with the active site (Beckman et al. 1992). In the absence of zinc, the constraints holding together the amino acids forming the active site of superoxide dismutase may be relaxed, allowing greater access to peroxynitrite and thereby increasing nitration yield. The concept of a more relaxed active site in superoxide dismutase mutants has also been suggested by Yim et al (1996).

Because zinc shares a common histidine ligand with copper, zinc deficiency may also alter the redox properties of copper which may, in turn, influence the nitration reaction. Rather than affecting residues which bind zinc or copper, most of the 50 known mutations occur in the β-barrel structure of superoxide dismutase at positions known to contribute to the stability of superoxide dismutase. Mutations that weaken the compact superoxide dismutase structure can strain the geometry of the zinc-binding ligands and thereby reduce zinc affinity. The calculated zinc affinities from the PAR competition assay were $10^4$ to $10^5$ weaker than copper, explaining why zinc would be preferentially lost before copper from superoxide dismutase. The copper-containing, zinc deficient superoxide dismutase was remarkably stable and capable of rebinding zinc after a 66 hours incubation in 2 M urea at 37° C.

Zinc affinity was decreased by a maximum of 30-fold for the superoxide dismutase mutant protein A4V; familial ALS patients possessing this mutant are known to experience an unusually rapid progression of the disease (Rosen et al. 1994a). The affinities for zinc in all of the mutants are still sufficiently high such that another zinc binding protein or chelator would be required to remove zinc from the active site. Neurofilament-H, as purified from human spinal cord, has four zinc atoms bound with such high affinity that extensive dialysis against 25 mM EDTA failed to remove it (Pierson et al. 1988). While investigating the nitration of NF-L by superoxide dismutase, NF-L bound up to 12 zinc atoms with an affinity at least as great as wild-type superoxide dismutase and considerably higher than four ALS superoxide dismutase mutants. Virtually all known low molecular weight chelators capable of binding zinc also bind copper with affinities ranging from 1,000 to 100,000 times higher (Dawson et al. 1989); the same is true for apo metallothionein II (Shaw et al. 1991). However, the affinity of NF-L for copper was much lower than for zinc, suggesting that NF-L could preferentially remove zinc from superoxide dismutase without affecting its copper content.

Accumulation of neurofilaments in the soma of motor neurons and in axonal swellings are pathological hallmarks of ALS in humans. Superoxide dismutase has been colocalized with abnormal neurofilament conglomerates in both lower and upper motor neurons in ALS patients (Chou et al. 1996). Moreover, these same conglomerates also contained neuronal nitric oxide synthase and nitrotyrosine immunoreactivity (Abe et al. 1995), indicating not only that a source of nitric oxide is present but that protein nitration is occurring. The strong affinity of neurofilament proteins for zinc might promote the formation of zinc-deficient superoxide dismutase, which would, in turn, increase the nitration of proteins by peroxynitrite. Thus, nitration of NF-L in vivo could lead to the further accumulation of misassembled neurofilaments. The appeal of this hypothesis is its ability to explain the selective vulnerability of motor neurons. In transgenic mice overexpressing ALS-mutant superoxide dismutases, abnormal accumulations of neurofilaments are observed in some mouse lines (Tu et al., 1996), but not in others (Cleveland et al. 1996). Thus, other pathological mechanisms involving superoxide dismutase are likely to be involved in motor neuron death in ALS.

Scheme 1

The Dual Nature of Superoxide Dismutase: Catalysis of Superoxide Dismutation and Tyrosine Nitration by Peroxynitrite.

Superoxide dismutase normally functions to prevent peroxynitrite formation by scavenging superoxide. However, nitric oxide reacts with superoxide three times faster than superoxide dismutase can scavenge superoxide. Thus, formation of peroxynitrite is largely driven by nitric oxide concentration such that when the concentration of nitric oxide is only one-third that of superoxide dismutase, 50% of all superoxide would react to form peroxynitrite. Peroxynitrite, in turn, reacts rapidly with superoxide dismutase to produce a nitronium-like nitrating species which nitrates tyrosine residues in proteins. Zinc loss from superoxide dismutase, following interaction with NF-L or other zinc-binding proteins, would result in enhanced nitration catalysis and decreased superoxide scavenging activity which would, in turn, further augment peroxynitrite formation. Nitration decreases the $pK_a$ of tyrosines hydroxyl group from 10 to 7.5 (Sokolovsky et al. 1967) thereby adding a negative charge to this normally hydrophobic residue. Nitrotyrosine may alter protein function by affecting its conformation or, in the case of structural proteins like NF-L, interferring with hydrophobic associations with other subunits.

EXAMPLE 15

Bathocuproine-mediated Removal of Cu+1 from Zinc-deficient Human Cu,Zn SOD

Metal contents of recombinant human Cu,Zn SOD are determined using the PAR assay in 6 M guanidine hydrochloride. Metals were removed from SOD by dialysis at pH 4 and copper only was added back to human Cu,Zn SOD to give a zinc-deficient form (0.93 copper per subunit, 0.07 zinc per subunit). Addition of Cu+2 sulfate to a solution of bathocuproine sulfonate (2,9-dimethyl-4,7-diphenyl-1,10-phenanthroline sulfonate or BCS) at pH 7.4 resulted in no change in the UV-visible absorbance spectrum (210 to 510 nm). While collecting data at a rate of 2.5 points per sec, addition of 50 M ascorbic acid resulted in an immediate and sustained increase in absorbance (maximum at 480 nm) consistent with formation of a Cu+1-BCS. No absorbance change was seen when divalent zinc was added to BCS in the presence or absence of ascorbic acid.

No absorbance change at 480 nm was seen when native wild-type human Cu,Zn superoxide dismutase (SOD) was added to a solution containing a 10-fold molar excess of BCS (not shown). Addition of ascorbic acid (1 mM) to the SOD/BCS solution had no effect on 480 nm absorbance indicating either that ascorbic acid was incapable of reducing Cu+2-SOD to Cu+1-SOD or that Cu+1 was bound to tightly to be competed away by BCS.

Figure 18:
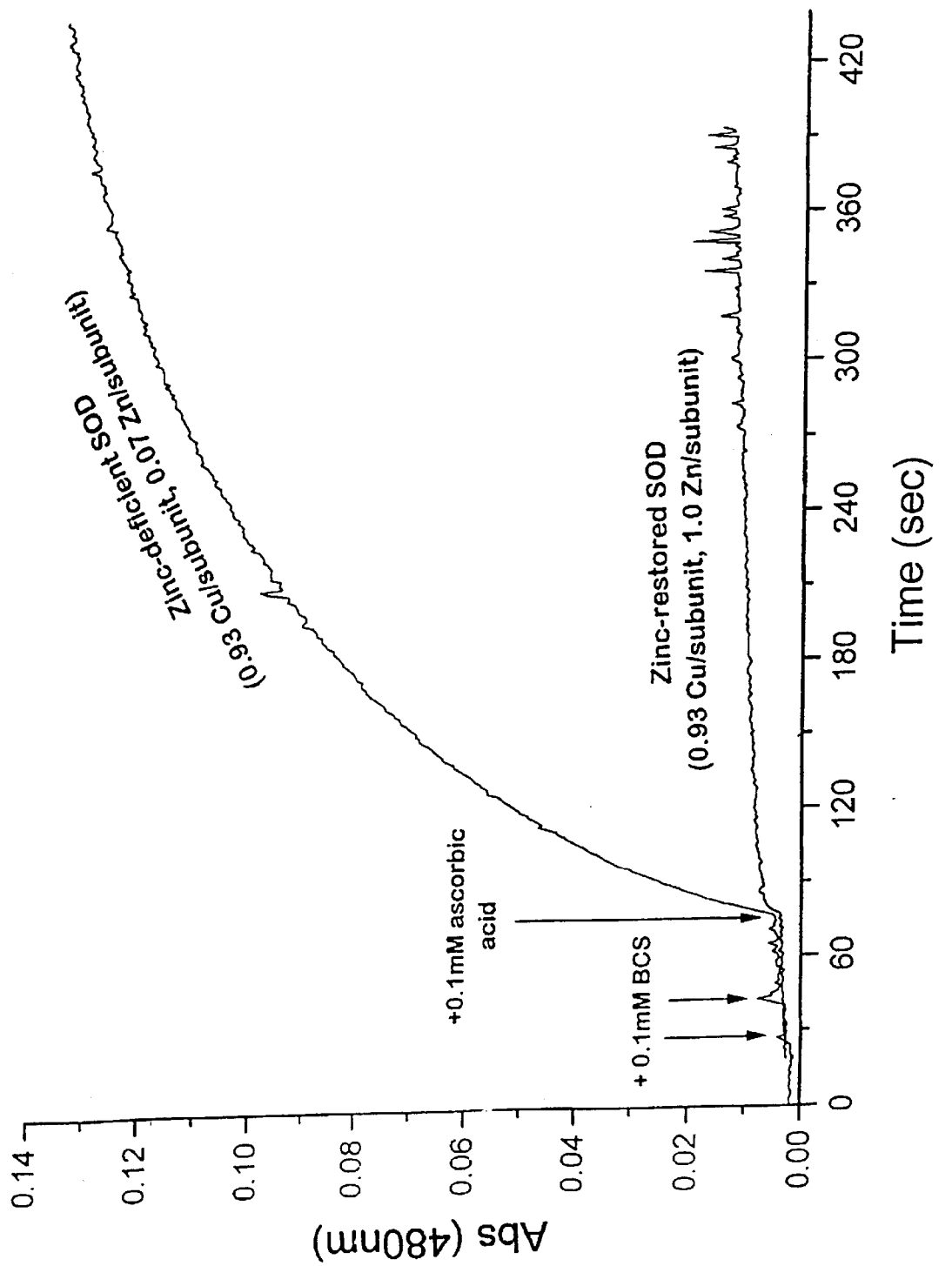
FIG. 18 shows the zinc-deficient SOD ($\mp$pre-incubation with 11 M zinc sulfate) was added to a final concentration of 10 M to a rapidly stirred solution of 0.1 M potassium phosphate, pH 7.4 at 37° C. BCS (bathocuproine sulfonate or 2,9-dimethyl-4,7-diphenyl-1,10-phenanthroline sulfonate) was added to 0.1 mM at the times indicated followed by 0.1 mM ascorbic acid. Absorbance data (at 480 nm) was collected at a rate of 2.5 points per sec.

Aliquots of the same human SOD preparation were made apo by dialysis at pH 4 and copper only was added back to give an enzyme species containing 0.93 copper atoms per subunit (maximum of 1.0) and 0.07 zinc atoms per subunit (maximum of 1.0). Addition of BCS to this 'zinc-deficient' human SOD had no effect. However, subsequent addition of 0.1 mM ascorbic acid resulted in rapid formation of the Cu+1-BCS complex as evidenced by the increased in 480 nm absorbance (FIG. 18). Based on the empirically determined extinction coefficient for the Cu+1-BCS complex (E=14,700 M−1cm−1), all of the copper was removed from the zinc-deficient form of SOD over the 400 sec time course shown (FIG. 18). When the same 'zinc-deficient' SOD was pre-incubated with a 10% molar excess of zinc (to ensure saturation of the zinc binding site) BCS plus ascorbic acid was incapable of removing copper from SOD (FIG. 18), indicating that the BCS-mediated removal of copper from SOD is totally a function of bound zinc.

Figure 19:
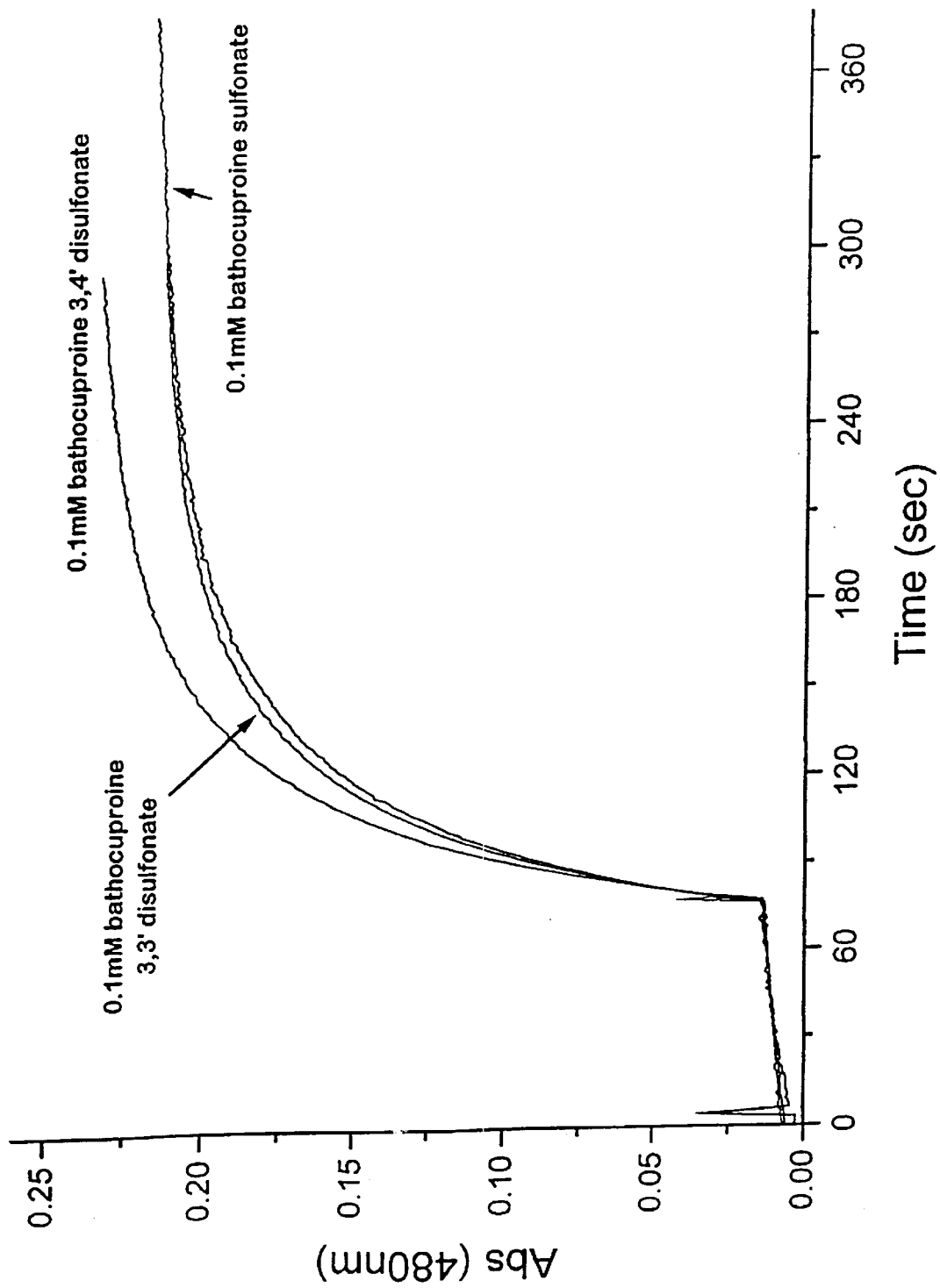
FIG. 19 shows the low zinc affinity site-directed SOD mutant D124N was added to a phosphate buffered solution as in FIG. 18 to a concentration of 15 M. 0.1 mM of the indicated bathocuproine analog was added to one of three separate reactions followed by 0.1 mM ascorbic acid. 480 nm absorbance was monitored as described.

A site-directed SOD mutant wherein Asp124 was mutated to asparagine (hence D124N) was created, expressed in E. coli and purified. D124N binds zinc with much lower affinity than does wild-type SOD resulting in an inherently zinc-deficient form as purified. D124N was used to characterize three different bathocuproine analogs with respect to their copper removal kinetics. Although the exact extinction coefficients for the Cu+1 complexes of BCS, bathocuproine 3,3'-disulfonate (BC-3,3'-DS), and bathocuproine 3,4'-disulfonate (BC-3,4'-DS) differed slightly, the time courses for copper removal following ascorbic acid was virtually superimposible (FIG. 19). These results suggest that the location of the sulfonic acid moieties on bathocuproine have no effect on the ability of the parent compound to remove copper from zinc-deficient SOD.

It is well known that bathocuproine sulfonate binds Cu+1 but not Cu+2. This was demonstrated with free Cu+2 sulfate and ascorbate both as a verification of this binding specificity and to examine the kinetics of Cu+1 binding. Bathocuproine sulfonate binds free Cu+1 virtually instantaneously. Subsequent experiments which measured the rate of reduction of the zinc-deficient SOD by ascorbic acid revealed that complete reduction occurred with a few second. Thus, the kinetics of bathocuproine sulfonate-mediated copper removal from zinc-deficient SOD reflect either how rapidly Cu+1 dissociates from zinc-deficient SOD (and is trapped by BCS) or how well bathocuproine sulfonate can gain access to the active site of zinc-deficient SOD and thereby facilitate removal of Cu+1.

Subsequent experiments with fully metallated SOD (i.e., maximal amounts of bound zinc and copper) revealed that it's copper is reduced much more slowly than is the copper in zinc-deficient SOD (not shown). However, even when fully metallated Sod was reduced with sodium borohydride, a well-characterized and efficient copper reductant, bathocuproine sulfonate still did not remove the copper. This is consistent with either a lower copper binding affinity with zinc-deficient SOD or with a more accessible active site.

At least four of the Sod mutants associated with familial ALS (FALS) bind zinc less well than wild-type SOD. Changes in zinc affinity may be the common phenotype underlying all 50 or so ALS-associated SOD mutants described to date. Zinc-deficient SOD is a better catalyst of tyrosine nitration by peroxynitrite and enhanced nitration catalysis may be the toxic gained function of SODs responsible for motor neuron death in ALS. The abundance of a protein (neurofilament-L) in motor neurons which avidly binds zinc opens the possibility that all forms of ALS may involve zinc loss from SOD and production of a more toxic zinc-deficient form. Because nitration catalysis is totally dependent on bound copper, removal of copper would render SODs non-toxic.

Ascorbic acid is present in neurons at concentrations sufficient to keep zinc-deficient SOD mutants predominantly in the reduced (Cu+1) form. Bathocuproine analogs should selectively remove copper from the toxic zinc-deficient forms while having no effect on fully metallated SOD.

EXAMPLE 16
Bathocuproine in ALS SOD Transgenic Mice

Neither the overall efficiency nor the kinetics of Cu+1 removal was altered by sulfonic acid substituents on the ring(s) of the parent bathocuproine compound. Thus, the sulfonic acid groups serve mainly to increase water solubility and are not fundamental to copper binding activity. The unsubstituted parent compound, bathocuproine, is very lipid soluble and much more likely to cross the blood-brain barrier. In G93A transgenic mice, bathocuproine was dissolved in soybean oil and injected intraperitoneally at a daily dose of 0.51 mg/100 g body weight. Assuming uniform tissue distribution and fluid fraction equal to 0.7 of the mouse's body weight, this dose should give a cellular concentration of 20 M or roughly a 4-fold molar excess over SOD protein concentration. The G93A mouse overexpresses the human G93A ALS SOD mutant transgene and shows symptoms of motor neuron loss (limb paralysis) at about 200 days of age. After onset, paralysis progresses rapidly up the trunk and is ultimately fatal within about 14 days. Bathocuproine injections is initiated in 190 day old mice and the mice are observed for onset and progression of paralysis relative to untreated littermates. The delay of onset or slowing of progression is shown. A group of non-transgenic mice are also injected to control for potential toxicities from bathocuproine itself.

EXAMPLE 17
Selective Removal of Copper from $Zn_0SOD$

Figure 20:
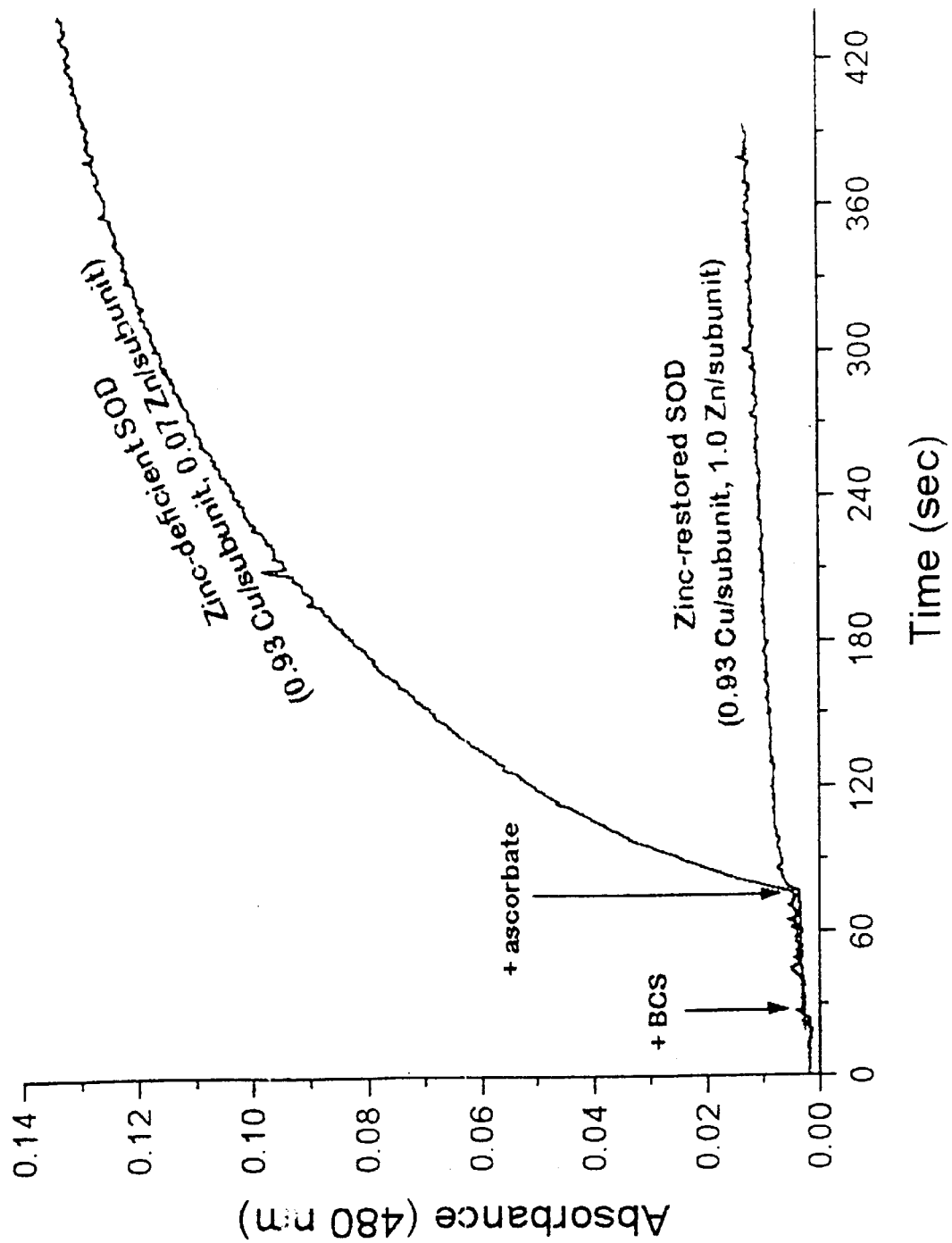
FIG. 20 shows the selective removal of Cu$^{+1}$ from zinc-deficient wild-type SOD by Bathocuproine Sulfonate (BCS) and Inhibition by Zinc. 10 $\mu$M of zinc-deficient SOD subunit was added to 1.4 ml of 0.1 M KPi buffer, pH 7.4 at 37° C. BCS (0.1 mM) was added followed by 0.1 mM ascorbate; absorbance was monitored at 480 nm (14,700 M$^{-1}$cm$^{-1}$). Preincubation of zinc-deficient SOD with one molar equivalent of zinc (which resulted in zinc binding to SOD) prior to addition to the cuvette blocked completely blocked copper removal by BCS.

The present invention demonstrates that zinc-deficient SOD is rapidly reduced to $Cu^{+1}$-SOD by cellular reductants such as ascorbate and that, upon reduction, the $Cu^+$ is readily removed by $Cu^{+1}$-specific chelators like bathocuproine sulfonate or neocuproine sulfonate; addition of one equivalent of zinc inhibits both reduction and copper removal (FIG. 20).

The reducibility of zinc-deficient SOD, combined with the ability of bathocuproine sulfonate (BCS) or neocuproine sulfonate (NCS) to remove the resulting $Cu^{+1}$, can selectively detoxifying the zinc-deficient SOD which may be the pathologic form of SOD (2) in FALS and in ALS SOD transgenic mice. In addition, this finding accounts for the protective effect of BCS and NCS in cell culture models where FALS mutants have been transfected or otherwise integrated into the cell cytosol. Aside from the potential therapeutic uses, the BCS (or NCS) plus ascorbate assay allows one to distinguish between zinc-deficient SOD ($Zn_0SOD$) and the 'normal' holo form ($Zn_2SOD$) either in vitro or in crude tissue homogenates and forms the basis for the assertion that a large fraction of the total SOD present in mouse spinal cord is in fact zinc-deficient (see FIG. 21).

EXAMPLE 18
$Zn_0SOD$ is Present in G93A Transgenic Mouse Tissues

Figure 21:
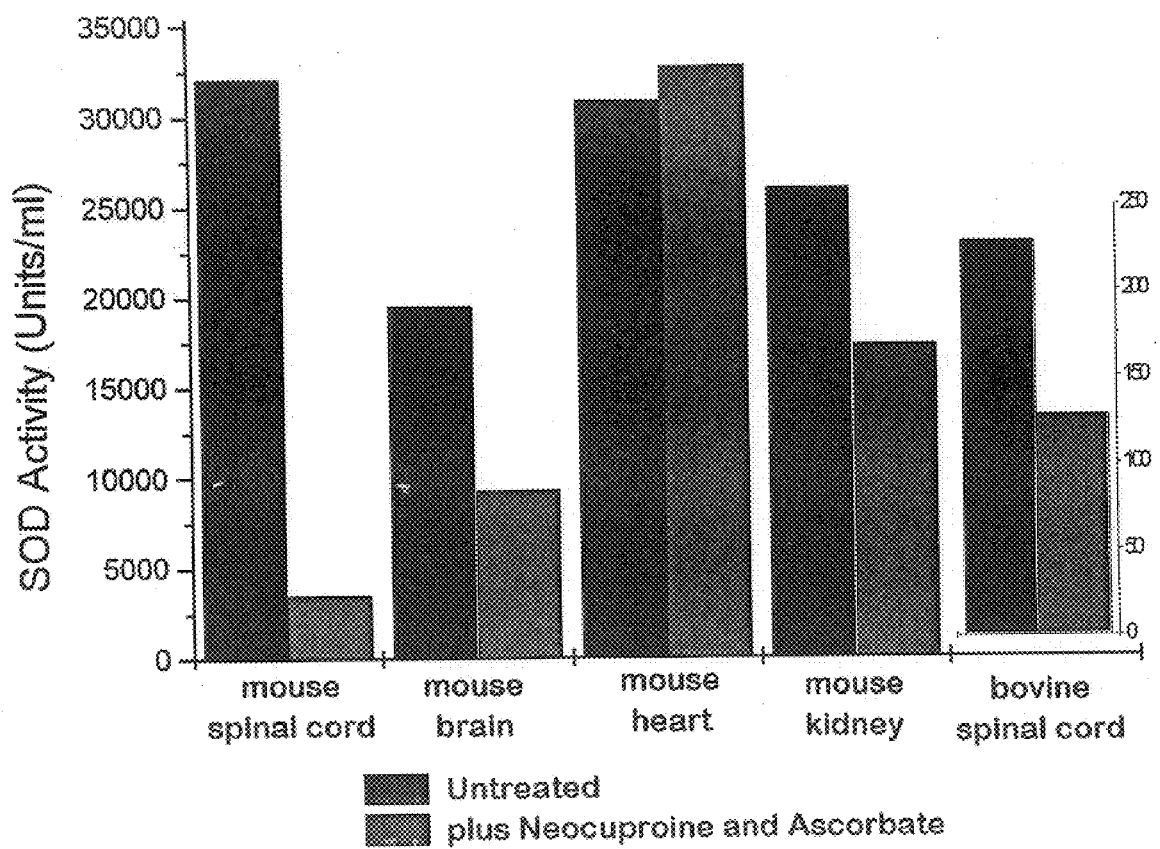
FIG. 21 shows the demonstration of presence of Zinc-deficient SOD in G93A mouse. Organs were extracted from mice displaying hindlimb paralysis and homogenized in PBS, pH 7.4 containing 1% (v/v) Triton X100. Insoluble material was pelleted by centrifugation and standard cytochrome c assays for SOD activity were carried out in triplicate using supernatants before and after (within 5 min) addition of 0.1 mM neocuproine (NCS) and 0.4 mM ascorbate.

The NCS plus ascorbate assay for selective copper removal from zinc-deficient SOD provided a method for determining whether $Zn_0SOD$ was present in G93A transgenic mice. Zinc-deficient SOD retains most of its superoxide scavenging activity (2,4) in the standard cytochrome c assay (25). Because copper removal completely inhibits superoxide scavenging activity the cytochrome c assay was used to measure the total amount of SOD activity in crude mouse and bovine tissue homogenates before and immediately (~5 min) after treatment with NCS and ascorbate (FIG. 21).

Tissues from two G93A transgenic mice at endstage disease were utilized. FIG. 21 suggests not only that $Zn_0SOD$ exists in these tissues but also that the percent of total SOD activity due to $Zn_0SOD$ is much greater in spinal cord—as much as 90% of the total activity appears to be due to $Zn_0SOD$. Treatment with NCS plus ascorbate had no effect on total SOD activity in mouse heart tissue (FIG. 21) indicating that none of the SOD in heart was zinc-deficient. Roughly 50% of the total SOD activity in mouse brain was due to $Zn_0SOD$ as was 30% of the activity in mouse kidney. Interestingly, approximately 44% of the total SOD activity in bovine spinal cord was due to $Zn_0SOD$. The much higher total SOD activity (on a per ml basis) in mouse spinal cord reflects the fact that this G93A transgenic mouse line greatly overexpresses G93A hSOD and that the bovine tissue homogenate had a lower total protein concentration (i.e., was more dilute due to homogenization conditions).

EXAMPLE 19
$ZN_0SOD$ in Tissues

The relatively high precentage of SOD which is zinc-deficient in the mouse tissues could be related to the high overexpression per se and the limited amount of zinc present in the tissues. However, three factors suggest that overpression cannot fully account for the high percentage of zinc-deficiency: 1) total SOD activity is similar in mouse heart yet all the SOD in heart appears to contain zinc, 2) the very existence of high superoxide scavenging activity in the mouse tissues indicates that copper is not limiting and if the animal can cope with increased amounts of toxic copper, one might expect that innocuous zinc could be increased to meet demand as well, and 3) the SOD activity in bovine spinal cord reflects normal expression of wild-type bovine SOD yet still contains a significant fraction of $Zn_0SOD$. These findings in bovine spinal cord may have important implications for SALS, i.e., that, under some circumstances, it may be possible to obtain significant amounts of $Zn_0SOD$ from wild-type SOD. This leaves open the possibility that SALS and FALS could have a similar biochemical etiology.

EXAMPLE 20
D124N as a Model of $Zn_0SOD$

About 50 mg of wild-type SOD (and lessor amounts of ALS mutants) was obtained from each six liter grow-up of *E. coli* and significant amounts of enzyme are lost during the process of making the SODs zinc-deficient. To circumvent this problem, a site-directed human SOD mutant was prepared wherein aspartate$_{124}$ was changed to asparagine (D124N). D124N had been prepared and characterized by Banci et al (28) who found that the inability of the asparagine mutant to form a hydrogen bond with His$_{46}$ and His$_{71}$ resulted in lowered affinity for zinc. Very good yields of D124N were obtained and the inherently poor zinc binding of this mutant allowed experiments without regard to the trace amounts of zinc contaminanting buffers and tissues.

EXAMPLE 21
Reduction of $Zn_0SOD$ by Cellular Reductants

Figure 22:
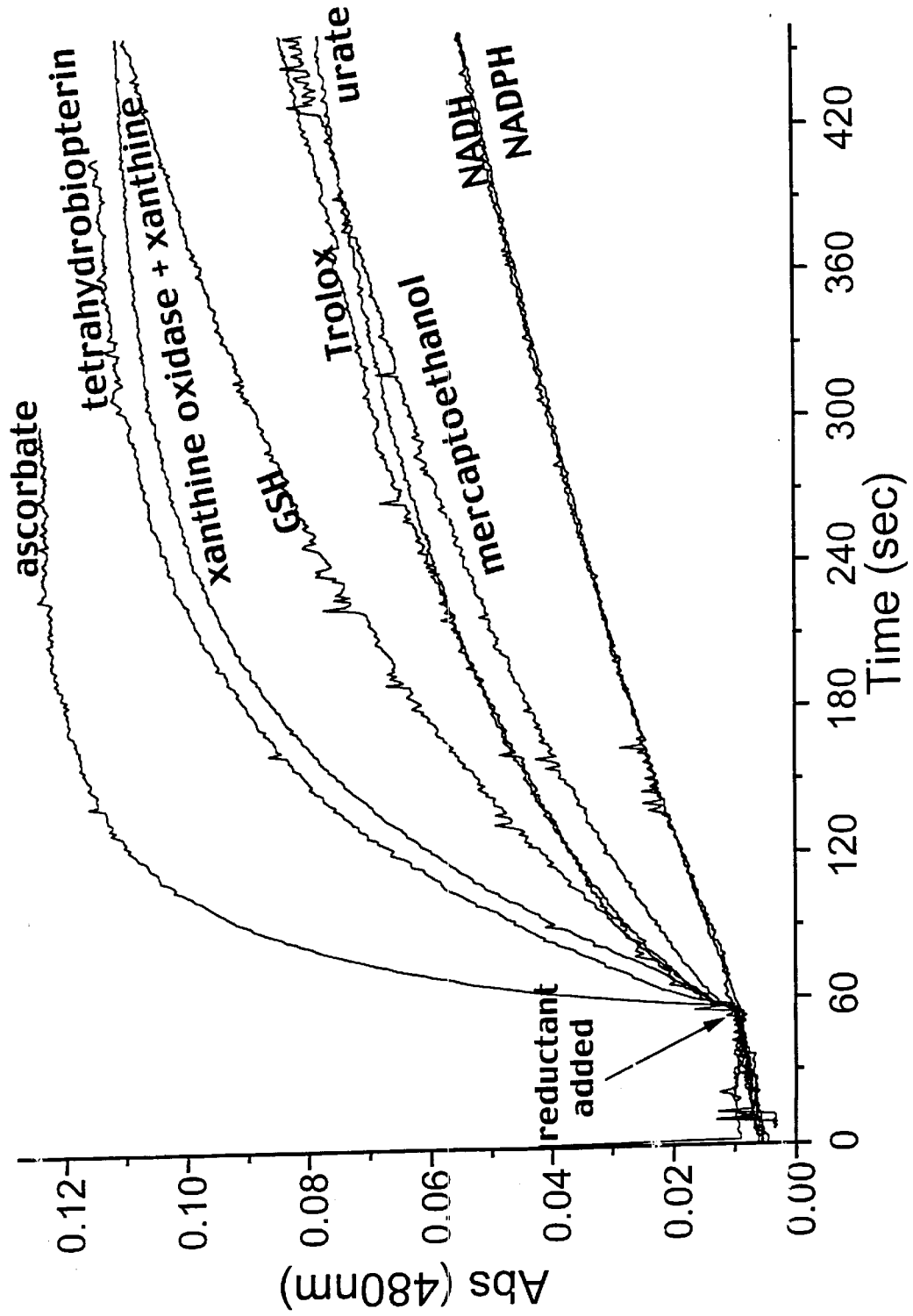
FIG. 22 shows the Cu$^{+1}$ removal from D124N (Zinc-Deficient) SOD by Bathocuproine: Comparison of Biologic Reductants. Reactions contained 8 $\mu$M SOD subunit in 0.1 M KPi, pH 7.4 at 37° C. Bathocuproine sulfonate (BCS)was added to 0.1 mM followed by 0.1 mM of the indicated reductants. The xanthine oxidase (XO) reaction contained 25 milliunits/ml of XO and 80 $\mu$M xanthine.

A number of experiments were carried out with D124N which indicated that it had a zinc binding affinity quite similar to the ALS mutant A4V (see FIG. 10) and shared many of the properties of zinc-deficient SODs (mutants or wild-type). For example, the copper in D124N was easily reduced and could be extracted as $Cu^{+1}$ by BCS. The BCS assay was used to examine the relative ability of various cellular reductants to reduce D124N (FIG. 22); all reductants were added to a final concentration of 0.1 mM. Ascorbate was the most efficient reductant followed by the superoxide-generating system of xanthine oxidase plus xanthine and the reduced cofactor tetrahydrobiopterin (FIG. 22). Other endogenous reductants including glutathione (GSH), urate, NADH, NADPH, and Trolox, the water-soluble derivative of vitamin E, were also quite effective reductants.

EXAMPLE 22
Ascorbate Reduces D124N 200× Faster than Wild-type

A comparison of the rates of ascorbate-mediated reduction was carried out for wild-type SOD, three FALS mutants, and for D124N (Table I); higher concentration of ascorbate (0.5 mM) were used here in order to match the higher concentrations of SODs needed to monitor enzyme-bound copper reduction directly. The half-life for reduction ($t_{1/2}$) of wild-type SOD was determined to be 28.4 min. D90A reduced at the same rate as wild-type and A4V wheresa G93A reduced somewhat more rapidly (25.9 and 20.6 min, respectively). However, the $t_{1/2}$ for reduction for the D124N (the model zinc-deficient SOD) was 8.9 sec—a rate almost 200-fold faster than wild-type. In fact, the rate of D124N reduction was too fast to be measured spectrally and required stopped-flow spectroscopy.

TABLE I

| SOD | t½ for reduction of ascorbate |
| --- | --- |
| A4V | 25.9 min. |
| D90A | 29.5 min. |
| G93A | 20.6 min. |
| D124N | 8.9 seconds |

SODs were present at a subunit concentration of 0.43 mM in 0.5 ml of 0.1 mM Kpi, pH 7.4 at 37 degrees C. Ascorbate (0.5 mM) was added at time zero and reduction was monitored spectrally at 680 nm for 1 hr.

TABLE II

| SOD | t½ for reduction by $H_2O_2$ |
| --- | --- |
| Wild type | 30.5 seconds |
| A4V | 21.2 seconds |
| D90A | 30.9 seconds |
| G93A | 24.2 seconds |
| D124N | 26.7 seconds |

SODs were present at a subunit concentration of 0.43 mM in 0.5 ml of 0.1 mM Kpi, pH 7.4 at 37 degrees C. $H_2O_2$ (0.4 mM) was added at time zero and reduction was monitored spectrally at 680 nm for 5 minutes.

EXAMPLE 23
$Zn_0SOD$ as a Net Producer of Superoxide and $H_2O_2$

The ability of these different biological reductants to reduce the copper in zinc-deficient SOD indicates not only that the active site is considerably more accessible, but also that any zinc-deficient enzyme would exist in the completely reduced state at all times in vivo. Whether viewed thermodynamically or kinetically, fully reduced SOD ($Cu^{+1}$) can only go in one direction—towards reoxidation ($Cu^{+2}$-SOD). Spontaneous reoxidation yields superoxide whereas the addition of a second superoxide (the second half of the 'ping-pong' reaction of SOD) yields hydrogen peroxide and $Cu^{+2}$-SOD which would then be quickly re-reduced by cellular reductants. The net result is that zinc-deficient SOD would consume cellular reductants to produce hydrogen peroxide, superoxide, and, in the presence of nitric oxide, peroxynitrite as demonstrated herein (see FIG. 25a,b).

EXAMPLE 24
SODs are Readily Reduced by $H_2O_2$-the SOD Reaction in Reverse

For more than two years the notion that FALS SODs could act as peroxidases and generate hydroxyl radical has been a subject of debate. However, $H_2O_2$ can rapidly reduce Cu,Zn SOD and generate superoxide as a byproduct. (It is the addition of a second molecule of $H_2O_2$ to give —OH that is extremely slow and of questionable significance). As indicated in Table II, the rates of SOD reduction by $H_2O_2$ are quite fast and differ little between SODs—even D124N. This rapid and essentially indescriminant reduction by $H_2O_2$ becomes quite useful for comparing different properties of reduced SODs. For example, it is possible to assess superoxide production from reduced SOD using the tetranitromethane (TNM) capture assay described by Hodgson and Fridovich (7).

EXAMPLE 25
Production of Superoxide from Reduced ($Cu^{+1}$) SOD

Figure 23A:
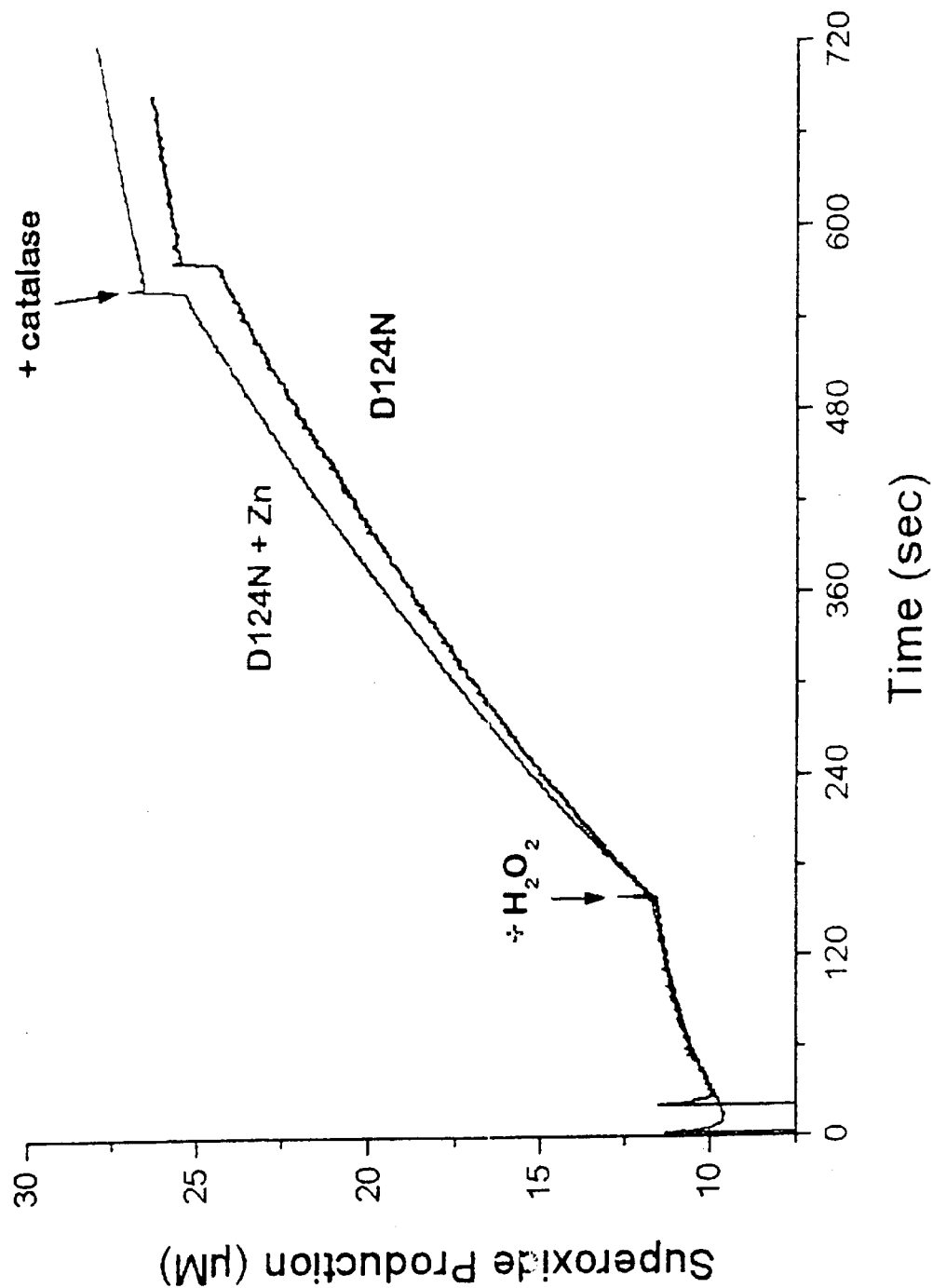
FIGS. 23A and 23B show the Superoxide Production from H$_2$O$_2$-Reduced SOD (Tetranitromethane Reduction).
Figure 23B:
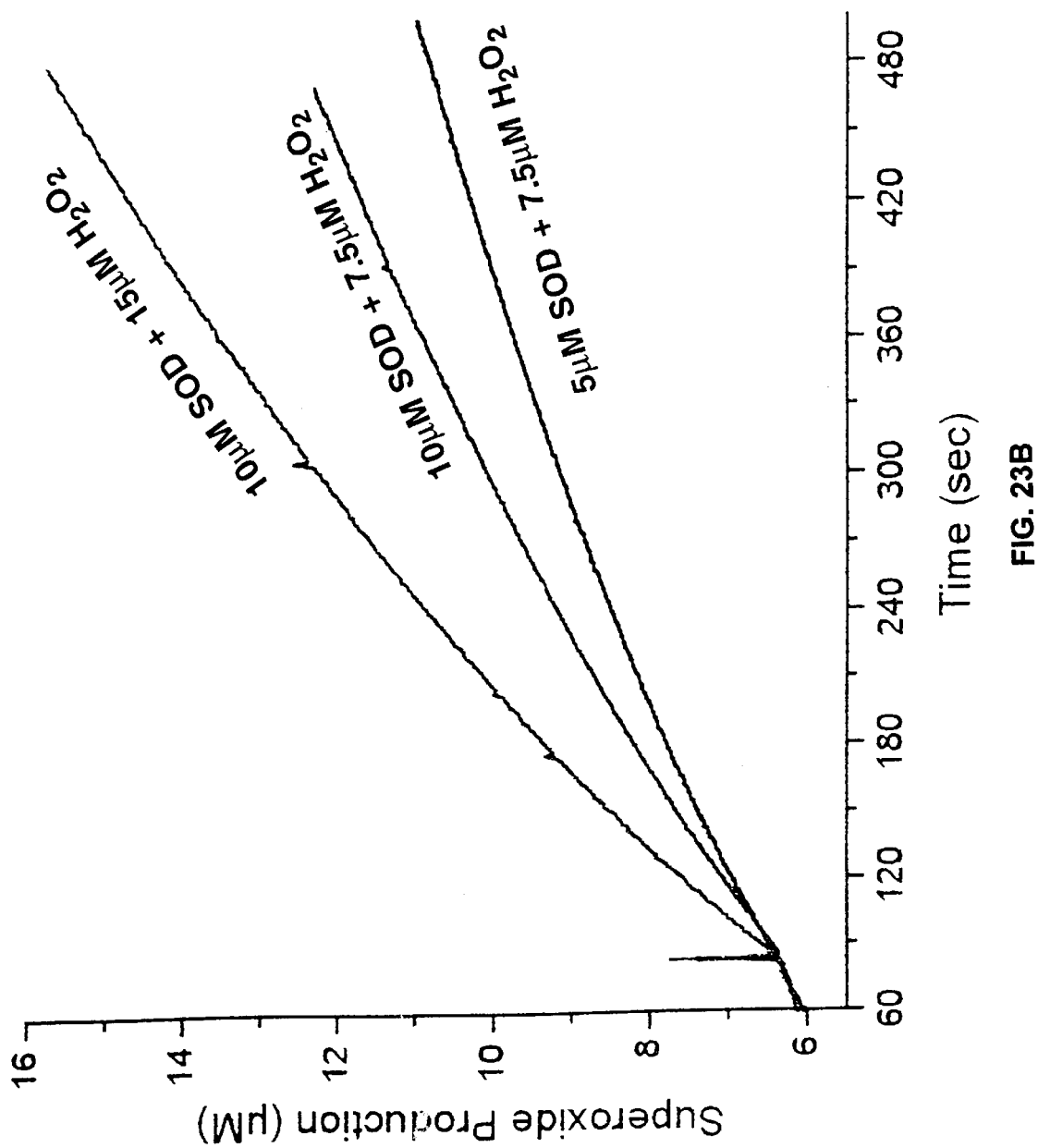

Superoxide reacts at a diffusion-limited rate with TNM to give nitroform anion which has a characteristic absorbance at 348 nm. When $H_2O_2$ is added to a solution containing wild-type SOD and TNM, the production of nitroform anion increases over time and becomes a quantitative measure of superoxide generation from reduced SOD (FIG. 23a). FIG. 23a illustrates that superoxide production is a function of both SOD and $H_2O_2$ concentrations. Addition of $H_2O_2$ (100 µM) to 10 µM D124N results in a rate of superoxide production which on slightly affected by adding zinc back to the zinc-deficient enzyme (FIG. 23b). The subsequent addition of catalase (to decompose any remaining $H_2O_2$) slows the rate of superoxide generation but does not eliminate it; superoxide production after catalase reflects the rate of reoxidation of the reduced ($Cu^{+1}$) enzyme. Thus, $H_2O_2$ drives the dismutase reaction in the reverse direction to produce superoxide and the rate of superoxide generation differs little between wild-type SOD, FALS mutants, or zinc-deficient enzyme.

EXAMPLE 26
Reduced SOD+Nitric Oxide=Peroxynitrite

Figure 24A:
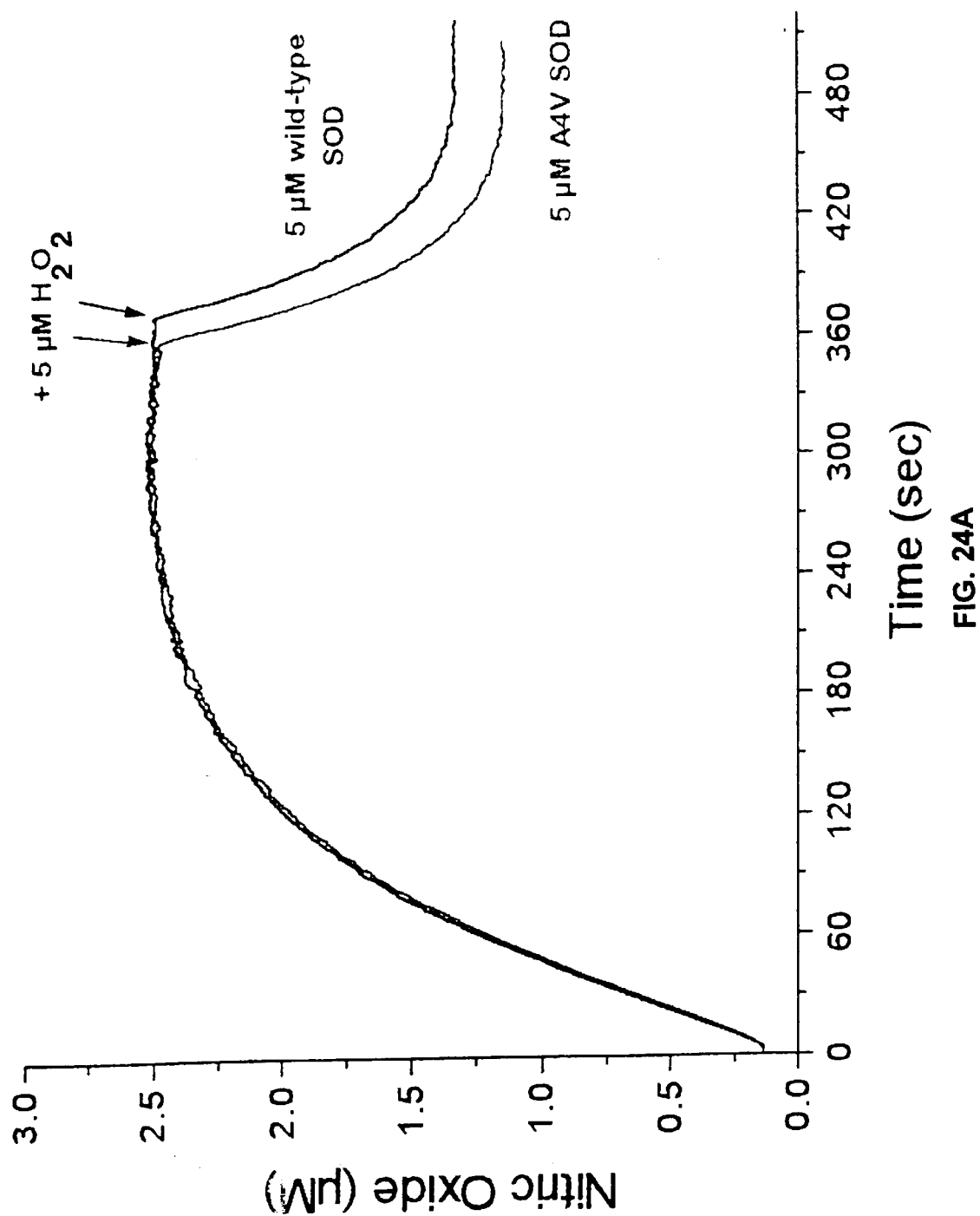
FIGS. 24A, 24B shows the Nitric Oxide Consumption by Reduced SOD and B) Peroxynitrite Production by Reduced SOD in the Presence of Nitric Oxide.
Figure 24B:
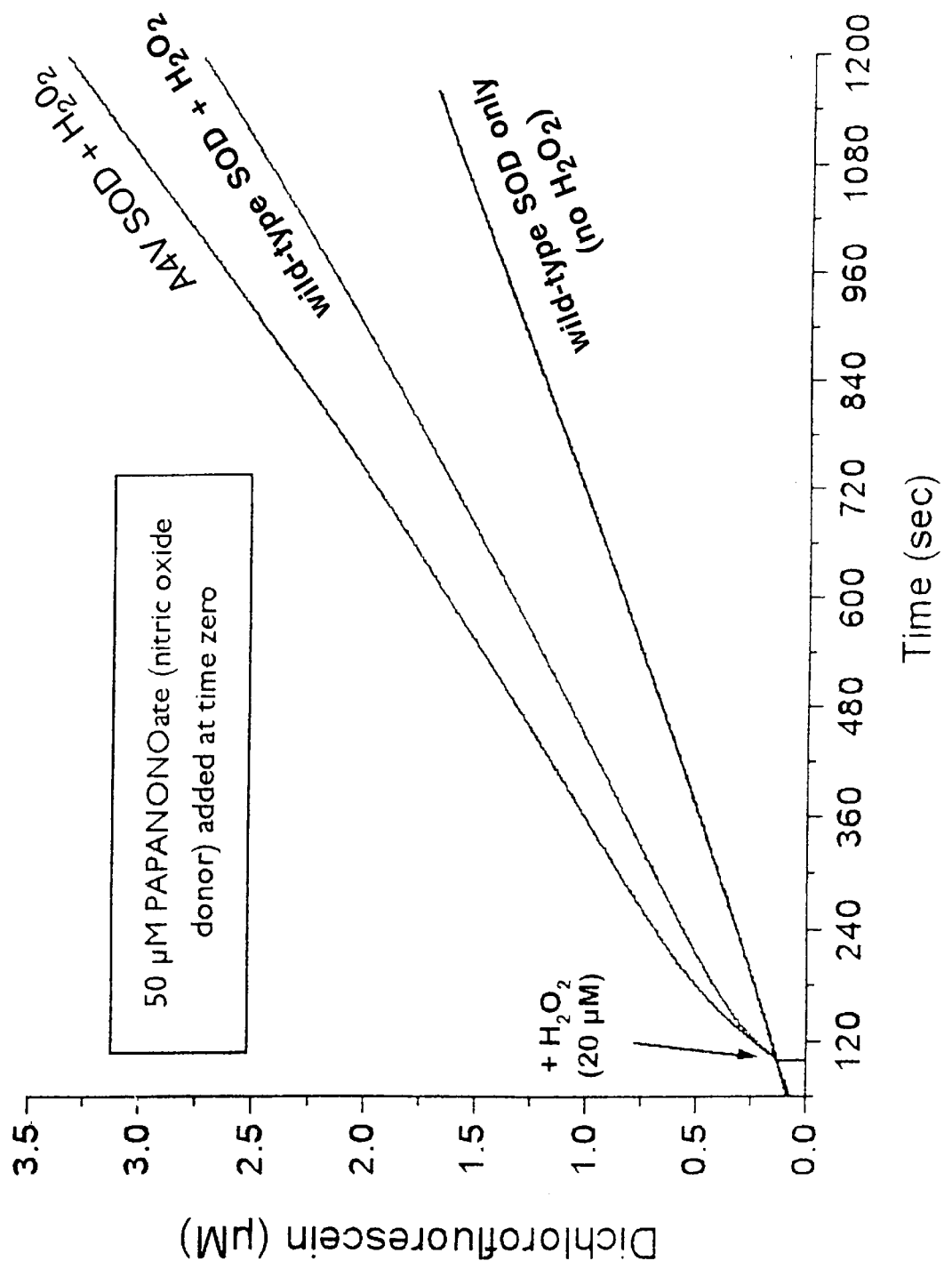

The fact that the reaction of superoxide with TNM is diffusion-limited is quite useful for an in vitro assay, however it is the diffusion-limited reaction of superoxide with nitric oxide ($1.9 \times 10^{10}$ $M^{-1}s^{-1}$) (21) which is physiologically and pathologically relevant. The nitric oxide (NO) donor compound PAPANONOate releases NO at a slow, controlled rate at pH 7.4 and 37° C. ($t_{1/2}$=76 min). Continuous monitoring of NO levels reveals that a steady-state concentration of approximately 2.5 $\mu$M is reached after 4–5 min (FIG. 24a). Addition of 5 $\mu$M SOD has no effect on NO levels, however, subsequent addition of 5 $\mu$M of $H_2O_2$ results in a rapid decrease in NO due to the production of superoxide from SOD. Confirmation that peroxynitrite is formed under these condition is seen in FIG. 24b where the oxidation of the indicator dichlorodihydrofluorescein (DCDHF) to dichlorofluorescein (30) is used to monitor reaction progress. At the concentrations of NO used, very small amounts of the oxidizing radical nitrogen dioxide are formed which accounts for the DCDHF oxidation seen with wild-type SOD in the absence of $H_2O_2$ (FIG. 24b, bottom line). However, higher rates of oxidation are seen with either wild-type or A4V SOD in the presence of $H_2O_2$ (FIG. 24b, middle and top lines).

EXAMPLE 27
Peroxynitrite Production is Dependent on Reduced ($Cu^{+1}$) SOD, not $H_2O_2$ $H_2O_2$ was used as the reductant in these superoxide generation experiments (FIGS. 23a,b and 24a,b) because it readily reduces all SODs and doesn't generate any interferring reaction products, unlike ascorbate, GSH, NADH, etc. Superoxide was generated from reoxidation of reduced ($Cu^{+1}$) SOD irrespective of which reductant was used. For example, if wild-type SOD is incubated with ascorbate for a few hours and allowed to become completely reduced, and the remaining ascorbate and its products (ascorbyl radical and ascorbate quinone) are removed by dialysis or ultrafiltration, the reduced SOD will generate a quantitative amount of superoxide as it spontaneously reoxidizes. This superoxide production will drive either the TNM assay or, in the presence of NO, produce peroxynitrite. FIG. 23 illustrates this: following the addition of catalse to decompose any remaining $H_2O_2$, the slower rate of superoxide production solely reflects the rate of spontaneous reoxidation of reduced SOD. Superoxide production is seen with reduced SOD which has been reduced by ascorbate, GSH, and sodium borohydride; these experiments are simply more tedious due to the need to rigorously remove the reductant and its products prior to carrying out NO consumption or DCDHF oxidation assays.

EXAMPLE 28
PAR Assay for Total Metal Content of SODs

To routinely measure the metal content of purified recombinant SODs, a quick and simple colorimetric assay for copper and zinc was developed which allows one to quantify both metals simultaneously in the same reaction. It is based on denaturing SOD in the presence of the chromophoric chelator 4-pyridylazoresorcinol (PAR) which binds both copper and zinc and has quite high extinction coefficients for both complexes. Two additional non-chromophoric chelators are used to distinguish between $Zn-PAR_2$ and Cu-PAR (FIG. 25).

EXAMPLE 29
Alternate Use of PAR Metal Release Assay for Assessing Relative Protein Stability The metal release assay is based on denaturing SOD in a buffered solution of guanidine HCl in the presence of the PAR until no further increase in 500 nm absorbance is seen. While the assay has proved invaluable for sensitive measure of metal contents of SODs, it also has utility in assessing overall protein stability under different conditions. FIG. 25 illustrates that the $t_{1/2}$ for metal release by A4V (red trace) is signifcantly faster than for wild-type SOD. Faster metal release under denaturing conditions has been a consistent finding for all of the FALS mutants purified to date. If the denaturant is left out of this assay, none of the specifically-bound zinc and copper is released from the SODs. Thus, the PAR assay in the presence of guanidine HCl can be used as a measure of overall protein stability and can reveal subtle differences in the same protein under differing conditions (see FIG. 26).

EXAMPLE 30
Effect of Zinc and Reductive Cycling on SOD Stability

If the metal release assay is carried out in (5 M guandine HCl) using wild-type SOD which has been made zinc-deficient by selective remetallation of apoSOD, it is visually apparent that the copper is released very quickly (FIG. 26, black trace). Reduction of the SOD-bound copper with either $H_2O_2$ or sodium borohydride has no effect on the rate of metal release (green and magenta traces, respectively) indicating that there has been no net gain in protein stability as a result of copper reduction. Addition of one equivalent of zinc (blue trace) slows the rate of metal release considerably, consistent with an overall enhancement in protein stability. Reduction of the zinc-and copper-containing enzyme confers a dramatic increase in protein stabiliy over and above the effects of zinc alone (red trace). What's more, this slower rate of metal release was still seen 24 hr later—long after the enzyme had reoxidized (dark green trace) (the increase in total absorbance change with the blue and red traces simply reflects the presence of zinc and the higher extinction coefficient associated with the $Zn-PAR_2$ complex.)

The effects of reduction on metal release with wild-type and three FALS mutants are the same as for rematallated zinc-deficient wild-type (FIG. 27), i.e., in all cases the rates are considerably slower with reduced enzyme (FIG. 27, solid lines). Qualitative extrapolation of these results to the in vivo situation has two very important implications: 1) that zinc-deficient SOD is considerably less stable or, conversely, that zinc binding increases protein stability, and 2) that one cycle of enyzme turnover (i.e., reduction by first superoxide molecule and reoxidation by the second superoxide) confers an additional element of protein stability possibly by optimizing the geometry of the metal binding ligands in the active site (see FIG. 28 for discussion). A further implication stemming from the apparent need for one cycle of enzyme turnover is that, following metal insertion by the copper chaperone for SOD (CCS) but prior to turnover, a period of relative susceptibility exists whereby metals could be removed more easily by other metal binding proteins in the cell. One of these proteins could be neurofilament-L (see FIGS. 29 and 30).

Zinc Binding to apoSODs, CCS Peptides, and NF-L

The versatility of the PAR assay is illustrated through its use in quantifying the amount of zinc (or copper, see FIG. 31) which a protein or peptide is capable of binding. The only requirement for this assay is that the protein or peptide in question bind zinc with an affinity greater than or equal to $7.7 \times 10^{-11}$ M$^{-1}$ which is the binding for Zn-PAR$_2$. FIG. 29 shows the results of titrating a phosphate buffered solution (pH 7.4) solution containing 100 μM PAR and 10 μM zinc. The use of a 10-fold molar excess of PAR ensures that all the zinc is present as the Zn-PAR$_2$ complex. The decrease in absorbance with each addition of protein or peptide is a precise measure of the amount of zinc lost from the Zn-PAR$_2$ complex and thus bound by the protein or peptide. Because this is a competition-type assay, the slopes of the titration curves are an index of relative affinity[1]. For example, the slopes for apoA4V and apoD124N SOD (red and green, respectively) are quite similar and less steep than the slope for apowild-type SOD, consistent with the lower affinities of A4V and D124N.

[1] NOTE that slopes reflect relative affinity only when the binding stoichiometry is 1:1, i.e., if a protein bound two zinc atoms per mole then the slope would be twice as steep even though the affinity was unchanged. In the case of apoSODs and CCS peptides, the stoichiometry is 1:1 and thus comparisons are valid.

CCS Peptides

Two hexapeptides based on the copper binding region of the copper chaperone for SOD (CCS) bind zinc albeit with lower affinity than any of the apoSODs (FIG. 29). Although it is not possible to precisely extrapolate peptide binding to CCS itself, this differential affinity suggests that CCS could bind zinc in vivo and 'hand it off' to apoSOD quite readily. Both peptides bind zinc and copper (see FIG. 31) via their two cysteine residues. The MHCGAC peptide has the higher affinity of the two which is likely related to the presence of the additional metal ligand histidine.

NF-L

Recombinant mouse NF-L (rNF-L) has an extraordinary zinc binding ratio. First preparations of rNF-L bound about 12 zinc atoms per molecule. However, by rigorously controlling trace metal contamination during grow-up and purification to one can obtain binding stoichiometries between 17 and 20 zincs per rNF-L molecule (FIG. 29). Furthermore, roughly 60% of the zinc bound to rNF-L in these in vitro experiments cannot be recovered from the protein even under strong denaturing conditions. There is metal competition in that pre-saturation of rNF-L with calcium decreases the zinc binding ratio to around 12:1 indicating that calcium and zinc share some binding sites.

Zinc Binding by Purified Triplet Neurofilaments

The zinc binding capacity of triplet neurofilament preparations purified from bovine spinal cord was also examined. Using estimates of the ratios of NF-L to NF-M to NF-H in preps, it was determined that 7–8 zinc atoms were bound per NF-L subunit. It is not known whether NF-M and NF-H contributed to that ratio nor was it known how much or what kinds of metals were already bound prior to purification. However, these results did confirm that high zinc binding was not a peculiar artifact of the recombinant protein.

Regions of Zinc Binding on NF-L Polypeptides

Isolation of zinc binding to different regions of the rNF-L protein served to confirm not only that zinc binding sites existed in different regions but also that the high stoichiometry was correct. FIG. 30 shows the relative amounts of zinc bound by truncated mutants of mouse NF-L. Based on the absence of the different protein regions in the different mutants and the fact that full length rNF-L bound 18 zinc atoms, it is possible to calculate that (of the 18 zincs bound by full length rNF-L) roughly nine zinc atoms are bound by the head region (N-terminal 84 amino acids), seven zincs by the tail region (C-terminal 128 amino acids) and two zincs by the rod region (middle 85–415 residues) for a total of 20 zincs. Examination of the primary sequence of mouse NF-L reveals only a few of the traditional zinc ligands such histidine or cysteine; one histidine is present in the first 84 amino acids (head region) and none are in the 124 C-terminal residues (tail region). The only residues present in sufficient numbers to account for the high zinc binding are serines. Twenty-seven serines are present in the head and 17 in the tail. Regardless of the how or why NF-L binds so much zinc, it must comprize an enormous 'zinc sink' in neuronal cells, particularly in motor neurons. NF-L is an abundant protein anyway, but a zinc binding stoichiometry of 18:1 means that, with regard to its ability to compete with other zinc-binding proteins like SOD, its effective concentration is 18-fold greater than its actual protein concentration.

Copper Binding by apoSODs and CCS Peptides

Copper binding by apoSODs and CCS peptides was compared using the PAR competition assay described above starting with 10 μM copper (rather than zinc) pre-bound to PAR. FIG. 31 shows that apoA4V, apoD124N, and apo-wild-type SOD all bound copper with virtually the same affinity.

The two CCS peptides bind copper with greater affinity than do the apoSODs. However, the significance of this finding is difficult to assess, not only because of the caveats of extrapolating peptide binding data to CCS protein but also because other experiments with the Cu$^{+1}$ chelators BCS and NCS have shown that CCS peptides bind Cu$^{+1}$ whereas apoSODs bind Cu$^{+2}$. Although apoSODs actually take up copper more efficiently as Cu$^{+1}$—a fact which favors the putative role of CCS as a copper "insertase" in vivo—we have been unable to demonstrate any CCS peptide-assisted copper incorporation in apoSODs. However, studies of this type need to be done using larger peptides which better mimic the actions of CCS as well as recombinant CCS itself.

Thus, the present invention is directed to a method of removing copper from a form of superoxide dismutase in an individual in need of such treatment, comprising the step of administering to the individual a pharmacologically effective dose of a copper$^{+1}$-specific chelator. In one aspect, the copper$^{+1}$-specific chelator is bathocuproine or a derivative or analog thereof. Preferably, the bathocuproine is administered in a dose of from about 0.2 mg/kg to about 20 mg/kg of body weight. In another aspect, the copper$^{+1}$-specific chelator is neocuproine or a derivative or analog thereof. Preferably, the neocuproine is administered in a dose of from about 0.2 mg/kg to about 20 mg/kg of body weight.

The present invention is also directed to a pharmaceutical composition, comprising neocuproine and a pharmaceutically acceptable carrier. Further, the present invention is directed to a pharmaceutical composition, comprising bathocuproine and a pharmaceutically acceptable carrier.

The present invention is also directed to a method of treating an individual with ALS in an individual in need of such treatment, comprising the step of administering to the individual a pharmacologically effective dose of the composition disclosed herein.

The following references were cited herein:

Abe, K., Pan, L.-H., Watanabe, M., Kato, T. and Itoyama, Y. (1995). Induction of nitrotyrosine-like immunoreactivity in the lower motor neuron of amyotrophic lateral sclerosis. *Neurosci. Lett.* 199, 152–154.

Beckman, J. S. (1996a). Nitric Oxide, Superoxide and Peroxynitrite in CNS Injury. *Primer on Cerebrovascular Diseases*. (Welch, K. M., Caplan, L., Reis, D., Weir, B. and Siesjö, B.) pp. Academic Press, New York.

Beckman, J. S. (1996b). Oxidative damage and tyrosine nitration from peroxynitrite. *Chem. Res. Toxicol.* 9, 836–844.

Beckman, J. S., Chen, J., Ischiropoulos, H. and Crow, J. P. (1994a). Oxidative chemistry of peroxynitrite. *Methods Enzymol.* 233, 229–240.

Beckman, J. S., Ischiropoulos, H., Zhu, L., van der Woerd, M., Smith, C., Chen, J., Harrison, J., Martin, J. C. and Tsai, M. (1992). Kinetics of superoxide dismutase- and iron-catalyzed nitration of phenolics by peroxynitrite. *Arch. Biochem. Biophys.* 298, 438–445.

Beckman, J. S. and Koppenol, W. H. (1996). Nitric oxide, superoxide, and peroxynitrite—the good, the bad, and the ugly. *Am. J Physiol.* 271 (Cell Physiol. 40), C1424–C1437.

Beckman, J. S., Ye, Y. Z., Anderson, P., Chen, J., Accavetti, M. A., Tarpey, M. M. and White, C. R. (1994b). Extensive nitration of protein tyrosines in human atherosclerosis detected by immunohistochemistry. *Biol. Chem. Hoppe-Seyler.* 375, 81–88.

Brady, S. T. (1993). Motor neurons and neurofilaments in sickness and in health. *Cell.* 73, 1–3.

Carpenter, S. (1968). Proximal axonal enlargements in motor neuron disease. *Neurology.* 18, 841–851.

Chiu, F. C. and Norton, W. T. (1982). The cytoskeleton of primary astrocytes in culture contains actin, glial fibrillary acidic protein, and the fibroblast-type filament protein, vimentin. *J. Neurochem.* 39, 1252–1260.

Chou, S. M., Wang, H. S. and Komai, K. (1996a). Colocalization of NOS and superoxide dismutaseI in neurofilament accumulation within motor neurons of amyotrophic lateral sclerosis: an immunohistochemical study. *J. Chem. Neuroanat.* 10, 249–258.

Chou, S. M., Wang, H. S. and Taniguchi, A. (1996b). Role of superoxide dismutase-1 and nitric oxide/cyclic GMP cascade on neurofilament aggregation in ALS/MND. *J. Neurol. Sci.* 139(Suppl), 16–26.

Cohlberg, J. A., Hajarian, H., Tran, T., Alipourjeddi, P. and Noveen, A. (1995). Neurofilament protein heterotetramers as assembly intermediates. *J. Biol. Chem.* 270, 9334–9339.

Collard, J. F., Cote, F. and Julien, J. P. (1995). Defective axonal transport in a transgenic mouse model of amyotrophic lateral sclerosis. *Nature.* 375, 12–13.

Cote, F., Collard, J. F. and Julien, J. P. (1993). Progressive neuropathy in transgenic mice expressing the human neurofilament heavy gene: a mouse model of amyotrophic lateral sclerosis. *Cell.* 73, 35–46.

Dal Canto, M. C. and Gurney, M. E. (1995). Neuropathological changes in two lines of mice carrying a transgene for mutant human Cu,Zn superoxide dismutase, and in mice overexpressing wild type human superoxide dismutase: a model of familial amyotrophic lateral sclerosis (FALS). *Brain Res.* 676, 25–40.

Fuchs, E. and Weber, K. (1994). Intermediate Filaments: Structure, Dynamics, Function, and Disease. *Annual Review of Biochemistry.* (Richardson, C. C., Abelson, J. N., Meister, A. and Walsh, C. T.) pp. 345–382. Annual Reviews Inc, Palo Alto.

Greis, K. D., Zhu, S. and Matalon, S. (1996). Identification by tandem electrospray mass spectrometry of sites of tyrosine nitration on surfactant protein a. *Arch Biochem Biophys.* 335: 396–402.

Heins, S., Wong, P. C., Muller, S., Goldie, K., Cleveland, D. W. and Aebi, U. (1993). The rod domain of NF-L determines neurofilament architecture, whereas the end domains specify filament assembly and network formation. *J. Cell Biol.* 123, 1517–1533.

Hoffman, P., Cleveland, D., Griffin, J., Landes, P., Cowan, N. and Price, D. (1987). Neurofilament gene expression: a major determinant of axonal caliber. *Proc Natl Acad Sci USA.* 84, 3472–3476.

Ischiropoulos, H., Zhu, L. and Beckman, J. S. (1992a). Peroxynitrite formation from macrophage-derived nitric oxide. *Arch. Biochem. Biophys.* 298, 446–451.

Ischiropoulos, H., Zhu, L., Chen, J., Tsai, H. M., Martin, J. C., Smith, C. D. and Beckman, J. S. (1992b). Peroxynitrite-mediated tyrosine nitration catalyzed by superoxide dismutase. *Arch. Biochem. Biophys.* 298, 431–437.

Itoh, T., Sobue, G., Ken, E., Mitsuma, T., Takahashi, A. and Trojanowski, J. Q. (1992). Phosphorylated high molecular weight neurofilament protein in the peripheral motor, sensory and sympathetic neuronal perikarya: system-dependent normal variations and changes in amyotrophic lateral sclerosis and multiple system atrophy. *Acta Neuropathol.* 83, 240–245.

Koppenol, W. H., Kissner, R. and Beckman, J. S. (1995). Syntheses of peroxynitrite. To go with the flow or on solid grounds? *Methods in Enzymology.* (Packer, L.) pp. 296–302. Academic Press, San Diego.

Koppenol, W. H., Moreno, J. J., Pryor, W. A., Ischiropoulos, H. and Beckman, J. S. (1992). Peroxynitrite, a cloaked oxidant formed by nitric oxide and superoxide. *Chem. Res. Toxicol.* 5, 834–842.

Lee, M. K., Marszalek, J. R. and Cleveland, D. W. (1994). A mutant neurofilament subunit causes massive, selective motor neuron death: Implications for the pathogenesis of human motor neuron disease. *Neuron.* 13, 975–988.

Lupas, A. (1996). Coiled coils: new structures and new functions. *TIBS.* 21, 375–382.

Mann, M. and Wilm, M. (1995). Electrospray mass spectrometry for protein characterization. *TIBS.* 20, 219–224.

Nixon, R. A. and Lewis, S. E. (1986). Differential turnover of phosphate groups on neurofilament subunits in mammalian neurons in vivo. *J Biol Chem.* 26, 16298–16301.

Nixon, R. A. and Shea, T. B. (1992). Dynamics of neuronal intermediate filaments: A developmental perspective. *Cell Motility and the Cytoskeleton.* 22, 81–91.

Smith, C. D., Carson, M., Van der Woerd, M., Chen, J., Ischiropoulos, H. and Beckman, J. S. (1992). Crystal structure of peroxynitrite-modified bovine Cu,Zn superoxide dismutase. *Arch. Biochem. Biophys.* 299, 350–355.

Strong, M. J. and Jakowec, D. M. (1994). 200 kDa and 160 kDa neurofilament protein phosphatase resistance following in vivo aluminum chloride exposure. *Neurotoxicology.* 15, 700–708.

Xu, Z., Cork, L., Griffin, J. and Cleveland, D. (1993). Increased expression of neurofilament subunit NF-L produces morphological alterations that resemble the pathology of human motor neuron disease. *Cell.* 73, 23–33.

Ye, Y. Z., Strong, M., Huang, Z.-Q. and Beckman, J. S. (1996). Antibodies that recognize nitrotyrosine. *Methods in Enzymology.* (Packer, L.) pp. 201–209. Academic Press, San Diego.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of removing copper from a form of superoxide dismutase in an individual in need of such treatment, comprising the step of administering to the individual a pharmacologically effective dose of a copper$^{+1}$-specific chelator.

2. The method of claim 1, wherein said copper$^{+1}$-specific chelator is bathocuproine or a derivative or analog thereof.

3. The method of claim 2, wherein said bathocuproine is administered in a dose of from about 0.2 mg/kg to about 20 mg/kg of body weight.

4. The method of claim 1, wherein said copper$^{+1}$-specific chelator is neocuproine or a derivative or analog thereof.

5. The method of claim 2, wherein said neocuproine is administered in a dose of from about 0.2 mg/kg to about 20 mg/kg of body weight.

6. A pharmaceutical composition, comprising neocuproine and a pharmaceutically acceptable carrier.

7. A pharmaceutical composition, comprising bathocuproine and a pharmaceutically acceptable carrier.

8. A method of treating an individual with ALS in an individual in need of such treatment, comprising the step of administering to the individual a pharmacologically effective dose of the composition of claim 6.

9. The method of claim 8, wherein said composition is administered in a dose of from about 0.2 mg/kg to about 20 mg/kg of body weight.

10. A method of treating an individual with ALS in an individual in need of such treatment, comprising the step of administering to the individual a pharmacologically effective dose of the composition of claim 7.

11. The method of claim 10, wherein said composition is administered in a dose of from about 0.2 mg/kg to about 20 mg/kg of body weight.

* * * * *

UNITED STATES PATENT AND TRADEMARK OFFICE
CERTIFICATE OF CORRECTION

PATENT NO. : 6,022,879
DATED : February 8, 2000
INVENTOR(S) : John P. Crow and Joseph S. Beckman It is certified that error appears in the above-identified patent and that said Letters Patent is hereby corrected as shown below:

<u>Column 1,</u>
Line 13, please insert -- NS35871, -- before "NS33291".

Signed and Sealed this

Twelfth Day of August, 2003

JAMES E. ROGAN
*Director of the United States Patent and Trademark Office*